(12) United States Patent
Rothenberg et al.

(10) Patent No.: US 12,297,501 B2
(45) Date of Patent: May 13, 2025

(54) METHODS FOR DIAGNOSING AND TREATING EOSINOPHILIC GASTRITIS

(71) Applicant: CHILDREN'S HOSPITAL MEDICAL CENTER, Cincinnati, OH (US)

(72) Inventors: Marc E. Rothenberg, Cincinnati, OH (US); Tetsuo Shoda, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 603 days.

(21) Appl. No.: 16/800,390

(22) Filed: Feb. 25, 2020

(65) Prior Publication Data

US 2020/0271668 A1  Aug. 27, 2020

Related U.S. Application Data

(60) Provisional application No. 62/813,838, filed on Mar. 5, 2019, provisional application No. 62/810,093, filed on Feb. 25, 2019.

(51) Int. Cl.
*C12Q 1/68* (2018.01)
*C12Q 1/6883* (2018.01)

(52) U.S. Cl.
CPC ............ *C12Q 1/6883* (2013.01); *C12Q 1/68* (2013.01); *C12Q 2600/106* (2013.01); *C12Q 2600/158* (2013.01); *G01N 2800/06* (2013.01); *G01N 2800/50* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. |
| 4,522,811 A | 6/1985 | Eppstein et al. |
| 4,675,604 A | 6/1987 | Moyer et al. |
| 4,675,904 A | 6/1987 | Silverman |
| 5,015,627 A | 5/1991 | Lindsey |
| 5,148,483 A | 9/1992 | Silverman |
| 5,288,644 A | 2/1994 | Beavis et al. |
| 5,412,073 A | 5/1995 | Kalsheker |
| 5,445,934 A | 8/1995 | Fodor et al. |
| 5,530,101 A | 6/1996 | Queen et al. |
| 5,700,637 A | 12/1997 | Southern |
| 5,744,305 A | 4/1998 | Fodor et al. |
| 5,888,510 A | 3/1999 | Kishimoto et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,403,782 B1 | 6/2002 | Luster et al. |
| 6,429,027 B1 | 8/2002 | Chee et al. |
| 6,733,977 B2 | 5/2004 | Besemer et al. |
| 6,780,973 B1 | 8/2004 | Luster et al. |
| 6,825,350 B2 | 11/2004 | Crooks et al. |
| 6,858,394 B1 | 2/2005 | Chee et al. |
| 7,364,858 B2 | 4/2008 | Barany et al. |
| 7,514,209 B2 | 4/2009 | Dai et al. |
| 7,582,620 B2 | 9/2009 | Lew |
| 7,592,326 B2 | 9/2009 | Karaolis |
| 7,879,547 B2 | 2/2011 | Rothenberg et al. |
| 8,030,003 B2 | 10/2011 | Rothenberg |
| 8,409,565 B2 | 4/2013 | Levi-schaffer et al. |
| 9,260,756 B2 | 2/2016 | Rothenberg et al. |
| 9,345,763 B2 | 5/2016 | Rothenberg et al. |
| 9,517,238 B2 | 12/2016 | Rochman et al. |
| 9,624,545 B2 | 4/2017 | Rothenberg et al. |
| 9,691,411 B2 | 6/2017 | Scherer et al. |
| 9,803,244 B2 | 10/2017 | Rothenberg et al. |
| 9,928,344 B2 | 3/2018 | Rothenberg et al. |
| 9,982,303 B2 | 5/2018 | Rothenberg |
| 10,155,985 B2 | 12/2018 | Rothenberg et al. |
| 10,294,517 B2 | 5/2019 | Rothenberg et al. |
| 10,422,004 B2 | 9/2019 | Rothenberg et al. |
| 10,821,094 B2 | 11/2020 | Azouz et al. |
| 11,564,905 B2 | 1/2023 | Azouz |
| 2002/0077825 A1 | 6/2002 | Silverman et al. |
| 2003/0078768 A1 | 4/2003 | Silverman et al. |
| 2003/0157479 A1 | 8/2003 | Bachmann et al. |
| 2003/0167189 A1 | 9/2003 | Lutgen et al. |
| 2003/0194404 A1 | 10/2003 | Greenfeder et al. |
| 2004/0033502 A1 | 2/2004 | Williams et al. |
| 2004/0141951 A1 | 7/2004 | Rothenberg et al. |

(Continued)

FOREIGN PATENT DOCUMENTS

CN     101275941 A    10/2008
EP       0619321 A1   10/1994

(Continued)

OTHER PUBLICATIONS

Ishahara et al; Internal Medicine, DOI: 10.2169/internalmedicine.8763-16; 2017.*
Shoda et al; J Allergy Clin Immunol, 1438, 2016.*
Accession No. E-MEXP-3298.
Accession No. E-MEXP-3345.
Accession No. E-MEXP-3346.
Accession No. E-MEXP-3350.
Accession No. E-MEXP-3351.
Accession No. E-MEXP-3353.
Asthma and Immunology, American College of Allergy, Oct. 10, 2017.
Eosinophilic Esophagitis, American College of Gastroenterology, Oct. 10, 2017.
Extended European Search Report for EP Application No. 15828951.2, mailed on Nov. 16, 2017, 8 pages.
Extended European Search Report issued in European Application No. 16885429.7, mailed on Jul. 23, 2019, 15 pages.
Zimmerman et al. (Feb. 2003) "Chemokines in Asthma: Cooperative Interaction between Chemokines and IL-13", The Journal of Allergy and Clinical Immunology, 111(2):227-242.

(Continued)

*Primary Examiner* — Jehanne S Sitton
(74) *Attorney, Agent, or Firm* — KDW Firm PLLC

(57) ABSTRACT

The present invention relates to methods for diagnosing, monitoring, and optionally treating eosinophilic gastritis (EG) and/or eosinophilic gastroenteritis (EGE), the methods comprising assaying one or more tissue, serum, or plasma biomarkers in a biological sample from the subject.

3 Claims, 20 Drawing Sheets

(56) References Cited

U.S. PATENT DOCUMENTS

| | | |
|---|---|---|
| 2005/0163764 A1 | 7/2005 | Medzhitov et al. |
| 2007/0059720 A9 | 3/2007 | Fuqua et al. |
| 2007/0233468 A1 | 10/2007 | Ozdas et al. |
| 2007/0233498 A1 | 10/2007 | Silverman et al. |
| 2008/0187908 A1 | 8/2008 | Adra |
| 2008/0201280 A1 | 8/2008 | Martin et al. |
| 2009/0233275 A1 | 9/2009 | Rothenberg |
| 2009/0269774 A1 | 10/2009 | Rothenberg et al. |
| 2010/0151472 A1 | 6/2010 | Nolan et al. |
| 2010/0240965 A1 | 9/2010 | Furuta et al. |
| 2010/0262603 A1 | 10/2010 | Odom et al. |
| 2011/0123530 A1 | 5/2011 | Arron et al. |
| 2011/0144183 A1 | 6/2011 | Paquet et al. |
| 2011/0195500 A1 | 8/2011 | Rothenberg |
| 2011/0301046 A1 | 12/2011 | Rothenberg et al. |
| 2012/0004205 A1 | 1/2012 | Rothenberg |
| 2012/0041911 A1 | 2/2012 | Pestian et al. |
| 2012/0283117 A1 | 11/2012 | Rothenberg |
| 2012/0288068 A1 | 11/2012 | Jaiswal et al. |
| 2013/0035961 A1 | 2/2013 | Yegnanarayanan |
| 2013/0065972 A1 | 3/2013 | Dent et al. |
| 2013/0324435 A1 | 12/2013 | Rothenberg et al. |
| 2014/0073801 A1 | 3/2014 | Storer et al. |
| 2014/0113372 A1 | 4/2014 | Haque et al. |
| 2014/0228301 A1 | 8/2014 | Meade et al. |
| 2014/0228315 A1 | 8/2014 | Rothenberg et al. |
| 2014/0286896 A1 | 9/2014 | Rothenberg et al. |
| 2014/0328861 A1 | 11/2014 | Payton et al. |
| 2014/0343255 A1 | 11/2014 | Gonzalez et al. |
| 2015/0038552 A1 | 2/2015 | Rothenberg et al. |
| 2015/0045334 A1 | 2/2015 | Rothenberg et al. |
| 2015/0182499 A1 | 7/2015 | Reboud-ravaux et al. |
| 2015/0355180 A1 | 12/2015 | Resnick et al. |
| 2016/0129012 A1 | 5/2016 | Rochman et al. |
| 2016/0177394 A1 | 6/2016 | Rothenberg et al. |
| 2016/0180041 A1 | 6/2016 | Pestian et al. |
| 2016/0213681 A1 | 7/2016 | Santus et al. |
| 2016/0264658 A1 | 9/2016 | Ahmed et al. |
| 2016/0304960 A1 | 10/2016 | Rothenberg |
| 2016/0312282 A1 | 10/2016 | Rothenberg et al. |
| 2017/0002021 A1 | 1/2017 | Wagberg |
| 2017/0061073 A1 | 3/2017 | Sadhasivam |
| 2017/0067111 A1 | 3/2017 | Rothenberg et al. |
| 2017/0183719 A1 | 6/2017 | Rothenberg et al. |
| 2017/0199191 A1 | 7/2017 | Fulkerson |
| 2017/0233813 A1 | 8/2017 | Rothenberg et al. |
| 2017/0281716 A1 | 10/2017 | Martin |
| 2019/0000799 A1 | 1/2019 | Azouz et al. |
| 2019/0046444 A1 | 2/2019 | Konduri et al. |
| 2020/0338043 A1 | 10/2020 | Azouz et al. |
| 2021/0080453 A1 | 3/2021 | Rothenberg et al. |

FOREIGN PATENT DOCUMENTS

| | | |
|---|---|---|
| EP | 0619321 B1 | 1/1999 |
| EP | 0949271 A1 | 10/1999 |
| GB | 2450780 A | 1/2009 |
| WO | 8910977 A1 | 11/1989 |
| WO | 9937319 A1 | 7/1999 |
| WO | 2005007175 A2 | 1/2005 |
| WO | 2005033134 A2 | 4/2005 |
| WO | 2005106492 A2 | 11/2005 |
| WO | 2006083390 A3 | 8/2006 |
| WO | 2006119343 A1 | 11/2006 |
| WO | 2009015434 A1 | 2/2009 |
| WO | 2009018493 A1 | 2/2009 |
| WO | 2009061819 A1 | 5/2009 |
| WO | 2009089062 A2 | 7/2009 |
| WO | 2009089062 A3 | 9/2009 |
| WO | 2009089062 A8 | 9/2010 |
| WO | 2010126867 A1 | 11/2010 |
| WO | 2012025765 A1 | 3/2012 |
| WO | 2012094643 A2 | 7/2012 |
| WO | 2012094643 A3 | 11/2012 |
| WO | 2012174549 A2 | 12/2012 |
| WO | 2012177945 A2 | 12/2012 |
| WO | 2012178188 A2 | 12/2012 |
| WO | WO2012/178188 * | 12/2012 |
| WO | 2012174549 A9 | 2/2013 |
| WO | 2013082308 A1 | 6/2013 |
| WO | 2013126834 A1 | 8/2013 |
| WO | 2013155010 A1 | 10/2013 |
| WO | 2014059178 A1 | 4/2014 |
| WO | 2014190269 A1 | 11/2014 |
| WO | 2015017731 A1 | 2/2015 |
| WO | 2015127379 A1 | 8/2015 |
| WO | 2015142739 A1 | 9/2015 |
| WO | 2016023026 A1 | 2/2016 |
| WO | 2016196146 A1 | 12/2016 |
| WO | 2017048860 A1 | 3/2017 |
| WO | 2017123401 A1 | 7/2017 |
| WO | 2019204580 A1 | 10/2019 |

OTHER PUBLICATIONS

International Preliminary Report on Patentability received for PCT International Application No. PCT/US16/68238, mailed on Jul. 26, 2018, 7 pages.

International search report issued in PCT/US2015/020768, mailed on Jun. 12, 2015.

International Search Report for International Application No. PCT/US2016/034185 mailed on Sep. 9, 2016, filed May 25, 2016, 8 pages.

International Search Report received for PCT Patent International Application No. PCT/US16/68238, mailed on Mar. 27, 2017, 8 pages.

International Search Report received for PCT Patent International Application No. PCT/US2014/039357, mailed on Sep. 24, 2014, 8 pages.

International Search Report received for PCT Patent International Application No. PCT/US2014/049301, mailed on Dec. 8, 2014, 8 pages.

International Search Report received for PCT Patent International Application No. PCT/US2015/017134, mailed on May 6, 2015, 11 pages.

Mus Musculus TaqMan Probe Mm00446968_m1 for Hypoxanthine Guanine Phosphoribosyl Transferase (Hprt).

Mus musculus TaqMan probe Mm01216172_m1 for chemokine (C—C motif) receptor 3 (Ccr3).

Zheng et al. (Mar. 2009) "Transgenic Expression of Interleukin-13 in the Skin Induces a Pruritic Dermatitis and Skin Remodeling", Journal of Investigative Dermatology, 129(3):742-751.

Zimmermann et al. (Apr. 30, 1999) "CC Chemokine Receptor-3 Undergoes Prolonged Ligand-induced Internalization", Journal of Biological Chemistry, 274(18):12611-12618.

The Merck Manual, 1992, 1229-1230 & 1233.

The Merck Manual, 1992, 646-649.

Zhen et al. (Feb. 2007) "IL-13 and Epidermal Growth Factor Receptor Have Critical but Distinct Roles in Epithelial Cell Mucin Production", American Journal of Respiratory Cell and Molecular Biology, 36(2):244-253.

Abidi et al. (2008) "Eosinopenia is a Reliable Marker of Sepsis on Admission to Medical Intensive Care Units", Critical Care, R59, 12(2):10 pages.

Abonia et al. (2012) "Eosinophilic Esophagitis: Rapidly Advancing Insights", Annual Review of Medicine, 63:421-434.

Aceves et al. (Jan. 2007) "Esophageal Remodeling in Pediatric Eosinophilic Esophagitis", The Journal of Allergy and Clinical Immunology, 119(1):206-212.

Aceves et al. (Dec. 2010) "Mast Cells Infiltrate the Esophageal Smooth Muscle in Patients with Eosinophilic Esophagitis, Express TGF-31, and Increase Esophageal Smooth Muscle Contraction", The Journal of Allergy and Clinical Immunology, e4, 126(6):1198-204.

Ackerman et al. (Apr. 26, 2002) "Charcot-Leyden Crystal Protein (Galectin-10) Is Not a Dual Function Galectin with Lysophospholipase

(56) References Cited

OTHER PUBLICATIONS

Activity but Binds a Lysophospholipase Inhibitor in a Novel Structural Fashion", Journal of Biological Chemistry, 277(17):14859-14868.
Adachi et al. (Dec. 15, 2007) "Transduction of Phosphatase and Tensin Homolog Deleted on Chromosome 10 into Eosinophils Attenuates Survival, Chemotaxis, and Airway Inflammation", The Journal of Immunology, 179(12):8105-8111.
Akuthota et al. (2011) "Eosinophils: Offenders or General Bystanders in Allergic Airway Disease and Pulmonary Immunity?", Journal of Innate Immunity, 3(2):113-119.
Alexander Jeffreya. (May 2014) "Topical Steroid Therapy for Eosinophilic Esophagitis", Gastroenterology & Hepatology, 10(5):327-329.
Allakhverdi et al. (Feb. 2009) "CD34+ Hemopoietic Progenitor Cells are Potent Effectors of Allergic Inflammation", Journal of Allergy and Clinical Immunology, 123(2):472-478.
Anderson et al. (Sep. 2011) "Evaluation of a morphine maturation model for the prediction of morphine clearance in children", British Journal of Clinical Pharmacology, 72(3):518-520.
Andrews, "Allosteric Small Molecule Inhibitors of the NGF/TrkA Pathway A New Approach to Treating Inflammatory Pain", Available at: http://www.arraybiopharma.com/files/6313/9810/8021/PubAttachment587.pdf, 33 pages.
Angus et al. (Jul. 2009) "Epidemiology of Severe Sepsis in the United States: Analysis of Incidence, Outcome, and Associated Costs of Care", Critical Care Medicine, 29(7):1303-1310.
Anonymous (Jul. 7, 2015) "TaqMan(R) Human Micro RNA Arrays", 2 pages.
Anthony et al. (Dec. 2007) "Protective Immune Mechanisms in Helminth Infection", Nature Reviews Immunology, 7(12):975-987.
April et al. (Dec. 3, 2009) "Whole-Genome Gene Expression Profiling of Formalin-Fixed, Paraffin-Embedded Tissue Samples", Plos One, e8162, 4(12):10 pages.
Arefi et al. (Sep. 2012) "Response to Imatinib Mesylate in Patients with Hypereosinophilic Syndrome", International Journal of Hematology, 96(3):320-326.
Arroyo et al. (Mar. 22, 2011)"Argonaute2 Complexes Carry a Population of Circulating MicroRNAs Independent of Vesicles in Human Plasma", Proceedings of the National Academy of Sciences of the United States of America, 108(12):5003-5008.
Assa'Ad et al. (Nov. 2011) "An Antibody Against IL-5 Reduces Numbers of Esophageal Intraepithelial Eosinophils in Children With Eosinophilic Esophagitis", Gastroenterology, 141(5):1593-1604.
Assa'Ad et al., "Pediatric Patients With Eosinophilic Esophagitis: An 8-year Follow-up", The Journal of Allergy and Clinical Immunology, Mar. 2007, 119(3):731-738.
Attwood et al. (Jan. 1993) "Esophageal Eosinophilia with Dysphagia. A Distinct Clinicopathologic Syndrome", Digestive Diseases and Sciences, 38(1):109-116.
Ayala et al. (May 15, 1996) "Differential Induction of Apoptosis in Lymphoid Tissues during Sepsis: Variation in Onset, Frequency, and the Nature of the Mediators", Blood, 87(10):4261-4275.
Azouz et al. (May 27, 2020) "Functional Role of Kallikrein 5 and Proteinase-activated Receptor 2 in Eosinophilic Esophagitis", Science Translational Medicine, eaaz7773, 12(545):34 pages.
Azouz et al. (Feb. 2016) "Loss of SPINK7 in Esophageal Epithelial Cells Unleashes a Pro-Inflammatory Response Characterized By Excessive Cytokine Production and Loss of Barrier Function", The Journal of Allergy and Clinical Immunology, 137(2):1 page.
Azouz et al. (Jun. 6, 2818) "The Antiprotease SPINK7 Serves as an Inhibitory Checkpoint for Esophageal Epithelial Inflammatory Responses", Science Translational Medicine, 10(444):29 pages.
Baker et al. (Apr. 2, 2003) "The Central Role of Receiver Operating Characteristic (ROC) Curves in Evaluating Tests for the Early Detection of Cancer", Journal of the National Cancer Institute, 95(7):511-515.
Azouz, et al. (May 27, 2020) "Supplemental Materials for Functional Role of Kallikrein 5 and Proteinase-activated 9 Receptor 2 in Eosinophilic Esophagitis," Sci. Transl. Med. 12 eaaz773, sciencemag.org/cgi/contenVfull/12/545, 26 pgs.
Saeki, et al. (Mar. 2, 2001) "Identification of a Potent and Nonpeptidyl CCR3 Antagonist", Biochemical and Biophysical Research Communications 281(3): 779-782, 4 pgs.
Sonkoly, et al., (Jul. 2007) "MicroRNAs: Novel Regulators involved in the Pathogenesis of Psoriasis?", PLoS One, 3610, 2(7): 8 pages.
Baldrick et al. (Jul.-Aug. 2007) "Pollinex Quattro Ragweed: Safety Evaluation of a New Allergy Vaccine Adjuvanted with Monophosphoryl Lipid a (MPL) for the Treatment of Ragweed Pollen Allergy", Journal of Applied Toxicology, 27(4):399-409.
Barratt et al. (Apr. 18, 2012) "ABCB1 haplotype and OPRM1 118A>G genotype interaction in methadone maintenance treatment pharmacogenetics", 5(1):53-62.
Barski et al. (Oct. 2009) "Chromatin Poises miRNA- And Protein-coding Genes for Expression", Genome Research, 19(10):1742-151.
Bass D.A. (Jun. 1975) "Behavior of Eosinophil Leukocytes in Acute Inflammation. I. Lack of Dependence on Adrenal Function", Journal of Clinical Investigation, 55(6):1229-1236.
Bass D.A. (Oct. 1975) "Behavior of Eosinophil Leukocytes in Acute Inflammation. II. Eosinophil Dynamics During Acute Inflammation", Journal of Clinical Investigation, 56(4):870-879.
Ben-Dor et al. (2000) "Tissue Classification with Gene Expression Profiles", Journal of Computational Biology, 7(3-4):559-583.
Berkman et al. (Jun. 2001) "Eotaxin-3 but Not Eotaxin Gene Expression Is Upregulated in Asthmatics 24 Hours after Allergen Challenge", American Journal of Respiratory Cell and Molecular Biology, 24(6):682-687.
Bhattacharya et al. (Dec. 2007) "Increased Expression of Eotaxin-3 Distinguishes Between Eosinophilic Esophagitis and Gastroesophageal Reflux Disease", Human Pathology, 38(12):1744-1753.
Biesiada et al. (Nov. 2014) "Genetic risk signatures of opioid-induced respiratory depression following pediatric tonsillectomy", Pharmacogenomics, 15(14):1749-1762.
Biton et al. (Mar. 2011) "Epithelial MicroRNAs Regulate Gut Mucosal Immunity Via Epithelium-T Cell Crosstalk", Nature Immunology, 12(3):239-246.
Blanchard et al. (Jan. 2008) "Basics Pathogenesis of Eosinophilic Esophagitis", Gastrointestinal Endoscopy Clinics of North America, 18(1):133-143.
Blanchard et al. (Apr. 1, 2010) "Coordinate Interaction Between IL-13 and Epithelial Differentiation Cluster Genes in Eosinophilic Esophagitis", Journal of Immunology, 184(7):4033-4041.
Blanchard et al. (Sep. 19, 2006) "Eosinophilic Esophagitis: Pathogenesis, Genetics, and Therapy", The Journal of Allergy and Clinical Immunology, 118(5):1054-1059.
Blanchard et al. (Feb. 2006) "Eotaxin-3 and a Uniquely Conserved Gene-Expression Profile in Eosinophilic Esophagitis", Journal of Clinical investigation, 116(2):536-547.
Blanchard et al. (Dec. 2005) "Eotaxin-3/CCL26 Gene Expression in Intestinal Epithelial Cells is Up-regulated by Interleukin-4 and Interleukin-13 Via the Signal Transducer and Activator of Transcription 6", The International Journal of Biochemistry & Cell Biology, 37(12):2559-2573.
Blanchard et al. (Dec. 2007) "IL-13 Involvement in Eosinophilic Esophagitis: Transcriptome Analysis and Reversibility with Glucocorticoids", Journal of Allergy and Clinical Immunology, 120(6):1292-1300.
Blanchard et al. (Jan. 2007) "Il-13 Is Overexpressed In Eosinophilic Esophagitis And Induces Eotaxin-3 Expression In Esophageal Epithelial Cells", The Journal of Allergy and Clinical Immunology, S240, 1 page.
Blanchard et al. (Jul. 2008) "Periostin Facilitates Eosinophil Tissue Infiltration in Allergic Lung And Esophageal Responses", Mucosal Immunology, 1(4):289-296.
Blennow Kaj (Apr. 2004) "Cerebrospinal Fluid Protein Biomarkers for Alzheimer's Disease", NeuroRx, 1(2):213-225.
Bochner et al. (Jul. 2010) "What Targeting the Eosinophil has Taught Us About their Role in Diseases", The Journal of Allergy and Clinical Immunology, 126(1):16-25.

(56) References Cited

OTHER PUBLICATIONS

Boeuf et al. (Mar. 4, 2005) "CyProQuant-PCR: A Real Time RT-PCR Technique for Profiling Human Cytokines, Based on External RNA Standards, Readily Automatable for Clinical Use", BMC Immunology, 6:14 pages.

Bonini et al. (Oct. 1, 1996) "Circulating Nerve Growth Factor Levels are Increased in Humans with Allergic Diseases and Asthma", Proceedings of the National Academy of Sciences of the United States of America, 93(20):10955-10960.

Boon et al. (Oct. 23, 2003) "Comparison of Medulloblastoma and Normal Neural Transcriptomes Identifies a Restricted Set of Activated Genes", Oncogene, 22(48):7687-7694.

Branford et al. (Jul. 27, 2012) "Opioid genetics: the key to personalized pain control?", Clinical Genetics, 82(4):301-310.

Brightling et al. (Jan. 2010) "Interleukin-13: Prospects for New Treatments", Clinical & Experimental Allergy, 40(1):42-49.

Brodeur et al. (Jan. 1997) "Expression of TrkA, TrkB and TrkC in Human Neuroblastomas", Journal of Neuro-Oncology, 31(1-2):49-55.

Broide et al. (2009) "Advances in Mechanisms of Asthma, Allergy, and Immunology in 2010", The Journal of Allergy and Clinical Immunology, 127(3):689-695.

Broide et al. (2009) "Immunomodulation of Allergic Disease", Annual Review of Medicine, 60:279-291.

Buitenhuis et al. (Jun. 1, 2005) "Differential Regulation of Granulopoiesis by the Basic Helix-loop-helix Transcriptional Inhibitors Id1 and Id2", Blood, 105(11):4272-4281.

Bullens et al. (Nov. 3, 2006) "IL-17 mRNA in Sputum of Asthmatic Patients: Linking T Cell Driven Inflammation and Granulocytic Influx?", Respiratory Research, 7(1):9 pages.

Bullock et al. (Jul. 2007) "Interplay of Adaptive Th2 Immunity with Eotaxin-3/c-C Chemokine Receptor 3 in Eosinophilic Esophagitis", Journal of Pediatric Gastroenterology and Nutrition, 45(1):22-31.

Burnett et al. (Jan. 27, 2012) "RNA-based Therapeutics: Current Progress and Future Prospects", Chemistry & Biology, 19(1):60-71.

Buscaglia et al. (Jun. 2011) "Apoptosis and the Target Genes of MicroRNA-21", Chinese Journal of Cancer, 30(6):371-380.

Busse et al. (Apr. 2010) "A Review of Treatment with Mepolizumab, an Anti-il-5 Mab, in Hypereosinophilic Syndromes and Asthma", The Journal of Allergy and Clinical Immunology, 25(4):803-813.

Cai et al. (Mar. 2017) "The Imprinted H19 Noncoding RNA is a Primary MicroRNA Precursor", RNA, 13(3):313-316.

Caldwell et al. (Sep. 2017) "Cadherin 26 is an alpha integrin-binding epithelial receptor regulated during allergic inflammation", Mucosal Immunology, 10(5):1190-1201.

Caldwell et al. (Apr. 2010) "Glucocorticoid-regulated Genes in Eosinophilic Esophagitis: A Role for FKBP51", American Academy of Allergy, Asthma & Immunology, 125(4):879-888.

Cameron et al. (Mar. 2000) "Evidence for Local Eosinophil Differentiation Within Allergic Nasal Mucosa: Inhibition with Soluble IL-5 Receptor", The Journal of Immunology, 164(3):1538-1545.

Caramori et al. (Aug. 2005) "Anti-inflammatory Mechanisms of Glucocorticoids Targeting Granulocytes", Current Drug Targets— Inflammation & Allergy, 4(4):455-463.

Carriere et al. (Jan. 2, 2007) "IL-33, the IL-1-like Cytokine Ligand for ST2 Receptor, is a Chromatin-associated Nuclear Factor in Vivo", Proceedings of the National Academy of Sciences of the United States of America, 104(1):282-287.

Carthew et al. (Feb. 20, 2009) "Origins and Mechanisms of miRNAs and siRNAs", Cell, 136(4):642-655.

Chehade et al. (Jun. 2010) "Food Allergy and Eosinophilic Esophagitis", Current Opinion in Allergy and Clinical Immunology, 10(3):231-237.

Chen et al. (Jul. 1, 2009) "ToppGene Suite for Gene List Enrichment Analysis and Candidate Gene Prioritization", Nucleic Acids Research, 37(Suppl. 2): W305-W311.

Cheverud James M. (Jul. 2001) "A Simple Correction for Multiple Comparisons in Interval Mapping Genome Scans", Heredity, 87(Pt 1):52-58.

Cho et al. (Mar. 24, 2006) "Role of Early Growth Response-1 (Egr-1) in Interleukin-13-induced Inflammation and Remodeling", Journal of Biological Chemistry, 281(12):8161-8168.

Chu et al. (Jan. 9, 2011) "Eosinophils are Required for the Maintenance of Plasma Cells in the Bone Marrow", Nature Immunology, 12(2):151-159.

Clavijo et al. (Mar. 12, 2011) "A sensitive assay for the quantification of morphine and its active metabolites in human plasma and dried blood spots using high-performance liquid chromatography-tandem mass spectrometry", Analytical and Bioanalytical Chemistry, 400(3):715-728.

Cohen et al. (Aug. 2012) "Pharmacogenetics in perioperative medicine", Current opinion in anaesthesiology, 25(4):419-427.

Collins et al. (Jun. 2008) "Clinical, Pathologic, and Molecular Characterization of Familial Eosinophilic Esophagitis Compared With Sporadic Cases", Clinical Gastroenterology and Hepatology, 6(6):621-629.

Collins et al. (Mar. 2017) "Newly Developed and Validated Eosinophilic Esophagitis Histology Scoring System and Evidence that it Outperforms Peak Eosinophil Count for Disease Diagnosis and Monitoring", Diseases of the Esophagus, 30(3):1-8.

Simon et al. (Oct. 10, 2005) "Roadmap for Developing and Validating Therapeutically Relevant Genomic Classifiers", Journal of Clinical Oncology, 23(29):7332-7341.

Simonini et al. (Nov. 15, 2010) "Epigenetically Deregulated Microrna-375 is Involved in a Positive Feedback Loop with Estrogen Receptor Alpha in Breast Cancer Cells", Cancer Research, 70(22):9175-9184.

Sin et al. (Sep. 2011) "Nerve Growth Factor or IL-3 Induces more IL-13 Production from Basophils of Allergic Subjects than from Basophils of Nonallergic Subjects", The Journal of Allergy and Clinical Immunology, 108(3):387-393.

Yi et al. (Mar. 13, 2008) "A Skin MicroRNA Promotes Differentiation by Repressing 'Stemness'", Nature, 452(7184):225-229.

Slonim Donnak. (Dec. 2002) "From Patterns to Pathways: Gene Expression Data Analysis Comes of Age", Nature Genetics, 32:502-508.

Smith et al. (Jun. 2010) "Insulin-Like Growth Factor-I Regulation of Immune Function: A Potential Therapeutic Target in Autoimmune Diseases?", Pharmacological Reviews, 62(2):199-236.

Smith et al. (Feb. 7, 2010) "MicroRNAs, Development of Barrett's Esophagus, and Progression to Esophageal Adenocarcinoma", World Journal of Gastroenterology, 16(5):531-537.

Smith et al. (Dec. 2006) "Serine Proteases, their Inhibitors and Allergy", Allergy, 61(12):1441-1447.

Sonkoly et al. (Jul. 2007) "MicroRNAs: Novel Regulators Involved in the Pathogenesis of Psoriasis?", PLoS One, e610, 2(7):8 pages.

Sonkoly et al. (Dec. 2010) "MIR-155 is Overexpressed in Patients with Atopic Dermatitis and Modulates T-cell Proliferative Responses by Targeting Cytotoxic T Lymphocyte-associated Antigen 4", The Journal of Allergy and Clinical Immunology, 126(3):581-589.

Spergel et al. (Oct. 2005) "Treatment of Eosinophilic Esophagitis with Specific Food Elimination Diet Directed by a Combination of Skin Prick and Patch Tests", Annals of Allergy, Asthma & Immunology, 95(4):336-343.

Sprenger et al. (Jan. 2009) "Eosinophilic Oesophagitis: An Enigmatic, Emerging Disease", The Netherlands Journal of Medicine, 67(1):8-12.

Spry C. (Sep. 1976) "Eosinophilia in Addison's Disease", Yale Journal of Biology and Medicine, 49(4):411-413.

Stansfield et al. (Dec. 2009) "Periostin Is a Novel Factor in Cardiac Remodeling After Experimental and Clinical Unloading of the Failing Heart", The Annals of Thoracic Surgery, 88(6):1916-1921.

Stappert et al. (Aug. 1994) "A Short Core Region of E-cadherin is Essential for Catenin Binding and is Highly Phosphorylated", Cell Communication & Adhesion, 2(4):319-327.

Stein et al. (Jun. 2008) "Anti-IL-5 (Mepolizumab) Therapy Reduces Eosinophil Activation Ex Vivo and Increases IL-5 And IL-5 Receptor Levels", The Journal of Allergy and Clinical Immunology, 121(6):1473-1483

Stein et al. (Nov. 2010) "Targeting Interleukin (IL) 5 for Asthma and Hypereosinophilic Diseases", Recent Patents on Inflammation & Allergy Drug Discovery, 4(3):201-209.

(56) References Cited

OTHER PUBLICATIONS

Stothard P. (Jun. 2000) "Javascript Programs for Analyzing and Formatting Protein and DNA Sequences", BioTechniques, 28(6);1102, 1104.
Straumann et al. (Nov. 2010) "Budesonide Is Effective in Adolescent and Adult Patients With Active Eosinophilic Esophagitis", Gastroenterology, 139(5):1526-1537.
Straumann et al. (Feb. 2005) "Eosinophilic esophagitis: escalating epidemiology?", The Journal of Allergy and Clinical Immunology, 115(2):418-419.
Straumann Alex (Feb. 3, 2012) "Eosinophilic Esophagitis: Rapidly Emerging Disorder", Swiss Medical Weekly, w13513, 142:8 pages.
Straumann et al. (Dec. 2001) "Idiopathic Eosinophilic Esophagitis is Associated with a T(H)2-type Allergic Inflammatory Response", The Journal of Allergy and Clinical Immunology, 108(6):954-961.
Straumann et al. (May 2011) "Long-term Budesonide Maintenance Treatment is Partially Effective for Patients with Eosinophilic Esophagitis", Clinical Gastroenterology and Hepatology, 9(5):370-372.
Straumann et al. (Apr. 2012) "Pediatric and Adult Eosinophilic Esophagitis: Similarities and Differences", Allergy, 67(4):477-490.
Strausberg et al. (2002) "Reading the Molecular Signatures of Cancer", Microarrays and Cancer Research, 11-16.
Suire et al. (Apr. 2005) "p84, a New Gβγ-activated Regulatory Subunit of the Type IB Phosphoinositide 3-kinase p110γ", Current Biology, 15(6):566-570.
Svensson et al. (Apr. 2005) "Human Eosinophils Selectively Recognize and Become Activated by Bacteria Belonging to Different Taxonomic Groups", Microbes and Infection, 7(4):720-728.
Talley et al. (Jan. 1990) "Eosinophilic Gastroenteritis: A Clinicopathological Study of Patients with Disease of the Mucosa, Muscle Layer, and Subserosal Tissues", Gut, 31(1):54-58.
Tan et al. (Mar. 15, 2011) "HYAL1 Overexpression is Correlated with the Malignant Behavior of Human Breast Cancer", International Journal of Cancer, 128(6):1303-1315.
Tezza et al. (Jun. 2013) "Epigenetics of Allergy", Early Human Development, 89(Suppl 1):S20-S21.
Tian et al. (Oct. 1, 2010) "Visualizing of the Cellular Uptake and Intracellular Trafficking of Exosomes by Live-cell Microscopy", Journal of Cellular Biochemistry, 111(2):488-496.
Tkachuk et al. (Nov. 19, 1996) "Regulation and Role of Urokinase Plasminogen Activator in Vascular Remodelling", Clinical and Experimental Pharmacology and Physiology, 23(9):759-765.
Trapnell et al. (Apr. 2009) "TopHat: Discovering Splice Junctions with RNA-Seq", Bioinformatics, 25(9):1105-1111.
Trapnell et al. (May 2010) "Transcript Assembly and Quantification By RNA-seq Reveals Unannotated Transcripts and Isoform Switching During Cell Differentiation", Nature Biotechnology, 28(5):511-515.
Tsang et al. (Mar. 2010) "Oncofetal H19-derived MIR-675 Regulates Tumor Suppressor RB In Human Colorectal Cance", Carcinogenesis, 31(3):350-358.
Tsuchiya et al. (Jan. 7, 2011) "MicroRNA-210 Regulates Cancer Cell Proliferation through Targeting Fibroblast Growth Factor Receptor-like 1 (FGFRLI)", Journal of Biological Chemistry, 286(1):420-428.
Tsukamoto et al. (Mar. 15, 2010) "MicroRNA-375 is Downregulated in Gastric Carcinomas and Regulates Cell Survival by Targeting PDK1 and 14-3-3ζ", Cancer Research, 70(6):2339-2349.
Tzvetkov et al. (Jul. 5, 2013) "Morphine is a substrate of the organic cation transporter OCT1 and polymorphisms in OCT1 gene affect morphine pharmacokinetics after codeine administration", Biochemical Pharmacology, 86(5):666-678.
Ueda et al. (Jun. 6, 2005) "Inflammation and the Reciprocal Production of Granulocytes and Lymphocytes in Bone Marrow", Journal of Experimental Medicine, 201(11):1771-1780.
Vaishnavi et al. (2013) "Oncogenic and Drug-Sensitive NTRK1 Rearrangements in Lung Cancer", Nature Medicine, 19(11):1469-1472.
Valadi et al. (Jun. 2007) "Exosome-Mediated Transfer of mRNA and microRNA is a Novel Mechanism of Genetic Exchange Between Cells", Nature Cell Biology, 9(6):654-659.
Van Rooij et al. (Feb. 3, 2012) "Developing microRNA Therapeutics", Circulation Research, 110(3):496-507.
Vandepapeliere et al. (Jan. 14, 2008) "Vaccine Adjuvant Systems Containing Monophosphoryl Lipid A and QS21 Induce Strong C63 and Persistent Humoral and T Cell Responses Against Hepatitis B Surface Antigen in Healthy Adult Volunteers", Vaccine, 33(8):1084-1091.
Varnes et al. (Apr. 5, 2004) "Discovery of N-propylurea 3-benzylpiperidines as Selective CC Chemokine Receptor-3 (CCR3) Antagonists", Bioorganic & Medicinal Chemistry Letters, 14(7):1645-1649.
Velasco et al. (Mar. 2005) "Toll-like Receptor 4 or 2 Agonists Decrease Allergic Inflammation", American Journal of Respiratory Cell and Molecular Biology, 32(3):218-224.
Velu et al. (May 7, 2009) "Gfi1 Regulates miR-21 and miR-196b to Control Myelopoiesis", Blood, 113(19):4720-4728.
Venek et al. (2014) "Adolescent Suicidal Risk Assessment in Clinician-Patient Interaction: A Study of Verbal and Acoustic Behaviors", Spoken Language Technology Workshop, 6 pages.
Venge Per (May 2010) "The Eosinophil and Airway Remodelling in Asthma", The Clinical Respiratory Journal, 4 (Suppl 1):15-19.
Venkatasubramanian et al. (Jul. 2014) "ABCC3 and OCT1 genotypes influence pharmacokinetics of morphine in children", Pharmacogenomics, 15(10):1297-1309.
Verspoor et al. (Jun. 15, 2009) "The textual characteristics of traditional and Open Access scientific journals are similar", BMC Bioinformatics, 10:183.
Abonia, J. et al. (2010). "Involvement of mast cells in eosinophil esophagitis." Journal of Allergy and Clinical Immunology 126(1):140-149.
Armour, K. et al. (2010). "Expression of human FcγRIIIa as a GPI-linked molecule in CHO cells to enable measurement of human IgG binding." Journal of Immunological Methods 354:20-33.
Aune, T. et al. (2009). "Epigenetics and T helper 1 differentiation." Immunology 126:299-305.
Blanchard, C. et al. (2005). "Inhibition of human interleukin-13-induced respiratory and oesophagael inflammation by anti-human-interleukin-13 antibody (CAT-354)." Clinical & Experimental Allergy 35:1096-1103.
Blanchard, C. et al. (2010). "A striking local esophageal cytokine expression profile in eosinophil esophagitis." Journal of Allergy & Clinical Immunology 127(1):208-224. doi:10.1016j/jaci.2010.10.039.
Caldwell, J. et al. (Feb. 2011). "Global gene expression profile analysis in eosinophilic gastritis identifies CDH26." Journal of Allergy & Clinical Immunology AB216 Abstract 831.
Extended European Search Report mailed Feb. 13, 2015 for European Application No. EP12802640, filed on Dec. 27, 2012.
Faubion, W. et al. (1998). "Treatment of eosinophilic esophagitis with inhaled corticosteroids." Journal of Pediatric Gastroenterology and Nutrition 27:90-93.
Garrett. J. et al. (Jan. 2004). "Anti-interleukin-5 (mepolizumab) therapy for hypereosinophilic syndromes." Journal of Allergy and Clinical Immunology 113(1):115-119.
Hogan, S et al. (2004). "Review article: the eosinophil as a therapeutic target in gastrointestinal disease." Alimentary Pharmacology &Therapeutics 20:1231-1240.
International Preliminary Report on Patentability issued on Nov. 6, 2007 for International Application No. PCT/US2006/016948, filed on May 3, 2006.
International Search Report mailed on Nov. 9, 2006 for International Application No. PCT/US2005/044456, filed Jul. 12, 2005.
International Search Report mailed on Dec. 27, 2012 for International Application No. PCT/US2012/043640, filed Jun. 21, 2012.
International Search Report mailed on Mar. 25, 2013 for International Application No. PCT/US2012/044061, filed Jun. 25, 2012.
International Search Report mailed on Jul. 8, 2019 for International Application No. PCT/US2019/028076, filed Apr. 18, 2019.

(56) References Cited

OTHER PUBLICATIONS

Komiya, A. et al. (2003). "Concerted expression of eotaxin-1, eotaxin-2, and eotaxin-3 in human bronchial epithelial cells." Cellular Immunology 225:91-100.
Mishra, A. et al. (2001). "An etiological role for aeroallergens and eosinophils in experimental esophagitis." Journal of Clinical Investigation 107:83-90.
Ramirez, F. et al. (2006). "Transcriptional regulation of the human alpha2(1) collagen gene (COL1A2), an informative model system to study fibrotic diseases." Matrix Biology 25:365-372.
Raychaudhuri, S. et al. (2000). "Principal components analysis to summarize microarray experiments: application to sporulation time series." Pacific Symposium on Biocomputing vol. 5:452-463.
Rochman, I. et al. (2007). "Cutting edge: Direct action of thymic stromal lymphopoeitin on activated human CD4+ T cells." The Journal of Immunology 178:6720-6724.
Romani, M. et al. (Jul. 9, 2002). "Cluster analysis of gene expression dynamics." Proceedings of the National Academy of Sciences 99(14):9121-9126.
Shoda, T. et al. (Jan. 2020). "Molecular, endoscopic, histologic, and circulating biomarker-based diagnosis of eosinophilic gastritis: Multisite study." Journal of Allergy and Clinical Immunology 145(1):255-269.
Teitelbaum, J. et al. (2002). "Eosinophilic esophagitis in children: Immunopathological analysis and response to fluticasone propionate." Gastroenterology 122:1216-1225.
Todorov, H. et al. (2018). "Principal components analysis: Theory and applicaiton to gene expression data analysis." Genomics and Computational Biology vol. 4(2):e100041.
Collins et al. 2017. Dis Esophagus 30:1-8.
Wen et al. 2014. Journ. Of Aller. And Clin. Immuno. 135(1):187-197.
Wang et al. 1994. J. Immuno. 152(10):5014-5021. [abstract only].
Transcription Profiling of Drosophila 40 Homozygous Raleigh Lines to Understand the Genetic Basis of Complex Traits in *Drosophila*, Accession of No. E-MEXP-1594.
Chu et al. 2011. Nature Immuno, 12(2):151-159.
Elsner et al. 1997. Euro. J. of Immuno. Vol. 27, pp. 2892-2898.
GeneSpring User Manual, version 6.1. Silicon Genetics. Nov. 14, 2003.
Sinicropi et al., BioMEMS and biomedical nanotechnology. Springer US, 2006. 23-46.
Li et al. 2011, J. Biomed. Sci. 2011. pp. 24, vol. 18.
"Rs77569859", Dec. 16, 2010, pp. 1-2, Retrieved from the Internet: URL: http://www.ncbi.nlm.nih.gov/projects/SNP/snp-SS.cgi?subsnp_id=276404309.
"Rs2898261", Dec. 16, 2010, pp. 1-2, Retrieved from the Internet: URL: http://www.ncbi.nlm.nih.gov/projects/SNP/snp-SS.cgi?subsnp_id=279682708.
"Rs8041227", Dec. 16, 2010, pp. 1-2, Retrieved from the Internet: URL: http://www.ncbi.nlm.nih.gov/projects/SNP/snp-SS.cgi?subsnp_id=90109558.
Descamps et al., Cancer Res. 61, 4337-4340 (2001).
Madhusudan et al. Resent Results Cancer Res. 172:25-44.
Prakash et al. Expert Rev. Resp. Med. 4(3), 395-411 (2010).
Oyoshi Current Opinion in Pediatrics, 2015, 27(6), 741-747.
Chen et al. Jiepoukexue Jinzhan (2007), 13(4), 388-391.
Rochlitzer et al. Biochem Soc. Trans (2006), 34(4), 594-599.
Nassenstein et al. J. Allergy Clin. Immuno. 2006; 118:597-605.
Weber et al. Experimental Dermatology, 2014. vol. 23, pp. 1-52.
European Search Report and Written Opinion, 12732079.4 Apr. 22, 2014, 11 pages.
Recombinant Mouse N-Cadherin Fc Chimera Protein, Cf 6626-NC . . . https://www.rndsysytems.com> N-Cadherin Jan. 14, 2011—Mouse N-Caderin protein (6626-NC) is manufactured by R&D Systems. Retrieved Aug. 15, 2018.
Recombinant Human VE-Cadherin Fc Chimera Protein, CF . . . https://www.rndsysytems.com> N-Cadherin Jul. 4, 2015—Huamn VW-Caderin protein (938-VC) is manufactured by R&D Systems. Retrieved Aug. 15, 2018.

International Search Report and Written Opinion for Application No. PCT/US2016/068236, mailed Dec. 22, 2016.
Valeska et al. Gastroenterology. 156(6, Suppl. 1) S619. 1 page—2019.
Vicario et al. (Jan. 2010) "Local B Cells and IgE Production in the Oesophageal Mucosa in Eosinophilic Desophagitis", Gut, 59(1):12-20.
Vincent et al. (Dec. 2, 2009) "International Study of the Prevalence and Outcomes of Infection in Intensive Care Units", JAMA, 302(21):2323-2329.
Von Ahlfen et al. (2007) "Determinants of RNA Quality from FFPE Samples", PLoS One, e1261, 2(12):7 pages.
Von Arnim et al. (2014) "Eosinophilic Esophagitis—Treatment of Eosinophilic Esophagitis with Drugs: Corticosteroids", Digestive Diseases, 32(1-2):126-129.
Wacker et al. (Jul. 8, 2002) "CCR3 Antagonists: A Potential New Therapy for the Treatment of Asthma. Discovery and Structure-activity Relationships", Bioorganic & Medicinal Chemistry Letters, 12(13):1785-1789.
Wan et al. (Feb. 2004) "Foxa2 Regulates Alveolarization and Goblet Cell Hyperplasia", Development, 131(4):953-964.
Wang et al. (May 2010) "Differential Functions of Growth Factor Receptor-Bound Protein 7 (GRB7) and Its Variant GRB7v in Ovarian Carcinogenesis", Clinical Cancer Research, 16(9):2529-2539.
Yee et al. (Jul. 3, 2012) "Insulin-like Growth Factor Receptor Inhibitors: Baby or the Bathwater?", Journal of the National Cancer Institute, 104(13):975-981.
Yang et al. (May 2009) "Th17 And Natural Treg Cell Population Dynamics in Systemic Lupus Erythematosus", Arthritis & Rheumatology, 60(5);1472-1483.
Wechsler et al. (Jul. 2018) "Esophagitis Reference Score Accurately Identifies Disease Activity and Treatment Effects in Children", Clinical Gastroenterology and Hepatology, 16(7):1056-1063.
Wen et al. (Aug. 23, 2013) "Molecular diagnosis of eosinophilic esophagitis by gene expression profiling", Gastroenterology, 145(6):19 Pages.
Wen et al. (Oct. 19, 2014) "Transcriptome analysis of proton pump inhibitor-responsive esophageal eosinophilia reveals proton pump inhibitor-reversible allergic inflammation", Journal of Allergy and Clinical Immunology, 135(1):187-197.
White (Nov. 24, 2000) "Identification of Potent, Selective Nonpeptide CC Chemokine Receptor-3 Antagonist that Inhibits Eotaxin-, Eotaxin-2-, and Monocyte Chemotactic Protein-4-induced Eosinophil Migration", The Journal of Biological Chemistry, 275(47):36626-36631.
Wills-Karp Marsha (Dec. 2004) "Interleukin-13 in Asthma Pathogenesis", Immunological Reviews, 202:175-190.
Winter et al. (Mar. 2009) "Many Roads to Maturity: microRNA Biogenesis Pathways and their Regulation", Nature Cell Biology, 11(3):228-234.
Wolska et al. (Apr. 2009) "The Role of Toll-Like Receptors in Hematopoietic Malignancies", Current Molecular Medicine, 9(3):324-335.
Wong et al. (Jul. 2007) "Intracellular Signaling Mechanisms Regulating Toll-like Receptor-mediated Activation of Eosinophils", American Journal of Respiratory Cell and Molecular Biology, 37(1):85-96.
Wong et al. (Feb. 2013) "Microrna-21* Regulates the Prosurvival Effect of GM-CSF on Human Eosinophils", Immunobiology, 218(2):255-262.
Woodruff et al. (Oct. 2, 2007) "Genome-wide Profiling Identifies Epithelial Cell Genes Associated with Asthma and With Treatment Response to Corticosteroids", Proceedings of the National Academy of Sciences of the United States of America, 10(40):15858-15863.
Wu et al. (Nov. 2008) "MicroRNAs Are Differentially Expressed in Ulcerative Colitis and Alter Expression of Macrophage Inflammatory Peptide-2a", Gastroenterology, e24, 135(5):1624-1635.
Kanthou Marietta (Sep. 2008) "Leucocyte Blood Picture in III Newborn Babies", Archives of Disease in Childhood, 47(255):741-746.

(56) References Cited

OTHER PUBLICATIONS

Xiang et al. (Feb. 15, 2008) "Wound Repair and Proliferation of Bronchial Epithelial Cells Regulated by CTNNAL 1", Journal of Cellular Biochemistry, 103(3):920-930.
Xing et al. (Aug. 23, 2011) "Protease Phenotype of Constitutive Connective Tissue and of Induced Mucosal Mast Cells in Mice Is Regulated by the Tissue", Proceedings of the National Academy of Sciences of the United States of America, 108(34):4210-1421.
Yamazaki et al. (Nov. 2006) "Allergen-specific In Vitro Cytokine Production in Adult Patients with Eosinophilic Esophagitis", Digestive Diseases and Sciences, 51(11):1934-1941.
Yang et al. (Oct. 15, 2006) "Inhibition of Arginase I Activity by RNA Interference Attenuates IL-13-Induced Airways Hyperresponsiveness", The Journal of Immunology, 177(8):5595-5603.
Kalinin et al; Future Medicine, vol. 19, pp. 629-650, 2018.
Siddique et al; Human Pathology, vol. 68, pp. 79-86, 2017.
Butz et al; Gastroenterology, vol. 147, pp. 324-333, 2014.
Caldwell J.M. J Allergy Clin Immunol. 134:1114-24 (2014).
Eisen et al. 1998 Proc. Natl. Acad. Sci. USA (25)95, p. 14863-14868.
Shoda et al., Lancet Gastroenterol Hepatol. Jul. 2018; 3(7):477-488; Epub May 3, 2018. PubMed PMID: 29730081
Sato et al., J Allergy Clin Immunol Pract. Nov.-Dec. 2017; 5(6):1639-1649.e2. Epub May 16, 2017.
Mayoral et al. (Jan. 1, 2009) "MicroRNA-221-222 Regulate the Cell-Cycle in Mast Cells", Journal of Immunology, 182(1):433-445.
McGettrick et al. (Sep. 25, 2007) "Toll-like Receptors: Key Activators of Leucocytes and Regulator of Haematopoiesis", British Journal of Haematology, 139(2):185-193.
Medina et al. (Sep. 2, 2010) "OncomiR Addiction in an in Vivo Model Of microRNA-21-induced Pre-β-cell Lymphoma", Nature, 467(7311):86-90.
Meineke et al. (Dec. 2002) "Pharmacokinetic modelling of morphine, morphine-3- glucuronide and morphine-6-glucuronide in plasma and cerebrospinal fluid of neurosurgical patients after short-term infusion of morphine", British Journal of Clinical Pharmacology, 54(6):592-603.
Menard-Katcher et al. (2012) "MicroRNAs are Altered in Eosinophilic Esophagitis", Gastroenterology, 142(5)8440.
Menzies-Gow et al. (Apr. 2003) "Anti-IL-5 (Mepolizumab) Therapy Induces Bone Marrow Eosinophil Maturational Arrest and Decreases Eosinophil Progenitors in the Bronchial Mucosa of Atopic Asthmatics", The Journal of Allergy and Clinical Immunology, 111(4):714-719.
Meyer et al. (Jan. 2013) "The UCSC Genome Browser database: Extensions and Updates 2013", Nucleic Acids Research, 41:D64-D69.
Michael et al. (2005) "Biochemical and Enzymatic Characterization of Human Kallikrein 5 (hK5), a Novel Serine Protease Potentially Involved in Cancer Progression", Journal of Biological Chemistry, 280(15):14628-35.
Michaels et al. (Feb. 5-11, 2005) "Prediction of Cancer Outcome with Microarrays: A Multiple Random Validation Strategy", Lancet, 365(9458):488-492.
Milbrandt J. (Nov. 6, 1987) "A Nerve Growth Factor-induced Gene Encodes a Possible Transcriptional Regulatory Factor", Science, 238(4828):797-799.
Milgrom et al. (Dec. 23, 1999) "Treatment of Allergic Asthma with Monoclonal Anti-IgE Antibody", The New England Journal of Medicine, 341(26):1966-1973.
Mishra et al. (Jan. 2008) "Esophageal Remodeling Develops as a Consequence of Tissue Specific IL-5-induced Eosinophilia", Gastroenterology, 134(1):204-214.
Mishra et al. (Mar. 1, 2002) "IL-5 Promotes Eosinophil Trafficking to the Esophagus", The Journal of Immunology, 168(5):2464-2469.
Mishra et al. (Nov. 2003) "Intratracheal IL-13 Induces Eosinophilic Esophagitis by an IL-5, Eotaxin-1, and STAT6-Dependent Mechanism", Gastroenterology, 125(5)1419-1427.

Mitchell et al. (Jul. 29, 2008) "Circulating microRNAs as Stable Blood-based Markers for Cancer Detection", Proceedings of the National Academy of Sciences of the United States of America, 105(30):10513-10518.
Mizuno et al. (2013) "Genotype of Abcc3-211c > T Influences the Pharmacokinetics of Morphine Glucuronide in Children", Clinical Pharmacology & Therapeutics, 93:S63.
Mogil et al. (Jul. 6, 1999) "The genetic mediation of individual differences in sensitivity to pain and its inhibition", PNAS, 96(14):7744-7751.
Molina-Infante et al. (May 7, 2008) "Overlap of Reflux and Eosinophilic Esophagitis in Two Patients Requiring Different Therapies: A Review of the Literature", World Journal of Gastroenterology, 14(9):1463-1466.
Mori et al. (Jan. 16, 2009) "Identification of the Human Eosinophil Lineage-committed Progenitor: Revision of Phenotypic Definition of the Human Common Myeloid Progenitor", Journal of Experimental Medicine, 206(1):183-193.
Mukhopadhyay et al. (Jul. 2010) "Matrix Metalloproteinase-12 is a Therapeutic Target for Asthma in Children and Young Adults", The Journal of Allergy and Clinical Immunology, 126(1):70-76.
Mulder et al. (Jan. 12, 2011) "Understanding Eosinophilic Esophagitis: The Cellular and Molecular Mechanisms of an Emerging Disease", Mucosal Immunology, 4(2):139-147.
Murata et al. (Jul. 2008) "Activation of Toll-like Receptor 2 by a Novel Preparation of Cell Wall Skeleton from *Mycobacterium bovis* BCG Tokyo (SMP-105) Sufficiently Enhances Immune Responses Against Tumors", Cancer Science, 99(7):1435-1440.
Nagai et al. (Jun. 2006) "Toll-like Receptors on Hematopoietic Progenitor Cells Stimulate Innate Immune System Replenishment", Immunity, 24(6):801-812.
Nagase et al. (Oct. 15, 2003) "Expression and Function of Toll-like Receptors in Eosinophils: Activation by Toll-like Receptor 7 Ligand", Journal of Immunology, 171(8):3977-3982.
Navarro et al. (Jun. 1, 2010) "Small RNAs Guide Hematopoietic Cell Differentiation and Function", Journal of Immunology, 184(11):5939-5947.
Naya et al. (May 7, 2001) "Discovery of a Novel CCR3 Selective Antagonist", Bioorganic & Medicinal Chemistry Letters, 11(9):1219-1223.
Naya et al. (Jun. 2003) "Structure-Activity Relationships of 2-(Benzothiazolylthio)acetamide Class of CCR3 Selective Antagonist", Chemical and Pharmaceutical Bulletin, 51(6):697-701.
Newberry et al. (Nov. 2005) "Strongyloides Hyperinfection Presenting As Acute Respiratory Failure And Gram-negative Sepsis", Chest, 128(5):3681-3684.
Noel et al. (Jul. 2004) "Clinical and Immunopathologic Effects of Swallowed Fluticasone for Eosinophilic Esophagitis", Clinical Gastroenterology and Hepatology, 2(7):568-575.
Notterman et al. (2002) "Tumor Biology and Microarray Analysis of Solid Tumors: Colorectal Cancer as a Model System", Microarrays and Cancer Research, 81-111.
Novak et al. (Apr. 1, 2007) "CCL23 Expression Is Induced by IL-4 in a STAT6-Dependent Fashion", Journal of Immunology, 178(7):4335-4341.
Ogbogu et al. (Dec. 2009) "Hypereosinophilic Syndromes: A Multicenter, Retrospective Analysis of Clinical Characteristics and Response to Therapy", The Journal of Allergy and Clinical Immunology, 124(6):1319-1325.
Ordoñez et al. (Dec. 2000) "Epithelial Desquamation in Asthma", American Journal of Respiratory and Critical Care Medicine, 162(6):2324-2329.
Ozawa et al. (Oct. 2009) "BRAK/CXCL14 Expression Oral Carcinoma Cells Completely Suppresses Tumor Cell Xenografts in SCID Mouse", Biomedical Research, 30(5):315-318.
Ozawa et al. (Oct. 11, 2009) "Restoration of BRAK/CXCL14 Gene Expression by Gefitinib is Associated with Antitumor Efficacy of the Drug in Head and Neck Squamous Cell Carcinoma", Cancer Science, 100(11):2202-2209.
Ozdas et al. (Sep. 2004) "Investigation of Vocal Jitter and Glottal Flow Spectrum as Possible Cues for Depression and Near-Term Suicidal Risk", Transactions on Biomedical Engineering, 51(9):1530-1540.

(56) References Cited

OTHER PUBLICATIONS

Papagiannakopoulos et al. (Oct. 1, 2008) "MicroRNA-21 Targets a Network of Key Tumor-Suppressive Pathways in Glioblastoma Cells", Cancer Research, 68(19):8164-8172.
Park et al. (Dec. 27, 2006) "Genetic polymorphisms in the ABCB1 gene and the effects of fentanyl in Koreans", Clinical Pharmacology & Therapeutics, 81(4):539-546.
Patent Cooperation Treaty, International Preliminary Report on Patentability and Written Opinion in corresponding International application No. PCT/US2012/044061, mailed on Dec. 23, 2013, 7 pages.
International Search Report for International Application No. PCT/US2015/044461 mailed on Nov. 9, 2015, 11 pages.
Peeters et al. (Apr. 8, 2005) "Real-time RT-PCR Quantification of mRNA Encoding Cytokines and Chemokines in Histologically Normal Canine Nasal, Bronchial and Pulmonary Tissue", Veterinary Immunology and Immunopathology, 104(3-4):195-204.
Persson et al. (Jun. 2001) "Bactericidal Activity of Human Eosinophilic Granulocytes Against *Escherichia coli*", Infection and Immunity, 69(6):3591-3596.
Petriv et al. (Aug. 31, 2010) "Comprehensive MicroRNA Expression Profiling of the Hematopoietic Hierarchy", Proceedings of the National Academy of Sciences of the United States of America, 107(35):15443-15448.
Phipps et al. (Sep. 1, 2007) "Eosinophils Contribute to Innate Antiviral Immunity and Promote Clearance of Respiratory Syncytial Virus", Blood, 110(5):1578-1586.
Plötz et al. (Jan. 1, 2001) "The Interaction of Human Peripheral Blood Eosinophils with Bacterial ipopolysaccharide is CD14 Dependent", Blood, 97(1):235-241.
Polikepahad et al. (Sep. 24, 2010) "Proinflammatory Role for let-7 MicroRNAS in Experimental Asthma", Journal of Biological Chemistry, 285(39):30139-30149.
Pouladi et al. (Jan. 2004) "Interleukin-13-dependent Expression of Matrix Metalloproteinase-12 is Required for the Development of Airway Eosinophilia in Mice", American Journal of Respiratory Cell and Molecular Biology, 30(1):84-90.
Proudfoot et al. (Nov. 5, 1999) "Amino-terminally Modified RANTES Analogues Demonstrate Differential Effects on RANTES Receptors", Journal of Biological Chemistry, 274(45):32478-32485.
Prows et al. (Nov. 13, 2013) "Codeine-related adverse drug reactions in children following tonsillectomy: a prospective study", Laryngoscope, 124(5):1242-1250.
Prussin et al. (Dec. 2009) "Eosinophilic Gastrointestinal Disease and Peanut Allergy are Alternatively Associated with IL-5+ and IL-5(−) T(H)2 Responses", The Journal of Allergy and Clinical Immunology, 124(6):1326-1332.
Dellon, Evan S et al. "Esophageal dilation in eosinophilic esophagitis: safety and predictors of clinical response and complications." Gastrointestinal endoscopy vol. 71,4 (2010): 706-12. doi:10.1016/j.gie.2009.10.047.
Molina-Infante et al., 2016—"Proton pump inhibitor-responsive oesophageal eosinophilia: an entity challenging current diagnostic criteria for eosinophilic oesophagitis" Gut—65:524-531.
Gong et al. (May 30, 2013) "Gene polymorphisms of OPRM1 A118G and ABCB1 C3435T may influence opioid requirements in Chinese patients with cancer pain", Asian Pacific Journal of Cancer Prevention, 14(5):2937-2943.
Gonsalves et al. (Jan. 2020) "Diagnosis and Treatment of Eosinophilic Esophagitis", The Journal of Allergy and Clinical Immunology, 145(1):1-7.
Gonsalves et al. (Sep. 2006) "Histopathologic Variability and Endoscopic Correlates in Adults with Eosinophilic Esophagitis", Gastrointestinal Endoscopy, 64(3):313-319.
Griffiths-Jones et al. (2006) "miRBase: MicroRNA Sequences, Targets and Gene Nomenclature", Nucleic Acids Research, 34:D140-D144.
Griffiths-Jones et al. (Jan. 2008) "miRNAse: Tools for Micro RNA Genomics", Nucleic Acids Research, 36 (Database issue):D154-D158.

Gupta et al. (Jan. 2006) "Cytokine Expression in Normal and Inflamed Esophageal Mucosa: A Study into the Pathogenesis of Allergic Eosinophilic Esophagitis", Journal of Pediatric Gastroenterology and Nutrition:, 42(1):22-26.
Gupta et al. (May 1998) "Expression of Inducible Nitric Oxide Synthase (iNOS) mRNA in Inflamed Esophageal and Colonic Mucosa in a Pediatric Population", American Journal of Gastroenterology, 93(5):795-798.
Guyon et al. (Jan. 2002) "Gene Selection for Cancer Classification using Support Vector Machines", Machine Learning, 46:389-422.
Hahn et al. (Apr. 2006) "Airway Epithelial Cells Produce Neurotrophins and Promote the Survival of Eosinophils During Allergic Airway Inflammation", Journal of Allergy and Clinical Immunology, 117(4):787-794.
Hamilton et al. (1980) "Regulation of The Plasminogen Activator Activity of Macrophage Tumor Cell Lines", International Journal of Immunopharmacology, 2(4):353-362.
Hamoui et al. (Aug. 2004) "Increased Acid Exposure in Patients With Gastroesophageal Reflux Disease Influences Cyclooxygenase-2 Gene Expression in the Squamous Epithelium of the Lower Esophagus", Archives of Surgery, 139 (7):712-716.
Hardiman Gary (Nov. 5, 2004) "Microarray Platforms—Comparisons and Contrasts", Pharmacogenomics, 5(5):487-502.
Hatley et al. (Sep. 14, 2010) "Modulation of K-Ras-dependent Lung Tumorigenesis by MicroRNA-21", Cancer Cell, 18(3):282-293.
Heib et al. (May 2019) "Wheat Amylase/Trypsin Inhibitors Aggravate Eosinophilic Esophagitis", Gastroenterology, 6 (Suppl. 1):1 page.
Hennessy et al. (Apr. 2010) "Targeting Toll-Like Receptors: Emerging Therapeutics?", Nature Reviews Drug Discovery, 9(4):293-307.
Himes et al. (Mar. 4, 2009) "Prediction of Chronic Obstructive Pulmonary Disease (COPD) in Asthma Patients Using Electronic Medical Records", Journal of the American Medical Informatics Association, 16(3):371-379.
Hogan et al. (May 2008) "Eosinophils: Biological Properties and Role in Health and Disease", Clinical & Experimental Allergy, 38(5):709-750.
Hotchkiss et al. (Jun. 1, 2001) "Sepsis-induced Apoptosis Causes Progressive Profound Depletion of B and CD4+ T Lymphocytes in Humans", Journal of Immunology, 166(11):6952-6963.
Huang et al. (Jul. 1, 2006) "RegRNA: An Integrated Web Server for Identifying Regulatory RNA Motifs and Elements", Nucleic Acids Research, 34:W429-W434.
Hwang et al. (Apr. 30, 2005) "Expression of IL-17 Homologs and their Receptors in the Synovial Cells of Rheumatoid Arthritis Patients", Molecular Cell, 19(2):180-184.
Indo Y. (Dec. 2001) "Molecular Basis of Congenital Insensitivity to Pain with Anhidrosis (CIPA): Mutations and Polymorphisms in Trka (NTRK1) Gene Encoding the Receptor Tyrosine Kinase for Nerve Qrowth Factor", Human Mutation, 18(6):462-471.
Indo et al. (Aug. 1996) "Mutations in the TRKA/NGF Receptor Gene in Patients with Congenital Insensitivity to Pain with Anhidrosis", Nature Genetics, 13(4):485-488.
Indo Y. (Oct. 2012) "Nerve Growth Factor and the Physiology of Pain: Lessons from Congenital Insensitivity to Pain with Anhidrosis", Clinical Genetics, 82(4):341-350.
Ip et al. (Dec. 2007) "Interleukin-31 Induces Cytokine and Chemokine Production from Human Bronchial Epithelial Cells through Activation of Mitogen-activated Protein Kinase Signalling Pathways: Implications for the Allergic Response", Immunology, 122(4):532-541.
Iwasaki et al. (Jun. 20, 2005) "Identification of Eosinophil Lineage-committed Progenitors in the Murine Bone Marrow", Journal of Experimental Medicine, 201(12):1891-1897.
Jacobsen et al. (Jun. 2007) "Eosinophils: Singularly Destructive Effector Cells or Purveyors of Immunoregulation?", The Journal of Allergy and Clinical Immunology, 119(6):1313-1320.
Jakiela et al. (Oct. 2009) "Intrinsic Pathway of Apoptosis in Peripheral Blood Eosinophils of Churg-strauss Syndrome", Rheumatology (Oxford), 48(10):1202-1207.
Jia et al. (Nov. 2008) "Mist1 Regulates Pancreatic Acinar Cell Proliferation through p21 CIP1/WAF1", Gastroenterology, 135(5):1687-1697.

(56) References Cited

OTHER PUBLICATIONS

Jiang et al. (Jul. 2011) "The Emerging Role of MicroRNAs in Asthma", Molecular and Cellular Biochemistry, 353(1-2):35-40.
Johnnidis et al. (Feb. 28, 2008) "Regulation of Progenitor Cell Proliferation and Granulocyte Function by MicroRNA-223", Nature, 451:1125-1129.
Juffali et al. (2010) "The WiNAM project: Neural data analysis with applications to epilespy", Biomedical Circuits and Systems Conference, 45-48.
Junttila et al. (Oct. 27, 2008) "Tuning Sensitivity to IL-4 and IL-13: Differential Expression of IL-4Ralpha, IL-13Ralpha1, and Gammac Regulates Relative Cytokine Sensitivity", Journal of Experimental Medicine, 205(11):2595-2608.
Kaiko et al. (Feb. 2011) "New Insights into the Generation of Th2 Immunity and Potential Therapeutic Targets for the Treatment of Asthma", Current Opinion in Allergy and Clinical Immunology, 11(1):39-45.
Kaimal et al. (Jul. 2010) "Toppcluster: A Multiple Gene List Feature Analyzer for Comparative Enrichment Clustering and Network-based Dissection of Biological System", Nucleic Acids Research, 38:W96-W102.
Kanzler et al. (May 3, 2007) "Therapeutic Targeting of Innate Immunity with Toll-like Receptor Agonists and Antagonists", Nature Medicine, 13(5):552-559.
Kariyawasam et al. (Sep. 2009) "Activin and Transforming Growth Factor-β Signaling Pathways are Activated after Allergen Challenge in Mild Asthma", The Journal of Allergy and Clinical Immunology, 124(3):454-462.
Kaur et al. (Jul. 1, 2002) "Rofecoxib Inhibits Cyclooxygenase 2 Expression and Activity and Reduces Cell Proliferation in Barrett's Esophagus", Gastroenterology, 123(1):60-67.
Kelly et al. (Apr. 9, 2012) "More codeine fatalities after tonsillectomy in North American children", Pediatrics, 129(5):e1343-1347.
Kerstjens et al. (Oct. 2019) "Airway Pharmacology: Treatment Options and Algorithms to Treat Patients with Chronic Obstructive Pulmonary Disease", Journal of Thoracic Disease, 11(S17):S2200-S2209.
Kihara et al. (Sep. 1, 2001) "Prediction of Sensitivity of Esophageal Tumors to Adjuvant Chemotherapy by cDNA Microarray Analysis of Gene-expression Profiles", Cancer Research, 61(17):6474-6479.
Kim et al. (2004) "Microarray Applications in Cancer Research", Cancer Research and Treatment, 36(4):207-213.
Kim et al. (Dec. 2004) "Rebound Eosinophilia after Treatment of Hypereosinophilic Syndrome and Eosinophilic Gastroenteritis with Monoclonal Anti-IL-5 Antibody SCH55700", The Journal of Allergy and Clinical Immunology, 114(6):1449-1455.
Kledal et al. (Sep. 12, 1997) "A Broad-Spectrum Chemokine Antagonist Encoded by Kaposi's Sarcoma-Associated Herpesvirus", Science, 277(5332):1656-1659.
Klingelhöfer et al. (Nov. 2002) "Dynamic Interplay Between Adhesive and Lateral E-Cadherin Dimers", Molecular and Cellular Biology, 22(21):7449-7458.
Kong et al. (Jan. 2012) "MicroRNA-375 Inhibits Tumour Growth and Metastasis in Oesophageal Squamous Cell Carcinoma Through Repressing Insulin-like Growth Factor 1 Receptor", Gut., 61(1):33-42.
Konikoff et al. (Nov. 2006) "A Randomized, Double-blind, Placebo-controlled Trial of Fluticasone Propionate for Pediatric Eosinophilic Esophagitis", Gastroenterology, 131(5):1381-1391.
Konturek et al. (Aug. 2004) "Activation of NFKB Represents the Central Event in the Neoplastic Progression Associated with Barrett's Esophagus: A Possible Link to the Inflammation and Overexpression of COX-2, PPARγ and Growth Factors", Digestive Diseases and Sciences, 49(7-8):1075-1083.
Kottyan et al. (Jul. 13, 2014) "Genome-wide Association Analysis of Eosinophilic Esophagitis Provides Insight into the Tissue Specificity of this Allergic Disease", Nature Genetics, 46(8):895-900.
Kouro et al. (Dec. 2009) "IL-5- and Eosinophil-mediated Inflammation: From Discovery to Therapy", International Immunology, 21(12):1303-1309.

Krichevsky et al. (Jan. 2009) "MIR-21: A Small Multi-faceted RNA", Journal of Cellular and Molecular Medicine, 13(1):39-53.
Yuan et al. (Feb. 7, 2011) "Microrna-203 Inhibits Cell Proliferation by Repressing Anp63 Expression in Human Esophageal Squamous Cell Carcinoma", BMC Cancer, 11:10 pages.
Yousefi et al. (Aug. 10, 2008) "Catapult-like Release of Mitochondrial DNA by Eosinophils Contributes to Antibacterial Defense", Nature Medicine, 14(9):949-953.
Raap et al. (Feb. 2010) "The Role of Neurotrophins in the Pathophysiology of Allergic Rhinitis", Current Opinion in Allergy and Clinical Immunology, 10(1):8-13.
Rabinowits et al. (Jan. 2009) "Exosomal microRNA: a Diagnostic Marker for Lung Cancer", Clinical Lung Cancer, 10(1):42-46.
Rahaghi et al. (2017) "Long-term Clinical Outcomes Following Treatment with Alpha 1-Proteinase Inhibitor for COPD associated with alpha-1 Antitrypsin Deficiency: A Look at the Evidence", Respiratory Research, 18(1):9 Pages.
Zuo et al. (Jul. 1, 2010) "IL-13 Induces Esophageal Remodeling and Gene Expression by an Eosinophil-Independent, L-13Ra2-Inhibited Pathway", The Journal of Immunology, 185(1):660-669.
Ramirez et al. (Dec. 15, 2004) "Immortalization of Human Bronchial Epithelial Cells in the Absence of Viral Oncoproteins", Cancer Research, 64(24):9027-9034.
Rank et al. (May 2020) "Technical Review on the Management of Eosinophilic Esophagitis: A Report from the AGA Institute and the Joint Task Force on Allergy-immunology Practice Parameters", Annals of Allergy, Asthma & Immunology, e17, 124(5):424-440.
Ray et al. (May 16, 2011) "Human Mu Opioid Receptor (OPRM1 a 118G) polymorphism is associated with brain mu-opioid receptor binding potential in smokers", PNAS, 108(22):9268-9273.
Robinson et al. (Jan. 1999) "CD34(+)/Interleukin-5Ralpha Messenger RNA+ Cells in the Bronchial Mucosa in Asthma: Potential Airway Eosinophil Progenitors", American Journal of Respiratory Cell and Molecular Biology, 20(1):9-13.
Rochman et al. (Jul. 2015) "Neurotrophic Tyrosine Kinase Receptor 1 is a Direct Transcriptional and Epigenetic Target of IL-13 Involved in Allergic Inflammation", Immunology, 8(4):785-798.
Rodrigo et al. (Feb. 2008) "High Intraepithelial Eosinophil Counts in Esophageal Squamous Epithelium Are Not Specific for Eosinophilic Esophagitis in Adults", The American Journal of Gastroenterology, 103(2);435-442.
Rosas et al. (Jul. 2006) "IL-5-mediated Eosinophil Survival Requires Inhibition of GSK-3 and Correlates with β-catenin Relocalization", Journal of Leukocyte Biology, 80(1):186-195.
Rothenberg Marc E. (Oct. 2009) "Biology and Treatment of Eosinophilic Esophagitis", Gastroenterology, 137(4):1238-1249.
Rothenberg et al. (Apr. 2010) "Common Variants at 5q22 Associate with Pediatric Eosinophilic Esophagitis", Nature Genetics, 42(4):289-291.
Rothenberg et al. (Jan. 2004) "Eosinophilic Gastrointestinal Disorders (EGID)", The Journal of Allergy and Clinical ImmunologyThe Journal of Allergy and Clinical Immunology, 113(1):11-28.
Rothenberg (Apr. 21, 2016) "Humanized anti-IL-5 Antibody Therapy", Cell, 165(3):1 page.
Rothenberg et al. (Dec. 2001) "Pathogenesis and Clinical Features of Eosinophilic Esophagitis", The Journal of Allergy and Clinical Immunology, 108(6):891-894.
Rothenberg et al. (Apr. 2010) "The Eosinophil", Annual Review of Immunology, 24:147-174.
Rothenberg et al. (Mar. 20, 2008) "Treatment of Patients with the Hypereosinophilic Syndrome with Mepolizumab", The New England Journal of Medicine, 358(12):1215-1228.
Russ et al. (2013) "T Cell Immunity as a Tool for Studying Epigenetic Regulation of Cellular Differentiation", Frontiers in Genetics, 4:218.
Sabroe et al. (Aug. 25, 2000) "A Small Molecule Antagonist of Chemokine Receptors CCR1 and CCR3", The Journal of Biological Chemistry, 275(34):25985-25992.
Sabroe et al. (May 1, 2002) "Toll-Like Receptor (TLR)2 and TLR4 in Human Peripheral Blood Granulocytes: A Critical Role for Monocytes in Leukocyte Lipopolysaccharide Responses", The Journal of Immunology, 168(9):4701-4710.

(56) References Cited

OTHER PUBLICATIONS

Sadhasivam et al. (2014) "Genetics of pain perception, COMT and postoperative pain management in children", The Pharmacogenomics Journal, 15(3):277-284.
Sadhasivam et al. (Jul.-Aug. 2012) "Morphine clearance in children: does race or genetics matter?", Journal of Opioid Management, 8(4):217-226.
Sadhasivam et al. (2015) "Novel Associations between FAAH Genetic Varients an Postoperative Central Opioid Related Adverse Effects", The Pharmacogenomics Journal, 15(5):436-442.
Sadhasivam et al. (Jun. 13, 2012) "Preventing Opioid-Related Deaths in Children Undergoing Surgery", Pain Medicine, 13(7):982-983.
Sadhasivam et al. (Apr. 23, 2012) "Race and unequal burden of perioperative pain and opioid related adverse effects in children", Pediatrics, 129(5):832-838.
Saeki et al. (Mar. 2, 2001) "Identification of a Potent and Nonpeptidyl CCR3 Antagonist", Biochemical and Biophysical Research Communications, 281(3):779-782.
Sahin et al. (Oct. 2014) "MRNA-Based Therapeutics—Developing a New Class of Drugs", Nature reviews, 13(10):759-780.
Saini et al. (Nov. 27, 2008) "Annotation of Mammalian Primary microRNAs", BMC Genomics, Article No. 564, 9(1):19 pages.
Saito et al. (Mar. 15, 2002) "Pathogenesis of Murine Experimental Allergic Rhinitis: A Study of Local and Systemic Consequences of IL-5 Deficiency", The Journal of Immunology, 168(6):3017-3023.
Sato et al. (May 2011) "MicroRNAs and Epigenetics", The FEBS Journal, 278(10):1598-1609.
Sayed et al. (Jul. 2011) "MicroRNAs in Development and Disease", Physiological Reviews, 91(3):827-887.
Scherer et al. (2013) "Investigating the Speech Characteristics of Suicidal Adolescents", International Conference on Acoustics, Speech and Signal Processing, 5 pages.
Schmid-Grendelmeier et al. (Jul. 15, 2002) "Eosinophils Express Functional IL-13 in Eosinophilic Inflammatory Diseases", Journal of Immunology, 169(2):1021-1027.
Schoneberg et al. (Mar. 2, 2018) "Structural Basis of G Protein-coupled Receptor Function", Molecular and Cellular Endocrinology, 151(1-2):181-193.
Schultz et al. (May 26, 1998) "SMART, A Simple Modular Architecture Research Tool: Identification of Signaling Domains", Proceedings of the National Academy of Sciences of the United States of America, 95(11):5857-5864.
Sehmi et al. (Nov. 15, 1997) "Allergen-induced Increases in IL-5 Receptor Alpha-subunit Expression on Bone Marrow-derived CD34+ Cells from Asthmatic Subjects. A Novel Marker of Progenitor Cell Commitment Towards Eosinophilic Differentiation", Journal of Clinical Investigation, 100(10):2466-2475.
Sexton et al. (Sep. 2009) "Recent Advances in our Understanding of Peptide Hormone Receptors and RAMPS", Current Opinion in Drug Discovery & Development, 2(5):440-448.
Shaaban et al. (Dec. 2010) "Eosinopenia: Is it a Good Marker of Sepsis in Comparison to Procalcitonin and C-reactive Protein Levels for Patients Admitted to a Critical Care Unit in an Urban Hospital?", Journal of Critical Care, 25(4):570-575.
Shah et al. (Mar. 2009) "Histopathologic Variability In Children with Eosinophilic Esophagitis", The American Journal of Gastroenterology, 104(3):716-721.
Sharma et al. (Aug. 5, 2011) "Protein Kinase R as Mediator of the Effects of Interferon (IFN) Gamma and Tumor Necrosis Factor (TNF) Alpha on Normal and Dysplastic Hematopoiesis", Journal of Biological Chemistry, 286 (31):27506-27514.
Shen et al. (Apr. 2011) "Plasma MicroRNAs as Potential Biomarkers for Non-small-cell Lung Cancer", Laboratory Investigation, 91(4):579-587.
Sheng et al. (Jun. 2011) "The MUC13 Cell Surface Mucin Protects Against Intestinal Inflammation by Inhibiting Epithelial Cell Apoptosis", Gut, 60(12):1661-1670.

Sherrill et al. (Jul. 2011) "Genetic Dissection of Eosinophilic Esophagitis Provides Insight into Disease Pathogenesis and Treatment Strategies", The Journal of Allergy and Clinical Immunology, 128(1):23-32.
Sherrill et al. (Jul. 1, 2010) "Variants of Thymic Stromal Lymphopoietin and its Receptor Associate with Eosinophilic Esophagitis", Journal of Allergy and Clinical Immunology, 126(1):160-165.
Shinkai et al. (Aug. 1, 1999) "A Novel Human CC Chemokine, Eotaxin-3, Which Is Expressed in IL-4-Stimulated Vascular Endothelial Cells, Exhibits Potent Activity Toward Eosinophils", The Journal of Immunology, 163(3):1602-1610.
Shinkai et al. (Nov. 2002) "N-terminal Domain of Eotaxin-3 is Important for Activation Of CC Chemokine Receptor 3", Protein Engineering, Design and Selection, 15(11):923-929.
Yin et al. (Jan. 2010) "Targeting the Insulin-like Growth Factor-1 Receptor by Picropodophyllin as a Treatment Option for Glioblastoma", Neuro-Oncology, 12(1):19-27.
Krutzfeldt et al. (Dec. 1, 2005) "Silencing of MicroRNAs in Vivo with 'Antagomirs'", Nature, 438(7068):685-689.
Kumar et al. (Nov. 2011) "Let-7 microRNA-mediated Regulation of IL-13 and Allergic Airway Inflammation", The Journal of Allergy and Clinical Immunology, e10, 128(5):1077-1085.
Kuperman et al. (Aug. 2002) "Direct Effects of Interleukin-13 on Epithelial Cells Cause Airway Hyperreactivity and Mucus Overproduction in Asthma", Nature Medicine, 8(8):885-889.
Kuperman et al. (Mar. 16, 1998) "Signal Transducer and Activator of Transcription Factor 6 (Stat6)-deficient Mice are Protected from Antigen-induced Airway Hyperresponsiveness and Mucus Production", Journal of Experimental Medicine, 187(6):939-948.
Laprise et al. (Mar. 23, 2004) "Functional Classes of Bronchial Mucosa Genes that are Differentially Expressed in Asthma", BMC Genomics, 5(1):10 pages.
Lavigne et al. (Nov. 12, 2004) "Human Bronchial Epithelial Cells Express and Secrete MMP-12", Biochemical and Biophysical Research Communications, 324(2):534-546.
Lee et al. (Apr. 2010) "Eosinophils in Health And Disease: The Liar Hypothesis", Clinical & Experimental Allergy, 40(4):563-575.
Lee et al. (Jan. 2006) "ERK1/2 Mitogen-activated Protein Kinase Selectively Mediates IL-13-induced Lung Inflammation and Remodeling in Vivo", Journal of Clinical Investigation, 116(1):163-173.
Lee et al. (Oct. 2001) "Interleukin-13 Induces Dramatically Different Transcriptional Programs in Three Human Airway Cell Types", American Journal of Respiratory Cell and Molecular, 25(4):474-485.
Lei et al. (Mar. 2007) "Transcriptional Regulation of Trk Family Neurotrophin Receptors", Cellular and Molecular Life Sciences, 64(5):522-532.
Leigh et al. (Apr. 1, 2004) "Type 2 Cytokines in the Pathogenesis of Sustained Airway Dysfunction and Airway Remodeling in Mice", American Journal of Respiratory and Critical Care Medicine, 169(7):860-867.
Leschziner et al. (Sep. 12, 2006) "ABCB1 genotype and PGP expression, function and therapeutic drug response: a critical review and recommendations for future research", The Pharmacogenomics Journal, 7(3):154-179.
Letunic et al. (Jan. 2012) "SMART 7: Recent Updates to the Protein Domain Annotation Resource", Nucleic Acids Research, 40:D302-D305.
Levi-Montalcini R. (Sep. 4, 1987) "The Nerve Growth Factor 35 Years Late", Science, 237(4819):1154-1162.
Lexmond et al. (Aug. 2013) "Elevated Levels Of leukotriene C4 Synthase mRNA Distinguish a Subpopulation of Eosinophilic Oesophagitis Patients", Clinical & Experimental Allergy, 43(8):902-913.
Li et al. (Oct. 2011) "Epigenetic Silencing of microRNA-375 Regulates PDKI Expression in Esophageal Cancer", Digestive Diseases and Sciences, 56(10):2849-2856.
Li et al. (Mar. 31, 2011) "miR-223 Regulates Migration and Invasion by Targeting Artemin in Human Esophageal Carcinoma", Journal of Biomedical Science, 18(1):9 pages.
Liacouras et al. (Jul. 2011) "Eosinophilic Esophagitis: Updated Consensus Recommendations for Children and Adults", Journal of Allergy and Clinical Immunology, 128(1):3-26.

(56) References Cited

OTHER PUBLICATIONS

Liacouras et al. (Sep. 2007) "Summary of the First International Gastrointestinal Eosinophil Research Symposium", Journal of Pediatric Gastroenterology and Nutrition, 45(3):370-391.

Liesveld Jane (Dec. 2018) "Hypereosinophilic Syndrome", MSD Manual Professional Version, 5 Pages.

Lim et al. (Jan. 1, 2014) "Demethylation of the Human Eotaxin-3 Gene Promoter Leads to the Elevated Expression of Eotaxin-3", Journal of Immunology, 192(1):466-474.

Lim et al. (Apr. 15, 2011) "Epigenetic Regulation of the IL-13-induced Human Eotaxin-3 Gene by CREB-binding Protein-mediated Histone 3 Acetylation", Journal of Biological Chemistry, 286(15):13193-13204.

Lin et al. (Mar. 31, 2011) "miR-142-3p as a Potential Prognostic Biomarker for Esophageal Squamous Cell Carcinoma", Journal of Surgical Oncology, 105(2):175-182.

Linch et al. (Nov. 2009) "Mouse Eosinophils Possess Potent Antibacterial Properties in Vivo", Infection and Immunity, 77(11):4976-4982.

Linch et al. (Jun. 2011) "The Role of Eosinophils in Non-parasitic Infections", Endocrine, Metabolic & Immune Disorders—Drug Targets, 11(2):165-172.

Lipkin Stefanien. (Apr. 1979) "Eosinophil Counts in Bacteremia", Archives of Internal Medicine, 139(4):490-491.

Liu et al. (Feb. 2012) "Role of microRNA let-7 and Effect to HMGA2 in Esophageal Squamous Cell Carcinoma", Molecular Biology Reports, 39(2):1239-1246.

Livak et al. (2001) "Analysis of Relative Gene Expression Data using Real-Time Quantitative PCR and the 2-Delta DeltaCT Method", Methods, 25:402-408.

Lo et al. (Dec. 16, 2011) "Identification of a Novel Mouse p53 Target Gene DDA3", Oncogene, 18(54):7765-7774.

Long et al. (Jun. 1, 2002) "Disruption of the NAD(P)H:quinone Oxidoreductase 1 (NQO1) Gene in Mice Causes Myelogenous Hyperplasia", Cancer Research, 62(11):3030-3036.

Lovinsky-Desir et al. (Jun. 2012) "Epigenetics, Asthma, and Allergic Diseases: A Review of the Latest Advancements", Current Allergy and Asthma Reports, 12(3):211-220.

Lu et al. (2013) "Diagnostic, functional, and therapeutic roles of microRNA in allergic diseases", Journal Of Allergy And Clinical Immunology, 132(1):3-13.

Lu et al. (Sep. 17, 2010) "Function of miR-146a In Controlling Treg Cell-mediated Regulation of Th1 Responses", Cell, 142(6):914-929.

Lu et al. (Jul. 16, 2012) "MicroRNA Profiling in Mucosal Biopsies of Eosinophilic Esophagitis Patients Pre and Post Treatment with Steroids and Relationship with mRNA Targets", PLoS One, e40676, 7(7):11 pages.

Lu et al. (Apr. 2012) "MicroRNA signature in Patients with Eosinophilic Esophagitis, Reversibility with Glucocorticoids, and Assessment as Disease Biomarkers", The Journal of Allergy and Clinical Immunology, e9, 129(4):1064-1075.

Lu et al. (Apr. 15, 2009) "MicroRNA-21 is Up-Regulated in Allergic Airway Inflammation and Regulates IL-12p35 Expression", Journal of Immunology, 182(8):4994-5002.

Lu et al. (Sep. 15, 2011) "MicroRNA-21 Limits in Vivo Immune Response-mediated Activation of the IL-12/IFN- gamma Pathway, Th1 Polarization, and the Severity of Delayed-type Hypersensitivity", Journal of Immunology, 187(16):3362-3373.

Lu et al. (Feb. 15, 2013) "miR-223 Deficiency Increases Eosinophil Progenitor Proliferation", Journal of Immunology, 190(4):1576-1582.

Lu et al. (Jul. 2012) "MiR-375 is Downregulated in Epithelial Cells after IL-13 Stimulation and Regulates an IL-13-Induced Epithelial Transcriptome", Mucosal Immunology, 5(4):388-396.

Lu et al. (Mar. 22, 2013) "Targeted Ablation of miR-21 Decreases Murine Eosinophil Progenitor Cell Growth", PLoS One, e59397, 8(3):8 pages.

Lucendo et al. (Jun. 15, 2011) "Montelukast Was Inefficient in Maintaining Steroid-Induced Remission in Adult Eosinophilic Esophagitis", Digestive Diseases and Sciences, 56(12):3551-3558.

Lucendo et al. (Sep. 2008) "Treatment with Topical Steroids Downregulates IL-5, Eotaxin-1/CCL11, and Eotaxin-3/CCL26 Gene Expression in Eosinophilic Esophagitis", The American Journal of Gastroenterology, 103(9):2184-2193.

Zahm et al. (Jul. 2011) "Circulating MicroRNA Is a Biomarker of Pediatric Crohn Disease", Journal of Pediatric Gastroenterology and Nutrition, 53(1):26-33.

Markowitz et al. (Apr. 2003) "Elemental Diet Is an Effective Treatment for Eosinophilic Esophagitis in Children and Adolescents", The American Journal of Gastroenterology, 98(4):777-782.

Martin et al. (May 2003) "Role of Innate Immune Factors in the Adjuvant Activity of Monophosphoryl Lipid A", Infection and Immunity, 71(5):2498-2507.

Martinez-Nunez et al. (Jan. 21, 2011) "The Interleukin 13 (IL-13) Pathway in Human Macrophages is Modulated by MicroRNA-155 Via Direct Targeting of Interleukin 13 Receptor Alpha1 (IL13Ralpha1)", Journal of Biological Chemistry, 286(3):1786-1794.

MATSUSHIMA (2010) "MicroRNAs And Esophageal Squamous Cell Carcinoma", Digestion, 82(3):38-144,.

Mattes et al. (Nov. 3, 2009) "Antagonism of microRNA-126 Suppresses the Effector Function of TH2 Cells and the Development of Allergic Airways Disease", Proceedings of the National Academy of Sciences of the United States of America, 106(44):18704-18709.

Mayer et al. (Apr. 27, 2001) "Identification of Receptor Binding and Activation Determinants in the N-Terminal and N-loop Regions of the CC Chemokine Eotaxin", Journal of Biological Chemistry, 276(17):13911-13916.

Mayo Clinic, "Eosinophilic Esophagitis", Available at: http://www.mayoclinic.org/diseases-conditions/eosinophilic-esophagitis/basics/treatment/con-20035681., Oct. 10, 2017.

European Search Report and Written Opinion for the European Application No. EP19787916, mailed Mar. 1, 2022, 9 pages.

Ferguson et al., Pediatric Eosinophilic Esophagitis Endotypes: Are We Closer to Predicting Treatment Response? Clinical Reviews in Allergy & Immunology (2018) 55:43-55.

Ochiai et al., "Thymic stromal lymphopoietin drives the development of IL-13+ Th2 cells" PNAS—Jan. 30, 2023, vol. 115. No. 5, 1033-1038.

Collins et al. (Oct. 2005) "Online Selection of Discriminative Tracking Features", IEEE Transactions on Pattern Analysis and Machine Intelligence, 27(10):1631-1643.

Collison et al. (Jul. 2011) "Inhibition of House Dust Mite-induced Allergic Airways Disease by Antagonism of MicroRNA-145 is Comparable to Glucocorticoid Treatment", The Journal of Allergy and Clinical Immunology, e4, 128(1):160-167.

Corren et al. (Sep. 22, 2011) "Lebrikizumab Treatment in Adults with Asthma", The New England Journal of Medicine, 365(12):1088-1098.

Crews et al. (Jan. 29, 2014) "Clinical Pharmacogenetics Implementation Consortium Guidelines For Cytochrome P450 2d6 Genotype And Codeine Therapy", Clinical Pharmacology & Therapeutics, 95(4):376-382.

Czajkowsky et al. (Oct. 2012) "Fc-fusion Proteins: New Developments and Future Prospectives", EMBO Molecular Medicine, 4(10):1015-1028.

D'Agostini et al. (Jul. 2005) "Antitumour Effect of Om-174 and Cyclophosphamide on Murine B16 Melanoma in Different Experimental Conditions", International Immunopharmacology, 5(7-8):1205-1212.

Dalal et al. (1997) "Molecular Characterization of Neurotrophin Expression and the Corresponding Tropomyosin Receptor Kinases (trks) in Epithelial and Stromal Cells of the Human Prostate", Molecular and Cellular Endocrinology, Oct. 31, 134(1):15-22.

Davis Carla M. (Feb. 11, 2011) "Diagnosis and Treatment of Eosinophilic Gastrointestinal Disorders", Pediatric Allergy, Immunology, and Pulmonology, 23(4):237-242.

De Bruin et al. (Oct. 7, 2010) "Eosinophil Differentiation in the Bone Marrow is Inhibited by T Cell-derived IFN-γ", Blood, 116(14):2559-2569.

(56) References Cited

OTHER PUBLICATIONS

Debrosse et al. (Jul. 2010) "Identification, Epidemiology and Chronicity of Pediatric Esophageal Eosinophilia from 1982-1999", The Journal of Allergy and Clinical Immunology, 126(1):112-119.
Dellon et al. (May 1, 2014) "59 Immunohistochemical Evidence of Inflammation Is Similar in Patients With Eosinophilic Esophagitis and PPI-Responsive Esophageal Eosinophilia: A Prospective Cohort Study", Gastroenterology, 146(5):S17.
Dellon et al. (Oct. 22, 2013) "Clinical and endoscopic characteristics do not reliably differentiate PPI-responsive esophageal eosinophilia and eosinophilic esophagitis in patients undergoing upper endoscopy: a prospective cohort study", The American Journal of Gastroenterology, 108(12):1854-1860.
Dellon et al. (Jul. 2012) "Eosinophilic Esophagitis: Diagnostic Tests and Criteria", Current Opinion in Gastroenterology, 28(4):382-388.
Dellon et al. (Feb. 2011) "Tryptase Staining of Mast Cells may Differentiate Eosinophilic Esophagitis from Gastroesophageal Reflux Disease", The American Journal of Gastroenterology, 106(2):264-271.
Dent et al. (Nov. 1, 1990) "Eosinophilia in Transgenic Mice Expressing Interleukin 5", Journal of Experimental Medicine, 172(5):1425-1431.
Descamps et al. (Jul. 2005) "Expression of Nerve Growth Factor Receptors and their Prognostic Value in Human Breast Cancer", Oncology Reports, 14(1):161-171.
Dewson et al. (Oct. 1, 2001) "Interleukin-5 Inhibits Translocation of Bax to the Mitochondria, Cytochrome C Release, and Activation of Caspases in Human Eosinophil", Blood, 98(7):2239-2247.
Dohrman et al. (Aug. 1997) "Ethanol Reduces Expression of the Nerve Growth Factor Receptor, But not Nerve Growth Factor Protein Levels in the Neonatal Rat Cerebellum", Alcoholism: Clinical and Experimental Research, 21(5):882-893.
Donato et al. (Jan. 1, 2002) "Human HTm4 is a Hematopoietic Cell Cycle Regulator", Journal of Clinical Investigation, 109(1):51-58.
Driss et al. (Apr. 2, 2009) "TLR2-dependent Eosinophil Interactions with Mycobacteria: Role of Alpha-defensins", Blood, 113(14):3235-3244.
Dyer et al. (Sep. 15, 2008) "Functionally Competent Eosinophils Differentiated Ex Vivo In High Purity From Normal Mouse Bone Marrow", Journal of Immunology, 181(6):4004-4009.
Dyer et al. (Jan. 1, 2009) "Generation of Eosinophils from Unselected Bone Marrow Progenitors: Wild-type, TLR- And Eosinophil-deficient Mice", The Open Immunology Journal, 2:163-167.
Dyer et al. (Jun. 1, 2010) "Mouse and Human Eosinophils De Granulate in Response to Platelet-activating Factor (PAF) and C21 LysoPAF Via A PAF receptor-independent Mechanism: Evidence for a Novel Receptor", Journal of Immunology, 184(11):6327-6334.
Dyer et al. (Sep. 24, 2009) "Pneumoviruses Infect Eosinophils and Elicit MyD88-dependent Release of Chemoattractant Cytokines and Interleukin-6", Blood, 114(13):2649-2656.
Ehlers et al. (1991) "Differentiation of T Cell Lymphokine Gene Expression: The in Vitro Acquisition of T Cell Memory", Journal of Experimental Medicine, 173(1):25-36.
Eissing et al. (Feb. 1, 2012) "Pharmacogenomics of Codeine, Morphine, and Morphine-6-Glucuronide: Model- Based Analysis of the Influence of CYP2D6 Activity, UGT2B7 Activity, Renal Impairment, and CYP3A4 Inhibition", Molecular Diagnosis & Therapy, 16(1):43-53.
Elsner (Nov. 1992) "The CC Chemokine Antagonist Met-RANTES Inhibits Eosinophil Effector Functions through the Chemokine Receptors CCR1 and CCR3", European Journal of Immunology, 27(11):2892-2998.
Fahy et al. (Nov. 15, 2001) "Remodeling of the Airway Epithelium in Asthma", American Journal of Respiratory and Critical Care Medicine, 164(10 Pt 2):S46-S51.
Fardet et al. (Jan. 22, 2006) "Severe Strongyloidiasis in Corticosteroid-treated Patients: Case Series and literature Review", Journal of Infection, 54(1):18-27.
Festuccia et al. (Jan. 2007) "Tyrosine Kinase Inhibitor CEP-701 Blocks the NTRK1/NGF Receptor and Limits the Invasive Capability of Prostate Cancer Cells in Vitro", International Journal of Oncology, 30(1):193-200.
Flower et al. (Nov. 16, 1999) "Modelling G-protein-coupled Receptors for Drug Design", Biochimica et Biophysica Acta, 1422(3):207-234.
Fox et al. (Aug. 2002) "Eosinophilic Esophagitis: It's Not Just Kid's Stuff", Gastrointestinal Endoscopy, 56(2):260-270.
Freund-Michel et al. (Jan. 2008) "The Nerve Growth Factor and its Receptors in Airway Inflammatory Diseases", Pharmacology & Therapeutics, 117(1):52-76.
Frossard et al. (Oct. 1, 2004) "Nerve Growth Factor and its Receptors in Asthma and Inflammation", European Journal of Pharmacology, 500(1-3):453-465.
Fuentebella et al. (Sep. 2010) "Increased Number of Regulatory T Cells In Esophageal Tissue of Patients with Eosinophilic Esophagitis in Comparison to Gastro Esophageal Reflux Disease and Control Groups", Journal of Pediatric Gastroenterology and Nutrition, 51(3):283-589.
Fukada et al. (Jul. 2013) "OCT1 genetic variants influence the pharmacokinetics of morphine in children", Pharmacogenomics, 14(10):1141-1151.
Fukao (Jun. 2007) "An Evolutionarily Conserved Mechanism for MicroRNA-223 Expression Revealed by MicroRNA Gene Profiling", Cell, 129(3):617-631.
Fukuda et al. (Feb. 2013) "Oral Session II-A (OII-A) Special Populations 3:45 pm-4:45 pm", Clinical Pharmacology & Therapeutics, 93:S49-S51.
Fulkerson et al. (Oct. 31, 2006) "A Central Regulatory Role for Eosinophils and the Eotaxin/CCR3 Axis in Chronic Experimental Allergic Airway Inflammation", Proceedings of the National Academy of Sciences of the United States of America, 103(44):16418-16423.
Fulkerson et al. (Feb. 2013) "Targeting Eosinophils in Allergy, Inflammation and Beyond", Nature Reviews Drug Discovery, 12(2):117-129.
Furuta et al. (Oct. 2007) "Eosinophilic Esophagitis in Children and Adults: A Systematic Review and Consensus Recommendations for Diagnosis and Treatment", Gastroenterology, 133(4):1342-1363.
Garbacki et al. (Jan. 28, 2011) "MicroRNAs Profiling in Murine Models of Acute and Chronic Asthma: A Relationship with mRNAs Targets", PLoS One, e16509, 6(1):23 pages.
Garcia-Echeverria et al. (Apr. 2004) "In Vivo Antitumor Activity of NVP-AEW541-A Novel, Potent, and Selective Inhibitor of the IGF-IR Kinase", Cancer Cell, 5(3):231-239.
Garçon et al. (Aug. 1, 2011) "Development of an AS04-adjuvanted HPV Vaccine with the Adjuvant System Approach", BioDrugs, 25(4):217-226.
Zhang et al. (Dec. 2009) "Effects of Endogenous Glucocorticoids on Allergic Inflammation and T(H)1/T(H)2 Balance in Airway Allergic Disease", Annals of Allergy, Asthma & Immunology, 103(6):525-534.
Zeng et al. (Feb. 2006) "Extracting Principal Diagnosis, Co-morbidity and Smoking Status for Asthma Research: Evaluation of a Natural Language Processing System", BMC Medical Informatics and Decision Making, 6(1):9 pages.
Zediak et al. (Mar. 1, 2011) "Cutting Edge: Persistently Open Chromatin At Effector Gene Loci In Resting Memory CD8+ T Cells Independent of Transcriptional Status", Journal of Immunology, 186(5):2705-2709.
Georgantas et al. (Feb. 20, 2007) "CD34+ Hematopoietic Stem-progenitor Cell MicroRNA Expression and Function: A Circuit Diagram of Differentiation Control", Proceedings of the National Academy of Sciences of the United States of America, 104(8):2750-2755.
Gilbert et al. (Aug. 1978) "Effects of Acute Endotoxemia and Glucose Administration on Circulating Leukocyte Populations in Normal and Diabetic Subjects", Metabolism, 27(8):889-899.
Goettig et al. (2010) "Natural and Synthetic Inhibitors of Kallikrein-Related Peptidases (KLKs)", Biochimie, 92(11):1546-67.

(56) References Cited

OTHER PUBLICATIONS

Khan, "Eosinophilic gastroenteritis," Best Practice & Research Clinical Gastroenterology, vol. 19, No. 2: 177-198 (2005) <doi: 10.1016/j.bpg.2005.01.009 >.
R&D Systems, "What is a Luminex® Assay," Multiplex Assays: R&D Systems, 6 pages (2024).
Rochman et al., "TSLP shapes the pathogenic responses of memory CD4 T cells in eosinophilic esophagitis," Science Signaling, vol. 16: 16 pages (Sep. 2023).
Chen et al., "Serine Protease Inhibitors Nafamostat Mesilate and Gabexate Attenuate Allergen-Induced Airway Inflammation and Eosinophilia in a murine Model of Asthma," The Journal of Allergy and Clinical Immunology, vol. 118, No. 1: 105-112 (Jul. 2006).
Frigas et al., "The eosinophil and the pathophysiology of astha," The Journal of Allergy and Clinincal Immunology, vol. 77, No. 4: 527-537 (Apr. 1986).
Zhou et al., "Strucural study of the uPA-nafamostat complex reveals a covalent inhibitory mechanism of nafamostat," Biophysical Journal, vol. 121, No. 20: 390-3949 (Aug. 2022).
European Office Action in EP Application No. 22162120.4, dated Mar. 27, 2025, 11 pages.

\* cited by examiner

FIG. 4C

| Plasma | Eotaxin-3 | IL5 | TARC |
|---|---|---|---|
| Cutoff (pg/mL) | >168 | >1.4 | >87 |
| Sensitivity% | 100 | 80.0 | 80.0 |
| Specificity% | 81.2 | 87.0 | 78.3 |
| Score | 1 | 1 | 1 |

Plasma EG score was scored using a 4-point scale (0 minimum; 3 maximum)

FIG. 4D

| Serum | Eotaxin-3 | IL5 | TSLP |
|---|---|---|---|
| Cutoff (pg/mL) | >32 | >1.5 | >6.7 |
| Sensitivity% | 76 | 64.7 | 70.6 |
| Specificity% | 85.7 | 95.2 | 95.2 |
| Score | 1 | 1 | 1 |

Serum EG score was scored using a 4-point scale (0 minimum; 3 maximum)

FIG. 7A-H
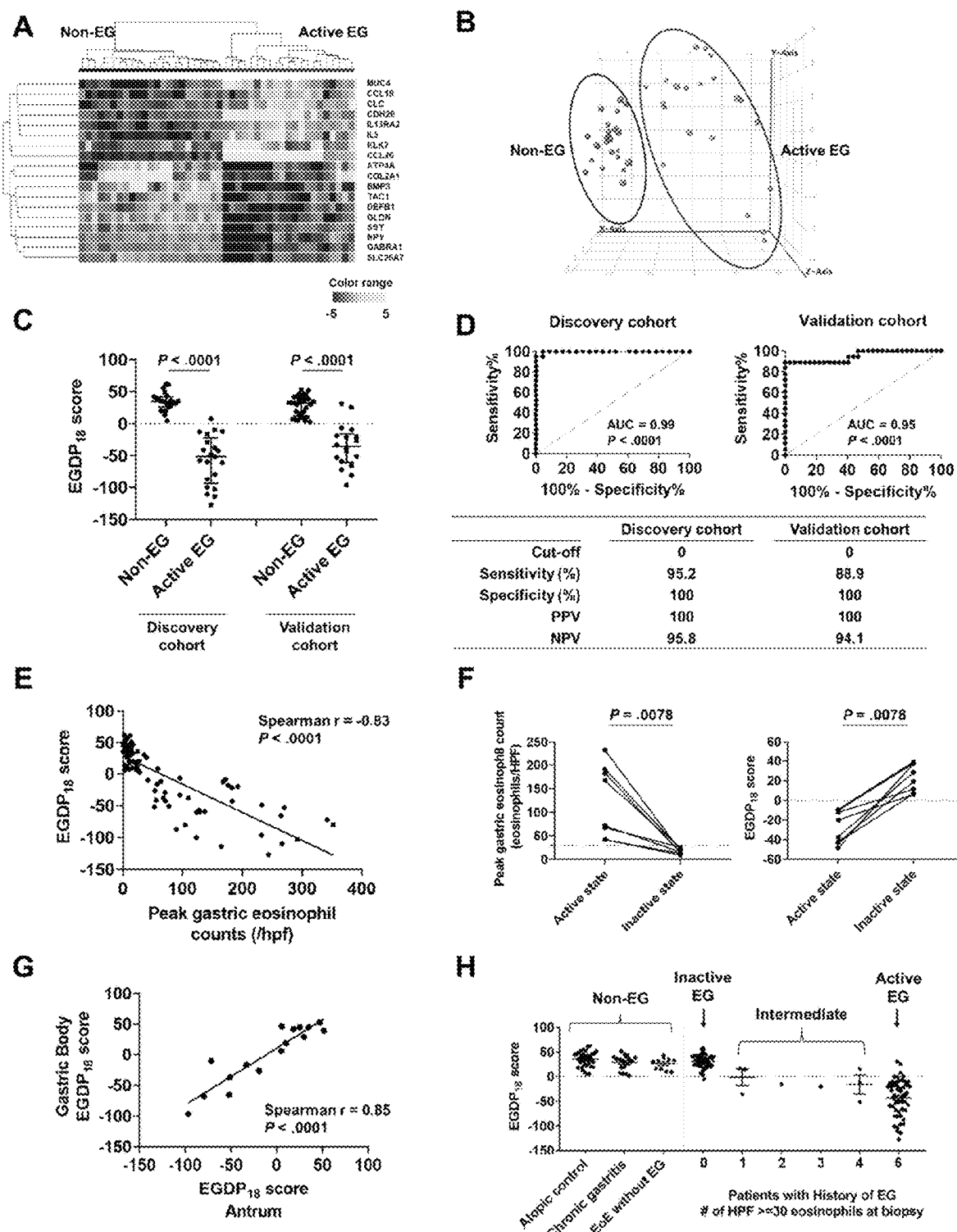

FIG. 8A-F
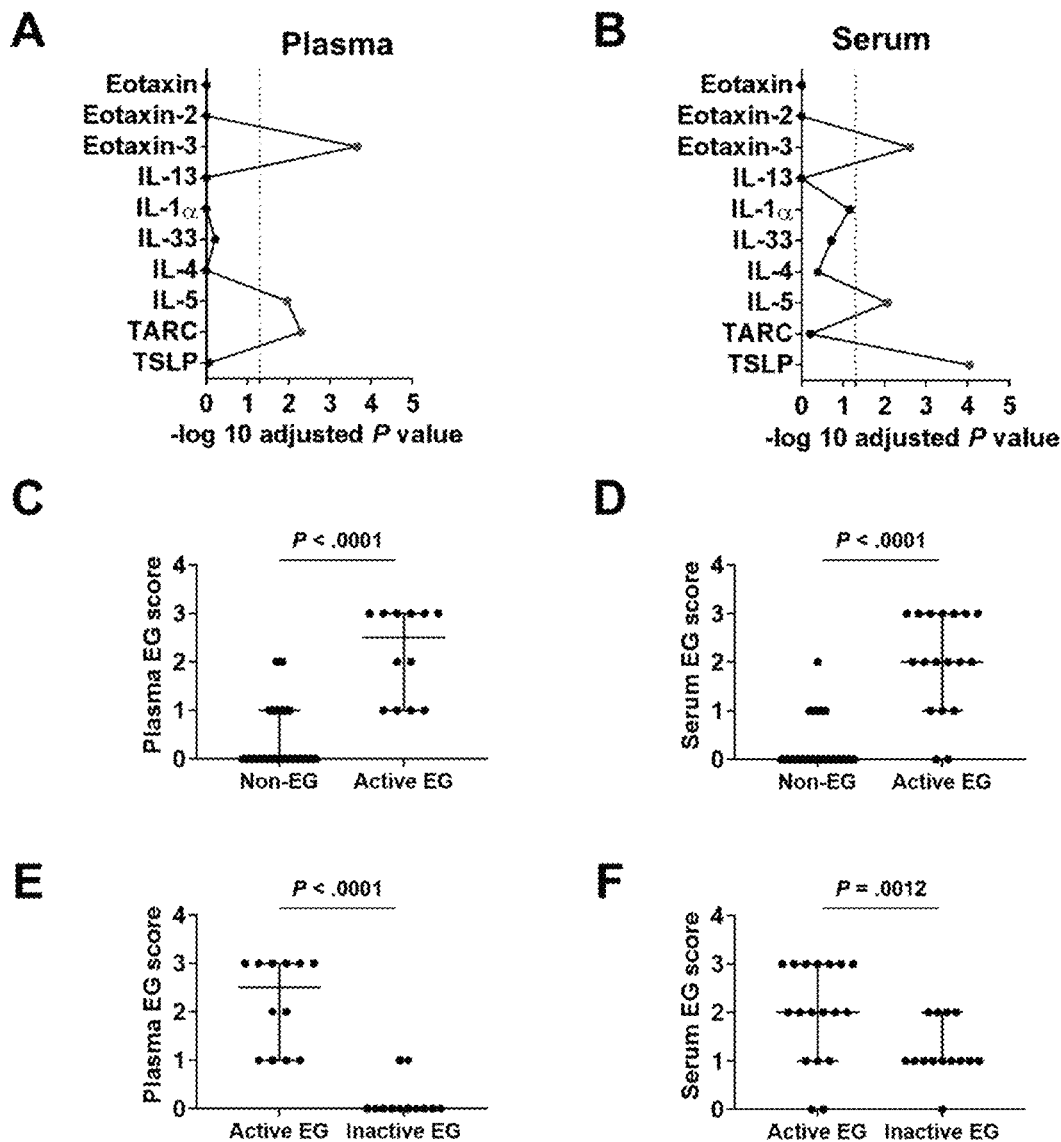

FIG. 9A-D
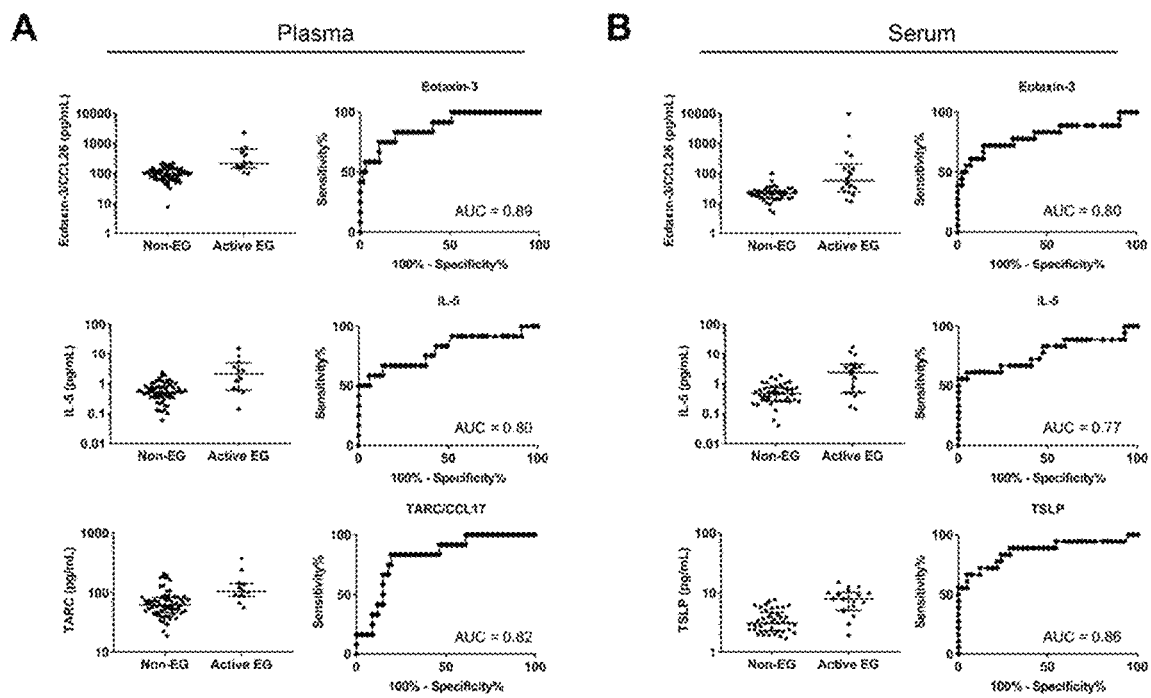

METHODS FOR DIAGNOSING AND TREATING EOSINOPHILIC GASTRITIS

CROSS REFERENCE TO RELATED APPLICATIONS

This application claims the benefit of U.S. Provisional Application No. 62/813,838, filed Mar. 5, 2019 and U.S. Provisional Application No. 62/810,093, filed Feb. 25, 2019, the entire disclosure of which is incorporated herein by reference in its entirety.

FIELD OF THE INVENTION

The disclosure relates to methods for diagnosing and treating eosinophilic gastritis.

BACKGROUND OF THE INVENTION

Eosinophilic esophagitis (EoE) has a unique transcriptome identified in gene microarray studies of esophageal biopsies from affected patients (Blanchard, C. et al. *J. Allergy Clin. Immunol.* 118:1054-9 (2006)). While EoE has been relatively well described, other forms of eosinophilic gastrointestinal disorders (EGIDs), such as eosinophilic gastritis (EG), are less well understood and have poorly defined diagnostic criteria.

Eosinophilic gastritis (EG) and eosinophilic gastroenteritis (EGE) are clinico-pathological disorders with marked gastric eosinophilia and clinical symptoms. EG or EGE diagnosis relies on mucosal eosinophil density; however, eosinophils reside in normal gastric mucosa, adding complexity to disease diagnosis and monitoring. EG, EGE and eosinophilic esophagitis (EoE, which may also be referred to as EE) are eosinophilic gastrointestinal disorders characterized by increased numbers of eosinophils in one or more parts of the wall of the affected GI segment(s) (Rothenberg, M. *J. Allergy Clin. Immunol.* 113:11-28 (2004). EG and EoE represent diseases characterized by accumulation of eosinophils in the stomach or esophagus, respectively. Many patients with EG or EGE also have concurrent involvement of other gastrointestinal segments with eosinophilic inflammation and disease, such as the esophagus and intestine. These patients are generally referred to as eosinophilic gastroenteritis (EGE). Caldwell J. M. *J Allergy Clin Immunol.* 134:1114-24 (2014).

There is an unmet need in the therapy of eosinophilic gastritis and gastroenteritis for more precise diagnostic tools. The present invention addresses this need by providing tissue- and blood-based diagnostic methods for EG and EGE.

SUMMARY OF THE INVENTION

The present invention relates to tissue and blood-based biomarkers for the diagnosis of EG and EGE, and for use in monitoring these patients once a diagnosis has been established. The biomarkers disclosed herein relate to both EG and EGE, since both are marked by gastric eosinophilia, and are also relevant where the patient may have concurrent involvement of other gastrointestinal segments with eosinophilic inflammation and disease, such as the esophagus and intestine. Accordingly, as used herein, the term "EG/EGE" refers to EG or EGE, or both.

The disclosure provides methods for diagnosing, monitoring, and optionally treating EG/EGE in a subject in need thereof, as well as methods for distinguishing these disorders from other gastrointestinal disorders, the methods comprising assaying a biological sample from the subject for one or more of the biomarkers described herein and diagnosing the subject based on the biomarker assay(s).

In embodiments, the one or more biomarkers is selected from a gene expression biomarker and a protein or polypeptide biomarker. The gene expression biomarker may comprise the expression of one or more genes or a panel of genes. The protein biomarker may comprise the expression of one or more proteins, or a peptide or polypeptide fragment thereof. In embodiments, the biological sample for use in detecting a gene expression biomarker is a gastric tissue sample. In embodiments, the biological sample for use in detecting a protein biomarker is a blood sample, including a serum or plasma sample.

In embodiments, the gene expression biomarker comprises the expression of one or more genes selected from the group consisting of, or is a panel of genes consisting of, ATPase, H+/K+ transporting subunit alpha (ATP4A), bone morphogenetic protein 3 (BMP-3), cadherin 26 (CDH26), C-C motif chemokine ligand 18 (CCL18), C-C motif chemokine ligand 26 (CCL26), collagen type II alpha 1 chain (COL2A1), Charcot-Leyden crystal galectin (CLC), defensin beta 1 (DEFB1), gamma-aminobutyric acid type A receptor, alpha 1 subunit (GABRA1), gliomedin (GLDN), interleukin 5 (IL-5), interleukin 13 receptor subunit alpha 2 (IL13RA2), Kallikrein-related peptidase 7 (KLK7), mucin 4, cell-surface associated (MUC4), neuropeptidase Y (NPY), solute carrier family 26 member 7 (SLC26A7), somatostatin (SST), and tachykinin precursor 1 (TAC1), and combinations of the foregoing.

In embodiments, the one or more genes is selected from the group consisting of, or is a panel of genes consisting of, BMP-3, CCL18, CCL26, DEFB1, GLDN, IL-5, IL13RA2, NPY, and TAC1.

In embodiments, the protein biomarker comprises one or more proteins, or a peptide or polypeptide fragment thereof, selected from the group consisting of C-C motif chemokine ligand 26 (CCL26), C-C motif chemokine ligand 17 (CCL17), interleukin 5 (IL-5), and thymic stromal lymphopoietin (TSLP).

In embodiments, the protein biomarker comprises one or more proteins, or a peptide or polypeptide fragment thereof, selected from the group consisting of C-C motif chemokine ligand 26 (CCL26), C-C motif chemokine ligand 17 (CCL17), interleukin 5 (IL-5), and thymic stromal lymphopoietin (TSLP).

In embodiments, the methods comprise differentiating or distinguishing EG/EGE from another gastrointestinal disorder selected from inflammatory bowel disease (IBD), *H. pylori* gastritis, lymphocytic gastritis, reactive gastritis, granulomatous gastritis, *H. heilmannii* gastritis, and non-steroidal anti-inflammatory drug (NSAID) gastritis.

In embodiments, the methods may further comprise a step of administering a therapy to the subject diagnosed as having EG or EGE, which may be referred to as an EG therapy or an EGE therapy, or an EG/EGE therapy. In embodiments, the therapy may be a dietary therapy. In embodiments, the therapy comprises the administration of a therapeutic agent selected from the group consisting of a glucocorticoid, a leukotriene inhibitor, azathioprine, an antihistamine, a mast-cell stabilizer, and a macrolide antibiotic. In embodiments, the therapy may comprise anti-IL-13 therapy, e.g. RPC4046, anti-eosinophil therapy, e.g. benralizumab, AK002, and anti-cytokine therapy, e.g. dupilumab, mepolizumab, and reslizumab.

BRIEF DESCRIPTION OF THE FIGURES

FIGS. 4A-D: Development of blood-based platforms and their diagnostic performance. Among the 10 biomarkers embedded in the platform, a statistical screening was performed between the non-EG/EGE patients and patients with EG/EGE in the (A) plasma and (B) serum cohort, respectively, resulting in 3 biomarkers with adjusted P<0.05. In (A), Eotaxin-3, IL-5 and TARC are the only markers on the right of the dotted line (scores>1) and are represented as lined circles. In (B) Eotaxin-3, IL-5 and TSLP are the only markers scoring>1 and are represented as lined circles. Blood EG/EGE scores were developed based on dimensionality reduction in (C) plasma samples and (D) serum samples.

FIG. 7A-H: Development of a tissue-based platform (EGDP) and EGDP18 score on the basis of differentially expressed genes. A, Heat map (light, upregulated; dark, downregulated) based on the 18 core genes (FDR P<0.01 and fold change>10-fold change) in the discovery cohort. B, Three-dimensional presentation using principal component analysis between samples based on the 18 core genes (dark, control subjects without EG; light, patients with EG). C, Comparison of the EGDP18 score between patients with EG and control subjects without EG in the discovery and validation cohort. D, ROC curve analysis showing the utility of the EGDP18 score for the diagnosis of EG. E, Correlation between peak gastric eosinophil counts and EGDP18 scores. F, Longitudinal changes of peak gastric eosinophil counts and EGDP18 scores in patients with EG at active and inactive states. G, Correlation of EGDP18 scores between the gastric antrum and body mucosa from the same subjects. H, EGDP18 score as a function of different patient groups, including patients with EG with involvement of 1 to 5 hpfs. NPV, Negative predictive value; PCA, principal component analysis; PPV, positive predictive value.

FIG. 8A-F: Development of blood-based platforms using a multiplex protein array. A and B, Among the 10 biomarkers embedded in the platform, a statistical screening was performed between the control subjects without EG and patients with EG in the plasma (A) and serum (B) cohorts separately, resulting in 3 biomarkers with an adjusted P value of less than 0.05 (Bonferroni correction). C and D, Levels of blood EG scores in patients with active EG (C, plasma; D, serum). E and F, Blood EG scores in patients with active EG and inactive EG (FIG. 4, plasma; F, serum).

FIG. 9A-D: Development of blood EG score based on significantly increased biomarkers. A and B, Levels of 3 biomarkers between the non-EG patients and patients with EG in the (A) plasma and (B) serum cohort (left panels). Line and error bars show the median and interquartile range, respectively. Data points represent individual subjects. ROC curves and performances of each biomarkers in the (A) plasma and (B) serum cohort (right panels). C and D, Scoring systems for plasma (C) and serum (D) established by dysregulated biomarker levels. AUC, area under the curve; EG, eosinophilic gastritis; ROC, receiver operating characteristic.

DETAILED DESCRIPTION OF THE INVENTION

Figure 1A:
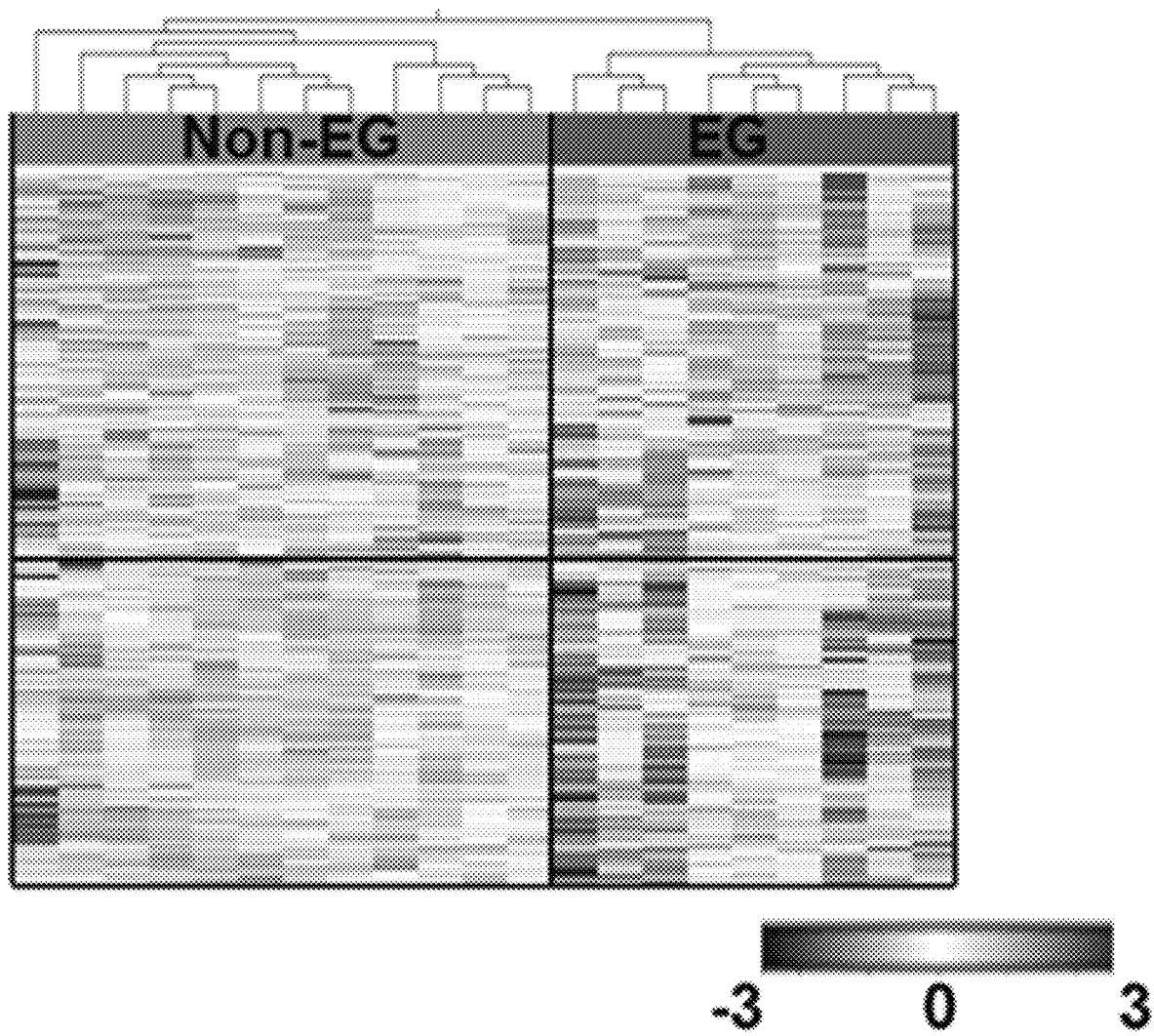
FIGS. 1A-B: (A) Heat map of 1,226 differentially dysregulated genes' expressions in EG/EGE patients versus normal healthy tissue (adjusted P<0.05, ≥2-fold change). Clustering analysis within each group was performed; each column represents tissue from an individual EG/EGE patient or control healthy tissue. (B) Venn diagrams comparing the number of genes identified as dysregulated in EG/EGE across different gene expression studies.

The present disclosure provides tissue-based gene expression and blood-based protein biomarkers for EG/EGE diagnosis, as well as for monitoring disease progression in patients already diagnosed, and related compositions and methods. Accordingly, the disclosure provides methods of diagnosing EG/EGE in a subject, the methods comprising assaying a biological sample from the subject for the presence of one or more biomarkers, as described herein, and determining the disease status of the subject based on the one or more biomarkers. For example, the disease status may be a diagnosis of EG or EGE, or a diagnosis of either EG/EGE, meaning that based on the analysis of the biomarker(s) the patient may have either EG or EGE. In embodiments, the biomarker is a gene expression biomarker comprising the expression of one or more genes, or a panel of genes, for example, as described in FIG. 2A, 3C, or 3D. In embodiments, the biomarker is a protein biomarker comprising a blood plasma or serum protein, or a peptide or polypeptide fragment thereof. In embodiments, the plasma or serum protein, or peptide or polypeptide fragment thereof, is selected from one or more of C-C motif chemokine ligand 11 (CCL11, eotaxin-1), C-C motif chemokine ligand 24 (CCL24, eotaxin-2), C-C motif chemokine ligand 26 (CCL26, eotaxin-3), C-C motif chemokine ligand 17 (CCL17, also known as TARC), interleukin-13 (IL-13), interleukin-1a (IL-1a), interleukin-33 (IL-33), interleukin-4 (IL-4), interleukin-5 (IL-5), and thymic stromal lymphopoietin (TSLP). In embodiments, the plasma or serum protein, or peptide fragment thereof, is selected from one or more of C-C motif chemokine ligand 26 (CCL26, also known as eotaxin 3), C-C motif chemokine ligand 17 (CCL17, also known as TARC), interleukin 5 (IL-5), and thymic stromal lymphopoietin (TSLP).

In embodiments, the disclosure provides a method for diagnosing, and optionally treating EG/EGE, as well as methods for monitoring disease progression, in a subject in need thereof, the methods comprising subjecting a biological sample from the subject to a method for gene expression analysis, determining the expression of a gene expression biomarker comprising one or more genes, or a panel of genes, in the biological sample, diagnosing EG/EGE based on the expression of the one or more genes or panel of genes, and optionally treating the patient with an EG/EGE therapy, or monitoring disease progression based on the expression of the one or more genes or panel of genes.

In embodiments, EG/EGE is diagnosed and the disease activity is monitored in the subject where the expression of the one or more genes, which may also be referred to herein as the "genes of interest" or "GOI", is above a diagnostic threshold, wherein the diagnostic threshold is determined based on the similarity between the expression of the one or more genes of interest ("GOI"), or panel of said genes, in gastric tissue of subjects having EG/EGE and the expression of the GOI of healthy control tissue. The similarity may be calculated as a geometric distance, for example, using hierarchical clustering of the gene expression data (Eisen et al. 1998 *Proc. Natl. Acad. Sci.* USA (25)95, p. 14863-14868) combined with a dimensionality reducing analysis, such as principal component analysis (PCA). According to the method of Eisen et al., the clustered gene expression data is graphically represented in a two-dimensional heat map such that groups of genes sharing a similar expression pattern over different conditions are grouped together by color (the color representing the measured gene expression, e.g., as a cycle threshold or CT value, preferably normalized to at least one reference gene). PCA seeks to reduce the dimensionality of the data matrix, e.g., x observations on y variables, by finding m new variables that together account for much of the original variance. The new variables are called 'principal components' because they account for as much of the original variance as possible while remaining uncorrelated and orthogonal to each other, thereby reducing dimensionality while filtering out 'noise' in the data. Since each principal component is a linear combination of the original variables, it is also typically possible to ascribe meaning to what they represent.

In embodiments, the subject is diagnosed, and/or disease progression is monitored, by assaying the expression of a panel of genes comprising two or more of bone morphogenetic protein 3 (BMP-3), cadherin 26 (CDH26) C-C motif chemokine ligand 18 (CCL18), C-C motif chemokine ligand 26 (CCL26), Charcot-Leyden crystal galectin (CLC), defensin beta 1 (DEFB1), gamma-aminobutyric acid (GABA) type A receptor, alpha 1 subunit (GABRA1), gliomedin (GLDN), interleukin 5 (IL-5), interleukin 13 receptor subunit alpha 2 (IL13RA2), neuropeptidase Y (NPY), and tachykinin precursor 1 (TAC1). In the embodiments, the subject is diagnosed by assaying the expression of each gene in a panel of genes, the panel of genes comprising or consisting of BMP-3, CDH26, CCL18, CCL26, CLC, DEFB1, GABRA1, GLDN, IL-5, IL13RA2, NPY, and TAC1. In embodiments, the subject is diagnosed by assaying the expression of each gene in a panel of genes, the panel of genes comprising or consisting of BMP-3, CCL18, CCL26, DEPB1, GLDN, IL-5, IL13RA2, NPY, and TAC1. In accordance with these embodiments, the term 'consisting of' in relation to a set of genes is intended to define the set of genes making up the panel.

In embodiments, the disclosure provides a method of diagnosing, monitoring, and optionally treating EG/EGE and further optionally monitoring disease progression in a subject, the methods comprising assaying a blood sample from the subject for one or more protein biomarkers present in the plasma or serum fraction of the blood sample, or peptide or polypeptide fragment(s) thereof, the biomarkers selected from CCL11 (alias eotaxin-1), CCL24 (alias eotaxin-2), CCL26 (alias eotaxin-3), CCL17 (alias TARC), IL-13, IL-1a, IL-33, IL-4, IL-5 and TSLP. In embodiments, the biomarker is selected from one or more of CCL26, CCL17, IL-5, and TSLP. In embodiments, the methods comprising assaying the plasma or serum fraction of the blood sample for each of CCL26, CCL17, IL-5, and TSLP, wherein the subject having each of CCL26, CCL17, IL-5, and TSLP above a diagnostic threshold is diagnosed with EG/EGE.

In embodiments, the disclosure provides a method of diagnosing, monitoring disease progression, and optionally treating EG/EGE in a subject, the methods comprising assaying a biological sample from the subject for the presence of CCL26. In embodiments, CCL26 gene expression is assayed in a gastric tissue sample from the subject and/or CCL26 protein is measured in a blood sample from the subject, including a serum or plasma sample. In accordance with this embodiment, elevated CCL26 gene expression or protein levels, relative to that in normal healthy gastric tissue, indicates a diagnosis of EG/EGE for the subject.

In embodiments, the disclosure also provides methods of distinguishing EG/EGE from other gastrointestinal disorders, the methods comprising assaying a biological sample from the subject for a biomarker as described herein. In embodiments, the other disorder is EoE or a non-eosinophilic inflammatory GI disorder such as inflammatory bowel disease (IBD) or a non-eosinophilic gastritis, such as *H. pylori* gastritis, lymphocytic gastritis, reactive gastritis, granulomatous gastritis (e.g., Crohn's gastritis), *H. heilmannii* gastritis, or non-steroidal anti-inflammatory drug (NSAID) gastritis.

In embodiments, the disclosure also provides methods of monitoring disease progression in patients already diagnosed, or guiding therapy in patients already diagnosed, the methods comprising assaying a biological sample from the subject for a biomarker as described herein, wherein the step of assaying for the biomarker is carried out more than one time point, preferably at least two points, in order to monitor disease progression and/or efficacy of therapy. For example, the biomarker may be assayed at an initial time point, which may be at the time of initial diagnosis or just before the start of therapy, and at a second or subsequent time point(s) following diagnosis or the start of therapy. In embodiments, the time is measured in days, e.g., the second or subsequent time point may be a period of days from the initial time point, such as 2, 3, 4, 5, 6, or 7 days. In embodiments, the time is measured in weeks, e.g., the second or subsequent time point may be a period of weeks from the initial time point, such as 2, 3, 4, 5, 6, 7, 8, 9, 10, or 12 weeks. In embodiments, the time is measured in months, e.g., the second or subsequent time point may be a period of months from the initial time point, such as 4, 5, 6, or 12 months.

In embodiments, the disclosure also provides methods of analyzing an archival sample obtained from a subject, the methods comprising assaying the archival sample for a biomarker as described herein. In some embodiments, the archival sample is a formalin-fixed, paraffin-embedded (FFPE) sample. In embodiments, the archival sample is a gastric tissue sample, for example a gastric mucosal biopsy sample.

The methods of the present disclosure are generally written as applicable to human subjects, also referred to as "patients", but the methods may be applied to other mammalian subjects. Accordingly, in embodiments a method described here may be performed on a "subject" which may include any mammal, for example a human, primate, mouse, rat, dog, cat, cow, horse, goat, camel, sheep or a pig. Preferably, the subject is a human. The term "patient" refers to a human subject.

In accordance with the methods described here, in some embodiments, a subject "in need of" treatment may be a subject suspected of having EG/EGE based on the presence of GI symptoms, such as one or more of severe abdominal pain, abdominal distension, nausea, vomiting, and diarrhea; histologic evidence of eosinophilic infiltration in one or more areas of the GI tract, especially the stomach and small intestine; and exclusion of other causes of tissue eosinophilia. In embodiments, the subject in need may be an adult or pediatric human patient having EG/EGE, or suspected of having EG/EGE based on presentation with one or more clinical symptoms.

The term "biological sample" as used herein may refer to a sample, including a biopsy sample, of a tissue, or other biological sample such as an exudate, gastric lavage, saliva, serum, plasma, mucus, blood, or urine sample; or a swab such as an oral or a buccal swab. In some embodiments, the sample is a tissue sample, for example a gastric or gastric mucosal tissue sample obtained at biopsy, or a blood sample, including a serum or plasma sample. In the context of the present disclosure a 'blood' sample is understood to mean a sample of whole blood taken for a subject, which necessarily includes a serum and plasma sample from the subject.

The terms "determining," "measuring," and "assaying" are used interchangeably herein and can include quantitative and/or qualitative determinations. These terms are intended to exclude purely mental steps and instead refer to the use of one or more laboratory assays for measuring gene expression or the presence of a protein or peptide in a biological sample. Such methods may include computer assisted steps for determining the amount of an analyte, such as the amount of a nucleic acid, e.g., RNA or DNA, or the amount of a protein, peptide, or polypeptide, in a biological sample, including for example the amount of an expressed transcript of a gene or panel of genes of interest, or the amount of a protein, peptide, or polypeptide in plasma or serum.

The term "differentially regulated" when used in connection with gene expression refers to genes whose expression is increased or decreased relative to a reference in a given state. For example, the state may be selected from normal healthy tissue, or diseased tissue. In the context of the present disclosure, the tissue may be healthy gastric tissue or diseased gastric tissue, for example from a subject having EG/EGE. The gastric tissue is preferably gastric mucosal tissue, for example as may be obtained at biopsy. In some embodiments, the reference may be the expression of one or more endogenous genes, such as housekeeping genes or other genes whose expression is known to be constant in the different states being examined, e.g., in normal healthy tissue versus the gastric tissue of EG/EGE patients. In some embodiments, the reference may be an average of the expression of multiple genes, such as multiple housekeeping genes. In some embodiments, the reference is one or more exogenous reference oligonucleotides, such as synthetic RNA or DNA, added to a sample in defined amounts. In some embodiments, more than one reference may be used, for example multiple exogenous control oligonucleotides and multiple endogenous housekeeping genes may be used as references in the same assay.

In the context of the present disclosure, the terms "treatment", "treating", or "treat" describe the management and care of a patient for the purpose of combating a disease or disorder, such as EG/EGE, and may include the administration of a therapeutic agent as well as the administration of a dietary therapy, such as a restricted diet, including elemental and elimination diets, to alleviate one or more symptoms or complications of EG/EGE thereby treating the EG/EGE. Therapeutic agents may include small molecules, such as glucocorticoids, e.g., fluticasone, prednisone and budesonide, or nonsteroidal agents, such as leukotriene inhibitors, azathioprine, anti-histamines, mast-cell stabilizers, macrolide antibiotics such as clarithromycin, or biologic agents, such as therapeutic antibodies or nucleic acids, including interfering RNAs.

In some embodiments, treating EG/EGE may comprise anti-cytokine therapy, including, for example, the administration of a biologic agent, such as an antibody, targeted to inhibit cytokine signaling by one or more cytokines via their cognate receptors. In embodiments, the anti-cytokine therapy is an anti-T helper type 2 (Th2) therapy. A Th2 immune response is generally characterized by the production of interleukin-4 (IL-4), interleukin-5 (IL-5), and interleukin-13 (IL-13). Accordingly, an anti-Th2 therapy encompasses a therapy targeting one or more of IL-4, IL-5, and IL-13, and/or their receptors in order to inhibit IL-4, IL-5, and/or IL-13 mediated signal transduction. The most common biologics for anti-cytokine therapy are antibodies, preferably monoclonal antibodies, and most preferably fully human or humanized monoclonal antibodies. In embodiments of the methods described here, the anti-cytokine therapy may be an anti-T helper type 2 (Th2) therapy selected from one or more of a therapy targeting the IL-4 and/or IL-13 signaling pathway, and a therapy targeting the IL-5 signaling pathway.

Interleukin-4 and interleukin-13 both mediate inflammation through their receptors, with IL-13 also binding to type 2 IL-4 receptors. IL-4 and IL-13 signaling pathways thus overlap and therapies envisioned by the methods described here may target one or both of these signaling pathways. Therapies targeting IL-4 signaling include monoclonal antibodies such as dupilumab, which targets the IL-4 receptor alpha (IL-4Ra). Therapies targeting IL-13 signaling include monoclonal antibodies such as RPC4046 or tralokinumab, both of which target IL-13.

Interleukin-5 (IL-5, CD125) is an eosinophil growth, activation, and survival factor. Humanized anti-IL-5 antibodies have been shown to be effective in treating asthma patients with the severe eosinophilic form of the disease, as discussed in Rothenberg ME. Humanized Anti-IL-5 Antibody Therapy. Cell 2016; 165(3): 509. Therapies targeting the IL-5 signaling pathway include, for example, therapies targeting IL-5 and its receptor, also known as CD125. Such therapies include monoclonal antibodies such as mepolizumab and reslizumab, which target IL-5, and monoclonal antibodies such as benralizumab, which target the IL-5 receptor.

Methods of Measuring Gene Expression

In embodiments, the methods described here may comprise determining the gene expression levels of one or more genes, and making a determination as to the EG/EGE status of the subject based upon the gene expression levels. In accordance with the methods described here, the expression of one or more genes, or of a panel of genes, is measured in a biological sample, such as a gastric mucosal biopsy sample, obtained from a patient in need of treatment as described herein.

In embodiments, the methods require determining whether the expression level of the one or more genes is increased or decreased relative to a reference. The terms 'level' and 'amount' when used in the context of gene expression are used interchangeably to refer to the amount of gene transcripts in a cell or tissue sample. Where the amount is a relative amount, it is relative to the expression of a reference gene or the expression of a reference set of genes, or the amount of one or more reference oligonucleotides which are exogenously added to a sample. In some embodiments, the reference is selected from one or more of an endogenous gene, an exogenously added reference oligonucleotide including an artificial RNA or DNA, a reference gene index, or a target gene index. A reference gene index may be comprised of multiple averaged endogenous control genes such as multiple housekeeping genes. A target gene index may be comprised of multiple averaged genes of interest, such as multiple genes described herein as differentially expressed in EG/EGE. In some embodiments, more than one reference may be used, for example multiple exogenous control oligonucleotides and multiple endogenous housekeeping genes may be used in the same assay. In embodiments, the reference may be a computed average expression value for one or more genes expressed. In some embodiments, the reference set of genes is the expression of the one or more target biomarker genes in normal healthy tissue. Generally, normal healthy gastric tissue is defined as having less than 11 eosinophils per high power field and no basal layer expansion.

Gene expression may be determined, for example, using a method for detecting and quantitating mRNA expression. Such methods include reverse transcription followed by a polymerase chain reaction (PCR), including a quantitative PCR (qPCR) reaction. The steps may comprise generating a single stranded complementary DNA (cDNA) template from mRNA of the biological sample, e.g., through the performance of a reverse transcription (RT) reaction. Additional steps may include amplification of the cDNA and performance of a method for determining the amount of amplified DNA, for example through the use of labeled probes or DNA intercalating dyes. Additional methods include quantitative PCR performed with a low density array or high density microarray based technique. In embodiments, the methods described here may further comprise one or more steps of converting mRNA to cDNA, converting cDNA to labelled cRNA, e.g., biotinylated cRNA, and hybridizing the labelled cRNA to an oligonucleotide-based DNA microarray chip.

In embodiments, the methods described here may further comprise one or more additional steps of extracting RNA from a biological sample obtained from the patient, for example, a gastric biopsy sample. The steps may include isolating total RNA and/or mRNA from the biological sample, converting mRNA to cDNA, and performing a PCR-based amplification step. mRNA may be isolated from total RNA, for example using a commercially available kit, such as the RNeasy™ Mini kit (Qiagen), followed by enriching for mRNA using a suitable method, such as oligo(dT) magnetic beads. The mRNA may also be fragmented into short fragments of about 200 base pairs (bp) using a suitable fragmentation buffer. cDNA may be produced from the mRNA, for example, using the fragmented mRNA as a template with random hexamer primers for first-strand cDNA synthesis followed by second-strand cDNA synthesis and purification of the short double-stranded cDNA fragments using standard protocols or a commercially available kit, for example a QIAquick™ PCR purification kit (Qiagen).

The term "microarray" refers to arrays of probe molecules that can be used to detect analyte molecules, e.g., oligonucleotide probe arrays to measure gene expression. The terms "array," "slide," and "chip" may be used interchangeably to refer to oligonucleotide probe arrays. Such arrays may comprise oligonucleotide probes that are synthesized in silico on the array substrate, sometimes referred to as 'high density' arrays, or the arrays may be spotted arrays, which tend to have lower densities.

The term "gene expression" refers to the transcription of DNA sequences into RNA molecules. The expression level of a given gene measured at the nucleotide level refers to the amount of RNA transcribed from the gene measured on a relevant or absolute quantitative scale. The measurement can be, for example, an optical density value of a fluorescent signal on a microarray image. Differential expression means that the expression levels of certain genes, as measured at the nucleotide level, are different in different states, tissues, or type of cells, relative to the amount or level of gene expression of a reference gene.

For qPCR based methods, the gene expression may be presented as a delta cycle threshold (Ct) value. The Ct value is defined as the number of PCR cycles required for the fluorescent signal of an amplified product to exceed a background or threshold level. The Ct value is therefore inversely proportional to the amount of the target nucleic acid in the sample. The delta Ct value represents the difference in expression between a target gene and a reference gene calculated as a difference in the Ct values of the target and reference genes in the sample.

In some embodiments, gene expression may further be compared to a second relative parameter such as a non-treated control, a time point (e.g., time zero), or healthy cells, tissues or subjects. Generally, normal healthy tissue is defined histologically as having less than 11 eosinophils per high power field and no basal layer expansion.

In embodiments, the methods described here may further comprise one or more additional steps of extracting RNA from a biological sample obtained from the patient, for example, a gastric biopsy sample. The steps may include isolating total RNA and/or mRNA from the biological sample, converting mRNA to cDNA, and performing a PCR-based amplification step. mRNA may be isolated from total RNA, for example using a commercially available kit, such as the RNeasy™ Mini kit (Qiagen), followed by enriching for mRNA using a suitable method, such as oligo(dT) magnetic beads. The mRNA may also be fragmented into short fragments of about 200 base pairs (bp) using a suitable fragmentation buffer. cDNA may be produced from the mRNA, for example, using the fragmented mRNA as a template with random hexamer primers for first-strand cDNA synthesis followed by second-strand cDNA synthesis and purification of the short double-stranded cDNA fragments using standard protocols or a commercially available kit, for example a QIAquick™ PCR purification kit (Qiagen).

In some embodiments of the methods described here, the methods may further comprise one or more additional steps of isolating protein from a biological sample obtained from the patient, for example, a gastric biopsy sample. The steps may include isolating total protein from the sample and separating the proteins by one or more chromatographic methods, for example column chromatography, gel chromatography, liquid chromatography, including high pressure liquid chromatography (HPLC), mass spectrophotometry (MS), and combination liquid chromatography mass-spectrophotometry methods, e.g., LC-MS/MS. The analysis may further include chemiluminescence or fluorescence based detection of protein, peptide, or polypeptide analytes, for example in an immunoassay.

Examples

The following describes work to develop tissue and blood-based diagnostic platforms for EG/EGE, to validate their utility for EG/EGE diagnosis and management, and to better understand disease pathogenesis. Previous work by our laboratory, for example U.S. Pat. No. 9,345,763, has shown that the gastric tissue of patients with EG/EGE exhibits a conserved pattern of gene expression. In that work we identified a set of 28 genes whose expression was increased and 76 whose genes whose expression was decreased in the gastric tissue of patients with active EG/EGE compared to that of normal healthy tissue from control patients. Of these genes, only 11 overlapped with those previously identified as being dysregulated in the esophageal tissue of patients with EoE, including CDH26 and IL-13. The present disclosure extends that earlier work and provides a diagnostic panel of expressed genes for diagnosing EG/EGE as well as plasma or serum protein biomarkers for EG/EGE.

Methods

Patients with EG/EGE and non-EG/EGE controls were enrolled across 10 sites associated with the Consortium of Eosinophilic Gastrointestinal Disease Researchers (CE-GIR). EG/EGE was diagnosed as gastric eosinophilia≥30 eosinophils/HPF in ≥5 HPFs. Genome-wide gene expression profiles from gastric biopsies were generated by RNA sequencing. An EG/EGE Diagnostic Panel (EGDP) focusing on a set of 48 informative gastric transcripts and an EG/EGE blood biomarker panel based on a 10 protein multiplex array were analyzed for their performance in discovery and validation cohorts. The EGDP score was calculated by summation of delta cycle threshold (CT) values of the most highly dysregulated genes (ΣΔCT). Blood EG/EGE scores were established by dysregulated cytokines/chemokine levels. For diagnosis, the area under the receiver operating characteristic curve (AUC) was calculated.

For the cluster analysis, the difference between Gene of Interest (GOI) CT expression values and that of an internal reference gene, GAPDH, was normalized to the median of all samples for each given gene. Consequently, clustering was performed by hierarchical clustering design to assemble the dendrogram. When sample similarity/dissimilarity was compared, condition and gene entity were 2-D clustered in conjunction with an expression heat map.

For the ΣΔCT algorithm, the summation of delta CT values of the most highly dysregulated genes (ΣΔCT) was calculated. These were the genes having the most significant dysregulation as defined by FDR p-value<0.01 and fold change>=5, which were the following 12 genes: BMP-3, CDH26, CCL18, CCL26, CLC, DEFB1, GABRA1, GLDN, IL-5, IL13RA2, NPY, and TAC1 ("the 12 EG genes of interest or "GOI"). The expression CT value of the reference housekeeping gene, GAPDH, was first subtracted from each of the 12 EG GOI CT values to acquire the ΔCT. The sums of the ΔCT were calculated separately for up-regulated (6 genes) and down-regulated (6 genes) gene groups. A negative weight was endowed to the up-regulated gene sum before the addition of the two ΣΔCT values to establish the "EGDP Score", reflecting the disease-specific expression signature and disease severity.

For principal component analysis (PCA), to visualize the geometric distance between any given samples, a 3-dimensional plot was generated based on the top 3 variance contributors between the EG and non-EG subjects as previously described using GeneSpring™ analysis software. For more detail see Shoda et al., *Lancet Gastroenterol Hepatol.* 2018 July; 3(7):477-488; Epub 2018 May 3. PubMed PMID: 29730081; Shoda et al., *J Allergy Clin Immunol Pract.* 2017 November-December; 5(6):1639-1649.e2. Epub 2017 May 16; Wen et al., *J Allergy Clin Immunol.* 2015 January; 135(1):187-97. Epub 2014 Oct. 19; and Wen et al., *Gastroenterology.* 2013 December; 145(6): 1289-99. Epub 2013 Aug. 23, the contents of each of which is hereby incorporated by reference in its entirety.

For Blood EG scores, scoring systems for plasma and serum were established by dysregulated cytokines/chemokine levels, respectively. For instance, point 1 was added to a score when each 3 specific cytokines have a value higher than the cutoff value (pg/mL) to differentiate from non-EG. A plasma or serum EG score is the sum of the assigned scores for each 3 cytokines assessed, ranging from 0 to 3.

Results

Figure 1B:
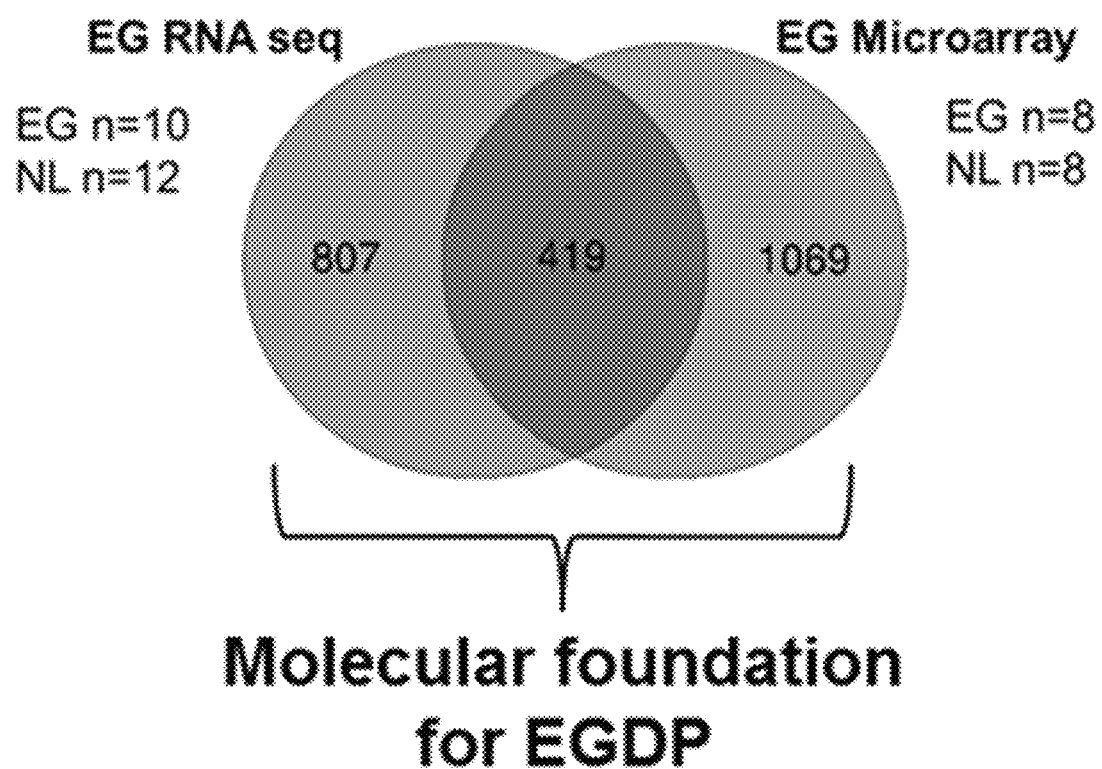
Figure 2A:
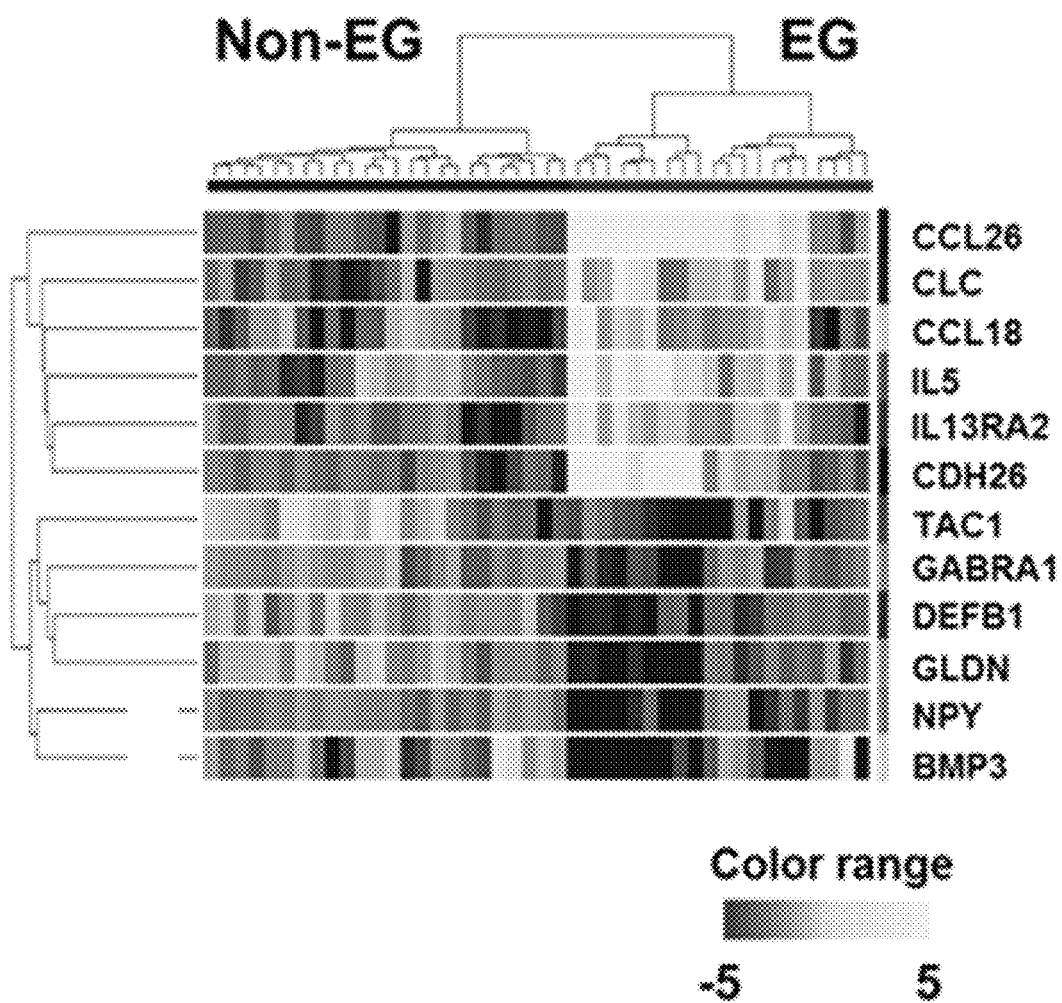
FIGS. 2A-F: Development of a tissue-based platform (EGDP) and its diagnostic performance. (A) Forty-eight EG/EGE genes were embedded and a statistical screening was performed between the non-EG/EGE patients and patients with EG/EGE in the discovery cohort, resulting in 12 genes with adjusted P<0.01 and fold change≥5-fold change. Based on these 12 core genes, a heat map was created. (B) Twelve-gene/-dimension expression data on non-EG/EGE controls and patients with EG/EGE were reduced to 3D presentation by principal component analysis (PCA) for visual presentation of the expression distance between samples. (C) An EGDP score was developed based on dimensionality reduction to distinguish EG/EGE vs non-EG/EGE. (D) After optimizing potential score ranges, a score≤4 yielded a PPV=100%, a score≥17 and NPV=100%, and only 12.8% of subjects had an indeterminate score by this classification scheme. (E) Correlation of EGDP score between gastric antrum and body mucosa (gray lined circles: active EG/EGE patients; black circles: non-EG/EGE patients). (F) When analyzed by EGDP score, all of the patients with intermediate tissue eosinophil levels (i.e., the number of HPFs with ≥30 eosinophils is n=1 to 4) are molecularly equivalent to active EG/EGE.
Figure 2B:
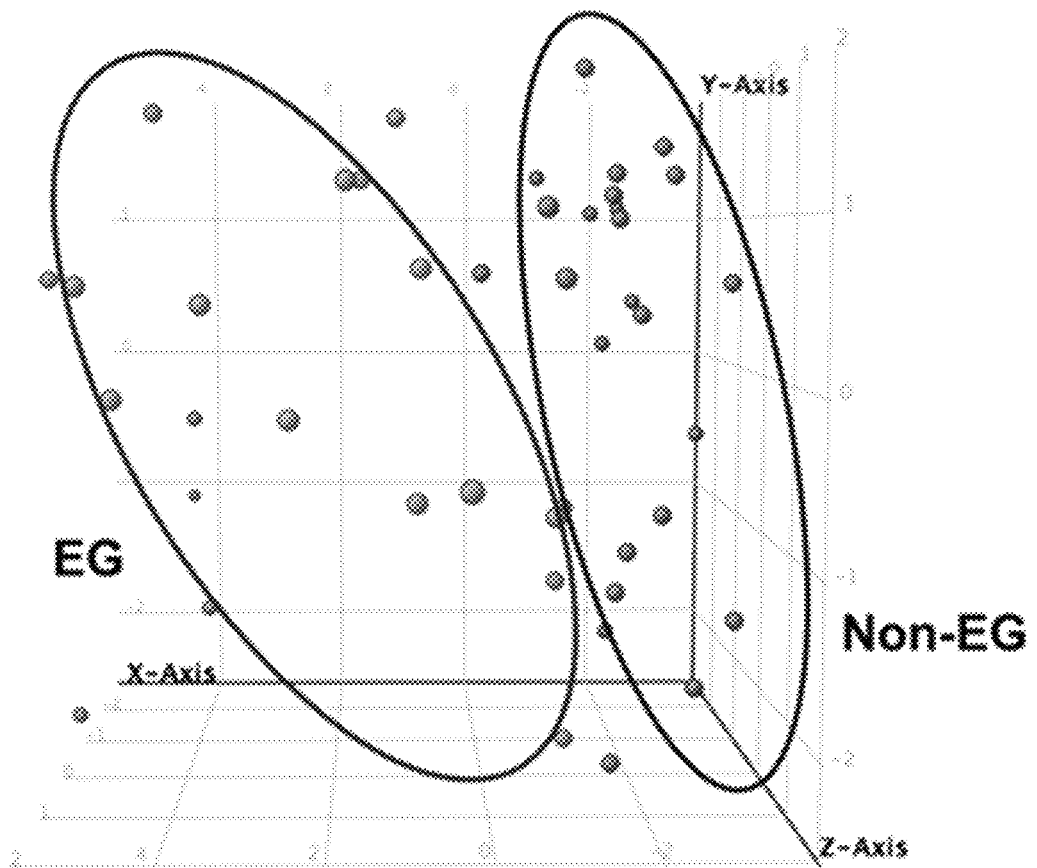
Figure 2C:
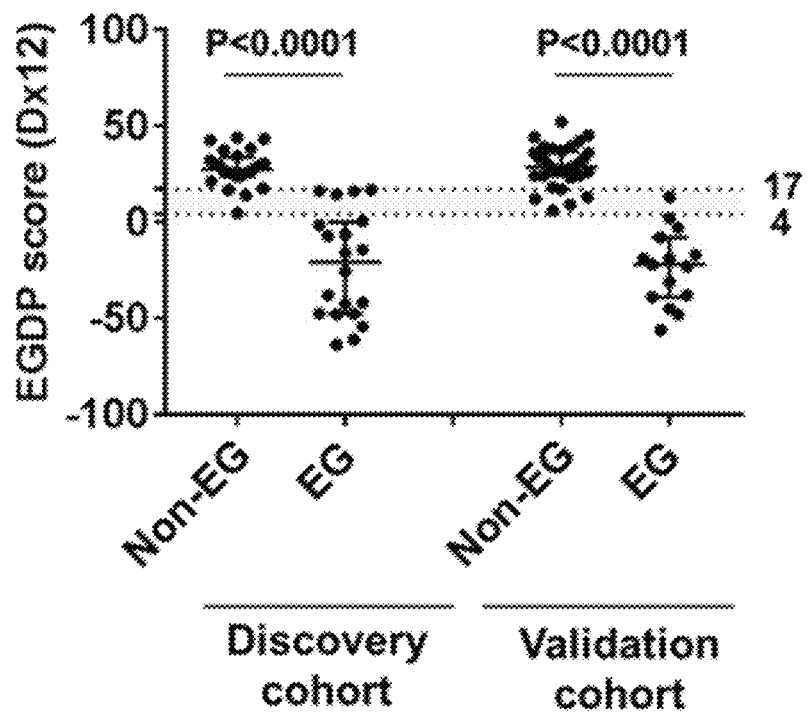
Figure 2D:
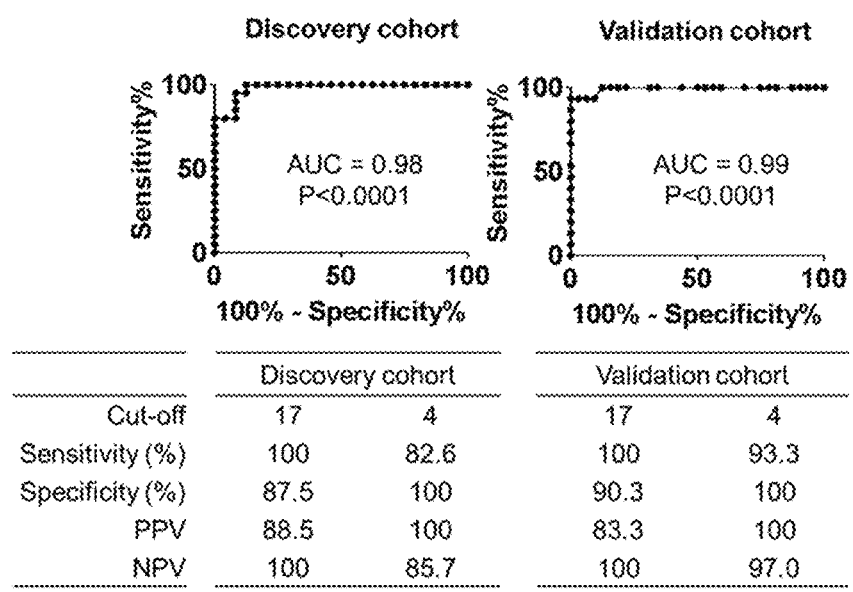
Figure 2E:
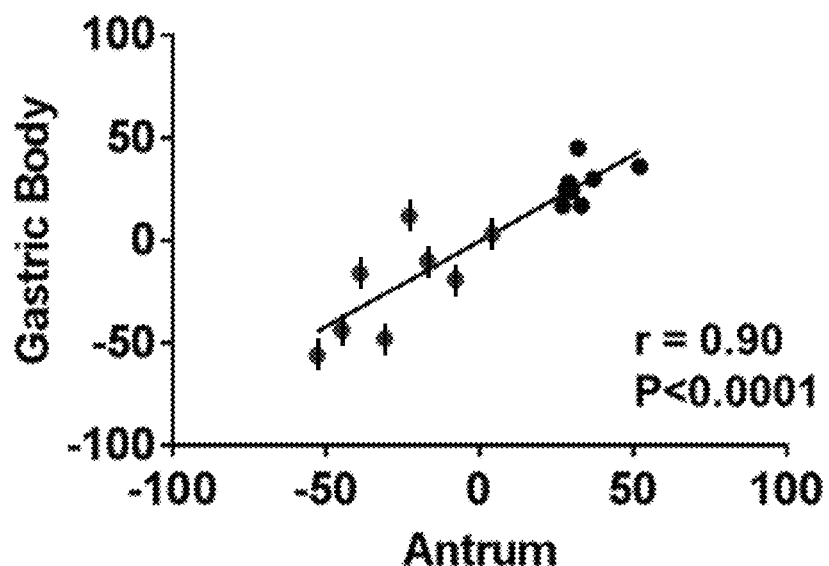
Figure 2F:
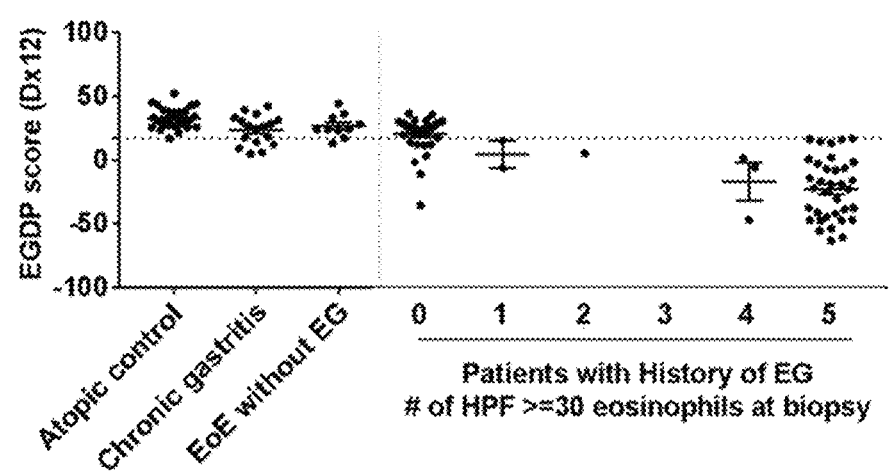

Genome-wide gene expression analysis was used to identify genes differentially transcribed in the gastric tissue of EG/EGE patients compared to normal healthy gastric tissue. FIG. 1A shows a heat map of 1,226 differentially dysregulated genes' expressions (adjusted P<0.05, ≥2-fold change). Gastric biopsies (total n=158; discovery n=83 and validation n=75) were analyzed. FIG. 1B shows a Venn diagram of the genes whose expression was dysregulated by both RNA seq and microarray analysis. A tissue-based platform (EGDP) was developed using statistical screening starting with 48 EG/EGE genes, resulting in 12 genes whose expression differentiated EG/EGE from normal healthy tissue with adjusted P<0.01 and fold change≥5-fold change (FIG. 2A). The twelve-gene/-dimension expression data on non-EG/EGE controls and patients with EG/EGE were reduced to 3D presentation by principal component analysis (PCA) for visual presentation of the expression distance between samples (FIG. 2B) and an EGDP score was developed based on dimensionality reduction to distinguish EG/EGE vs non- EG/EGE (FIG. 2C). After optimizing potential score ranges, a score≤4 yielded a PPV=100%, a score≥17 and NPV=100%, and only 12.8% of subjects had an indeterminate score by this classification scheme (FIG. 2D). There was a linear correlation of EGDP score between the gastric antrum and body mucosa (FIG. 2E). When analyzed by EGDP score, all of the patients with intermediate tissue eosinophil levels can be diagnosed as EG/EGE (FIG. 2F).

TABLE 1

Differentially regulated genes in EG/EGE

| Gene abbreviation | Name |
|---|---|
| ACPP | Acid phosphatase, prostate |
| ANXA1 | Annexin A1 |
| AREG | Amphiregulin |
| ATP4A | ATPase, H$^+$/K$^+$ transporting subunit alpha |
| BMP3 | Bone morphogenetic protein 3 |
| CCK | Cholecystokinin |
| CCL11 | C-C motif chemokine ligand 11 (eotaxin-1) |
| CCL18 | C-C motif chemokine ligand 18 |
| CCL24 | C-C motif chemokine ligand 24 (eotaxin-2) |
| CCL26 | C-C motif chemokine ligand 26 (eotaxin-3) |
| CCR3 | C-C motif chemokine receptor 3 |
| CDH26 | Cadherin 26 |
| CHIA | Chitinase, acidic |
| CLC | Charcot-Leyden crystal galectin |
| COL2A1 | Collagen type II alpha 1 chain |
| CPA3 | Carboxypeptidase A3 |
| CXCL8 | C-X-C motif chemokine ligand 8 |
| DEFB1 | Defensin beta 1 |
| DUOXA2 | Dual oxidase maturation factor 2 |
| DUOX2 | Dual oxidase 2 |
| EGLN3 | Egl-9 family hypoxia inducible factor 3 |
| GABRA1 | Gamma-aminobutyric acid (GABA) type A receptor, alpha 1 subunit |
| GLDN | Gliomedin |
| HIF1A | Hypoxia inducible factor 1 subunit alpha |
| HPGDS | Hematopoietic prostaglandin D synthase |
| IL1RL1 | Interleukin 1 receptor-like 1 |
| IL4 | Interleukin 4 |
| IL5 | Interleukin 5 |
| IL5RA | Interleukin 5 receptor subunit alpha |
| IL13 | Interleukin 13 |
| IL13RA2 | Interleukin 13 receptor subunit alpha 2 |
| IL17A | Interleukin 17A |
| IL33 | Interleukin 33 |
| ITLN1 | Intelectin 1 |
| KLK7 | Kallikrein-related peptidase 7 |
| MADCAM1 | Mucosal vascular addressin cell adhesion molecule 2 |
| MUC4 | Mucin 4, cell-surface associated |
| NCF2 | Neutrophil cytosolic factor 2 |
| NPY | Neuropeptidase Y |
| PGA4 | Pepsinogen 4, group 1 (pepsinogen A) |
| S100G | S100 calcium-binding protein G |
| SLC26A7 | Solute carrier family 26 member 7 |
| SST | Somatostatin |

TABLE 1-continued

Differentially regulated genes in EG/EGE

| Gene abbreviation | Name |
|---|---|
| TAC1 | Tachykinin precursor 1 |
| TCN1 | Transcobalamin 1 |
| TGFBR1 | Transforming cofactor beta receptor 1 |

Figure 3A:
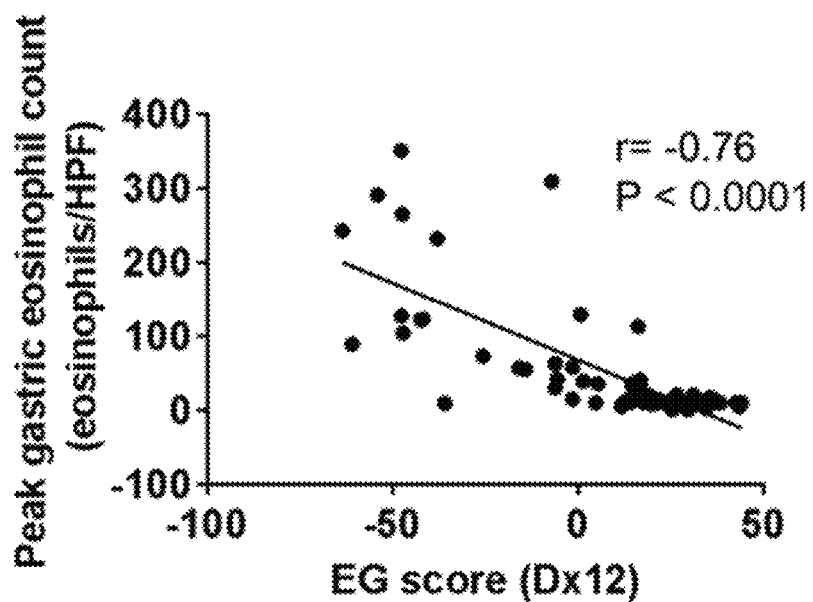
FIGS. 3A-D: Associations among EGDP and histological and endoscopic features. A linear correlation between the EGDP score and (A) gastric eosinophils/HPF and (B) endoscopic severity, with Spearman r and P values shown. (C) Associations and hierarchic relationships between the EG/EGE diagnostic panel (EGDP) and EG/EGE histologic features based on gene expression profile correlations and (D) associations and hierarchic relationships between the EG/EGE diagnostic panel (EGDP) and endoscopic features based on gene expression profile correlations.
Figure 3B:
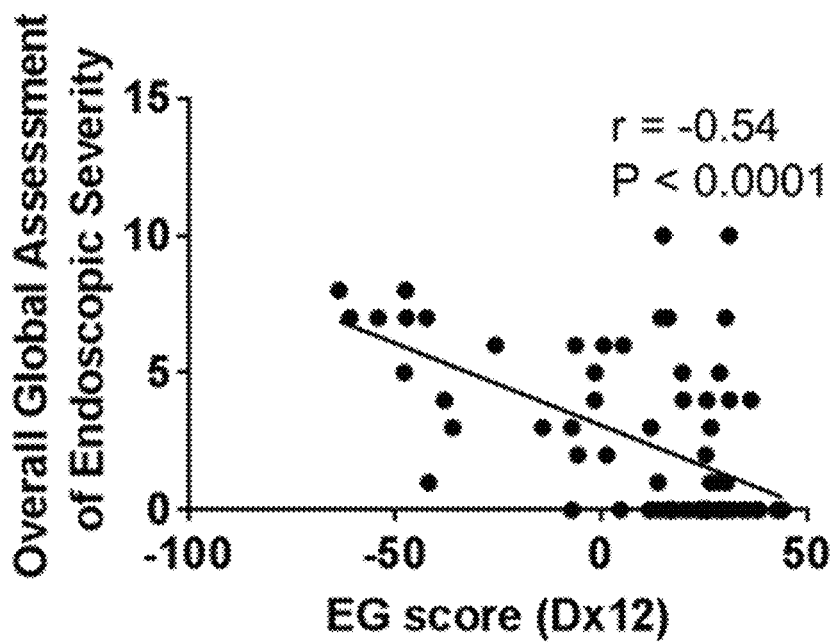
Figure 3C:
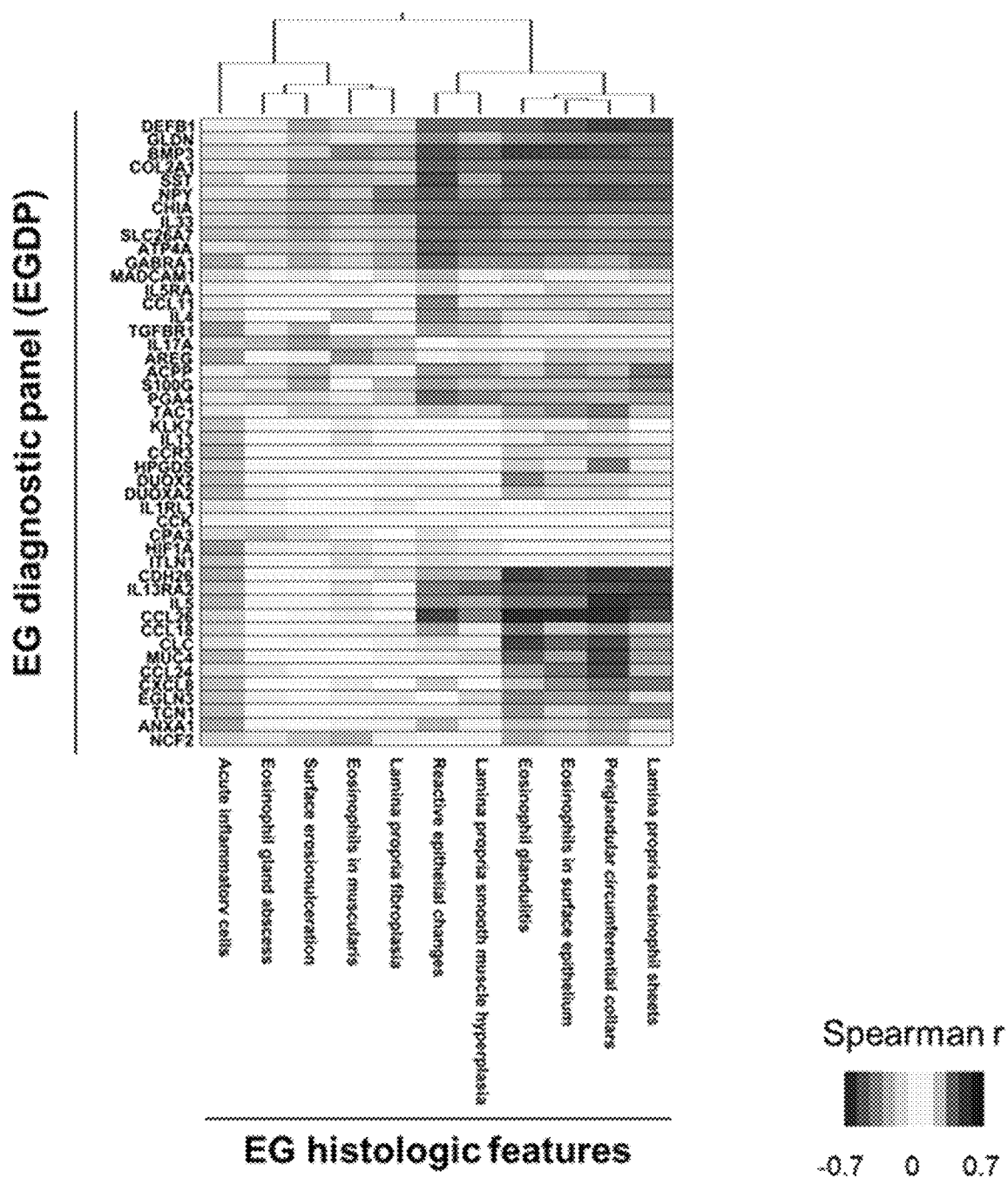
Figure 3D:
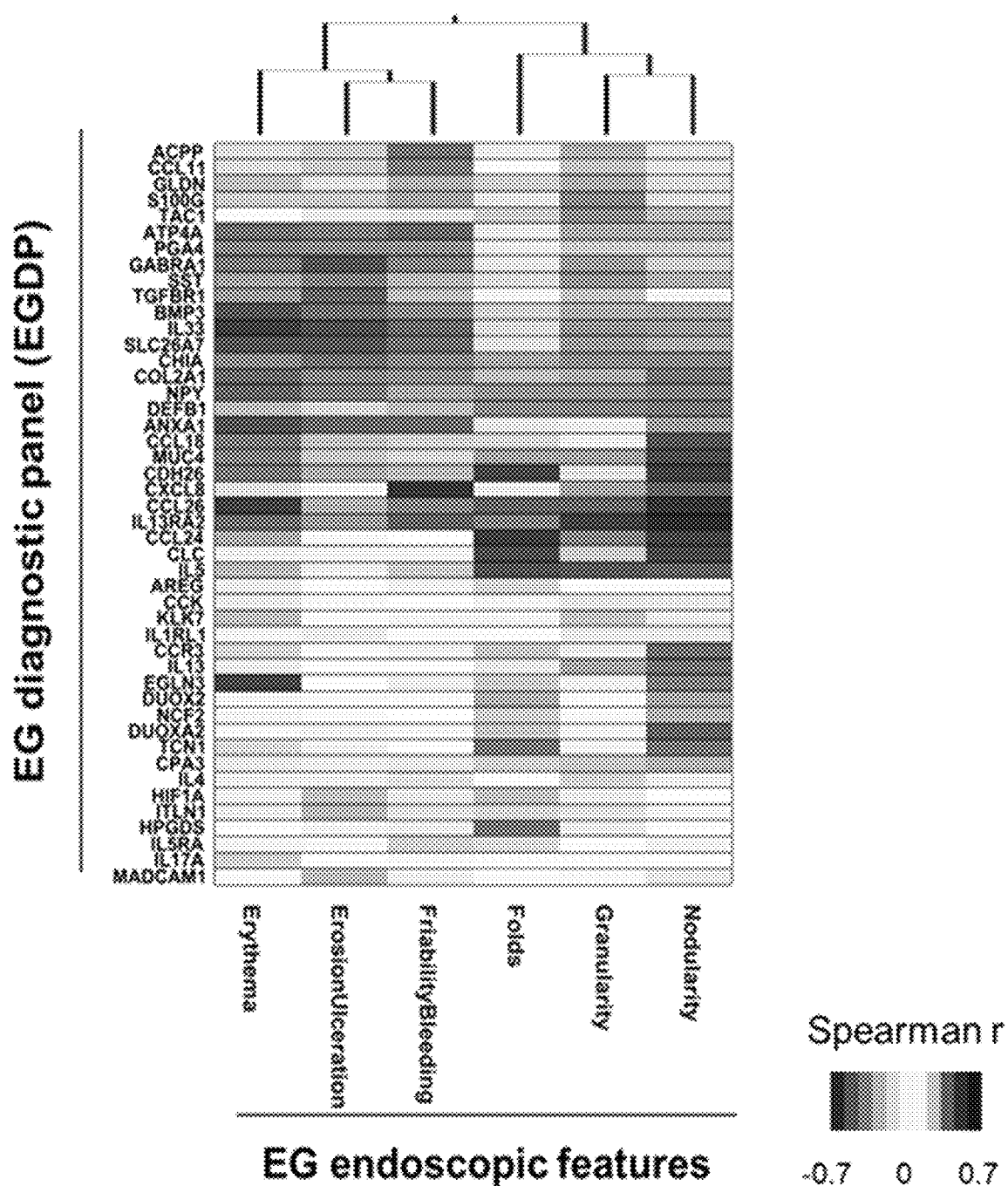

There was a linear correlation between the EGDP score and gastric eosinophils per high power field (FIG. 3A) and endoscopic severity (FIG. 3B). Associations and hierarchic relationships with EG/EGE histologic features are shown in FIG. 3C, and with endoscopic features in FIG. 3D.

In summary, for the tissue-based platform, the EGDP score a) identified active EG/EGE patients (P<0.0001, AUC≥0.98) in both cohorts; b) effectively monitored disease activity based on tissue eosinophil levels in longitudinally collected samples (P=0.0078); c) showed comparable levels and high correlation between the gastric antrum and body samples from the same patient (r=0.90, P<0.0001); d) demonstrated significant correlation with gastric peak eosinophil levels (r=−0.76, P<0.0001), endoscopic severity (r=−0.54, P<0.0001), histological glandulitis (r=−0.71, P<0.0001) and endoscopic nodularity (r=−0.55, P<0.0001). CCL26 was the most substantial gene associated with gastric eosinophilia, histological features, and endoscopic findings (P<0.0001).

Figure 4A:
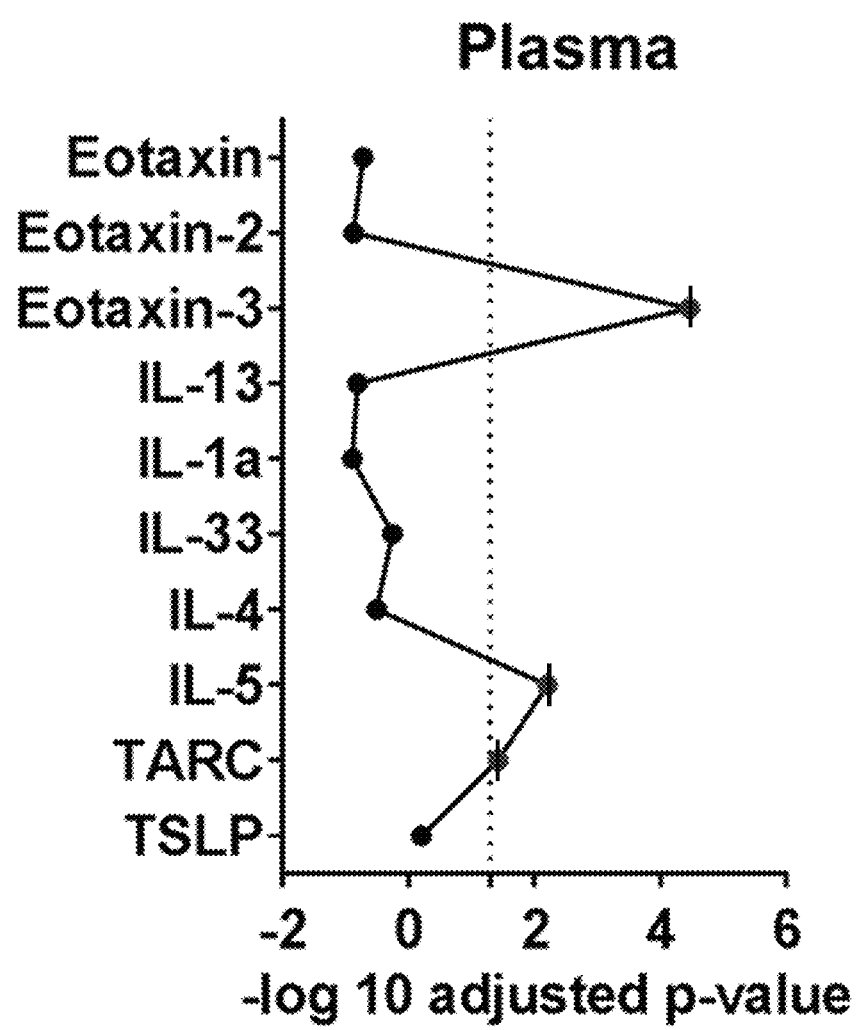
Figure 4B:
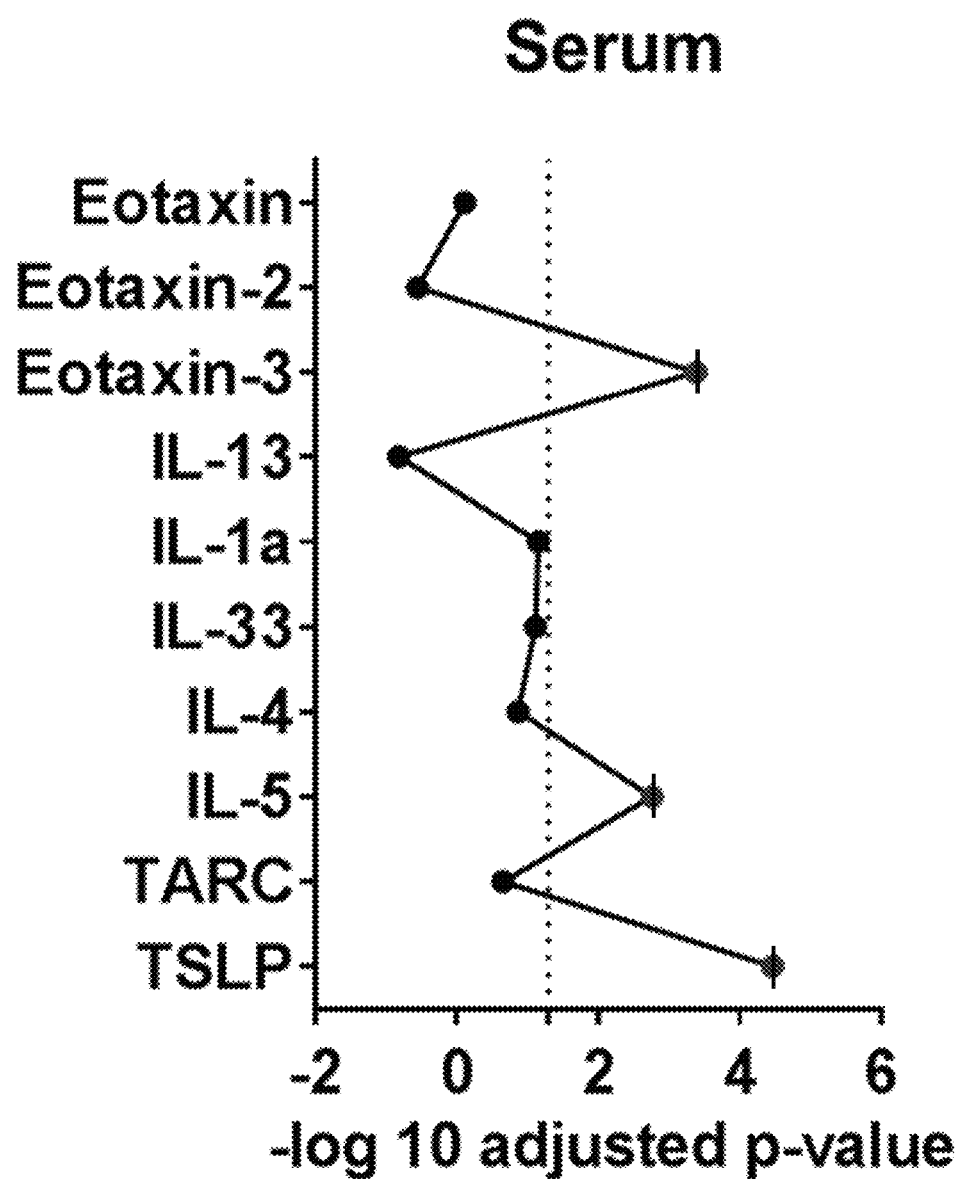
Figure 5A:
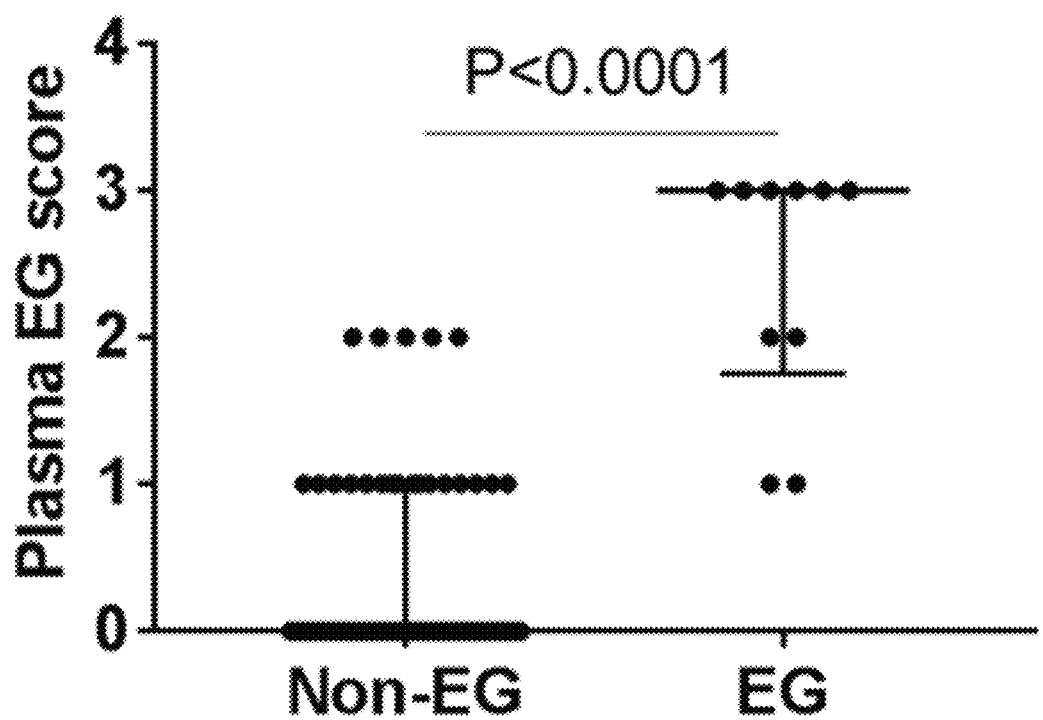
FIGS. 5A-D: Diagnostic performance of blood EG/EGE scores. Blood EG/EGE scores were developed based on dimensionality reduction to distinguish EG/EGE vs. non-EG/EGE and to quantify EG/EGE systemic severity in (A) plasma and (B) serum. (C, D) ROC curves and performance of blood EG/EGE scores based on the AUC as calculated for 4 conditions: (C) for the plasma cohort, EG/EGE score for Eotaxin-3, IL-5, and TARC; and (D) for the serum cohort, EG/EGE score for Eotaxin-3, IL-5, and TSLP.
Figure 5B:
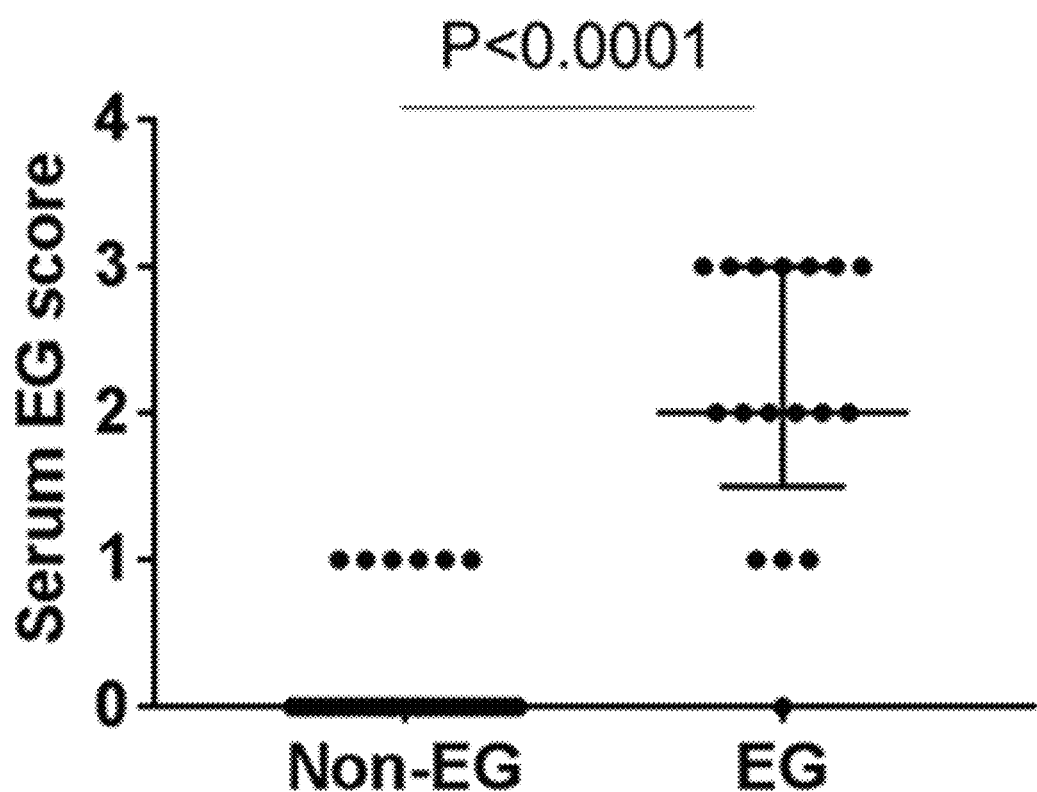
Figure 5C:
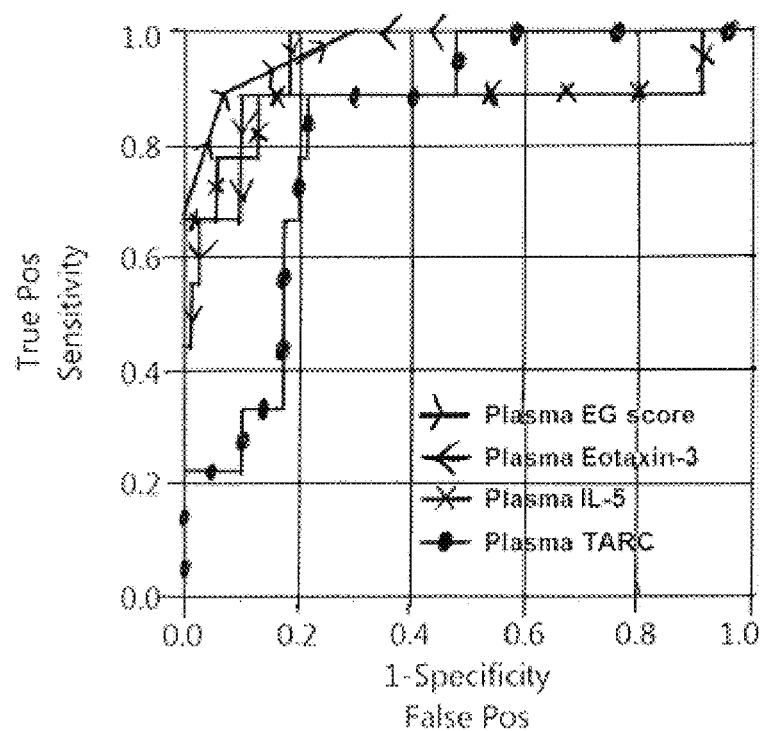
Figure 5D:
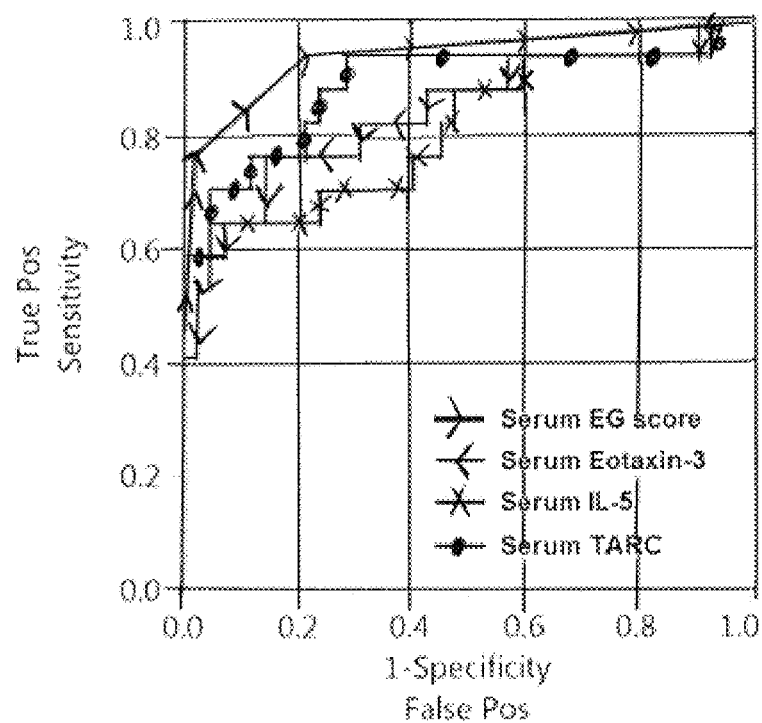
Figure 6:
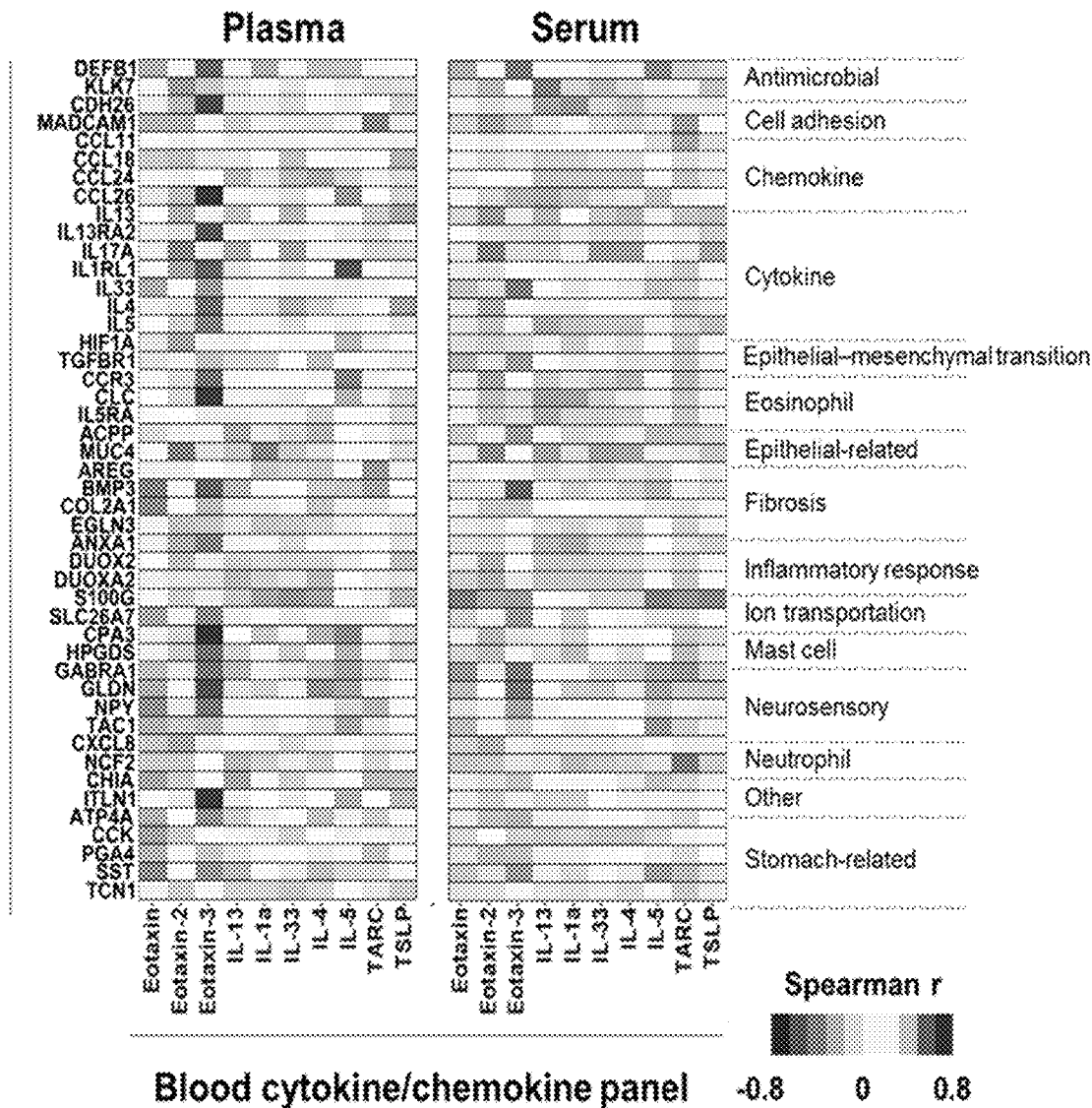
FIG. 6: Associations between local and systemic gene expression. Associations were determined between EGDP and blood biomarkers using Spearman r for the correlation between EGDP gene expression and plasma (left) and serum (right) biomarkers. A Spearman r-based heat diagram for the correlation at the gene level is shown.

For blood-based platforms, blood samples (total n=155; plasma n=81 and serum n=74) were analyzed. Among the 10 biomarkers embedded in the platform, a statistical screening was performed between the non-EG/EGE patients and patients with EG/EGE in the plasma and serum cohort, respectively, resulting in 3 biomarkers with adjusted P<0.05 (FIG. 4A-B). Blood EG/EGE scores were developed based on dimensionality reduction for the plasma and serum samples (FIG. 4C-D). FIG. 5A-D shows the diagnostic performance of the model. FIG. 6 shows a heat map of the associations between local and systemic gene expression. Associations were determined between EGDP and blood biomarkers using Spearman r for the correlation between EGDP gene expression and plasma (left) and serum (right) biomarkers.

In summary, the levels of three circulating cytokines significantly increased (P<0.05) in both EG/EGE cohorts (plasma: CCL26, IL-5 and TARC, serum: TSLP, CCL26 and IL-5). Levels of these circulating cytokines a) distinguished EG/EGE patients from non-EG/EGE patients (P<0.0001, AUC≥0.94); b) correlated with gastric eosinophil levels (plasma; r=0.61, P=0.0008, serum; r=0.66, P=0.0003); c) correlated with the EGDP score (plasma; r=−0.52, P=0.0135, serum; r=−0.53, P=0.0017); and was most notable for plasma CCL26 levels (r=−0.64, P=0.0006).

TABLE 2

Basic demographics of the cohorts used in this study.

| | Discovery cohort | | Validation cohort | |
|---|---|---|---|---|
| | Non-EG | EG | Non-EG | EG |
| Demographics | | | | |
| Age at biopsy (y) | 16.0 (13.6-23.7) | 18.3 (12.5-26.0) | 10.8 (4.7-16.8) | 12.6 (11.2-15.4) |
| Male | 9 (37.5%) | 13 (65.0%) | 16 (50.0%) | 8 (53.3%) |
| White | 24 (100%) | 17 (85.0%) | 32 (90.6%) | 13 (86.7%) |
| Treatment at biopsy | | | | |
| PPI treatment | 12 (50.0%) | 7 (53.9%) | 17 (53.1%) | 8 (53.3%) |
| Topical steroid | 2 (1%) | 8 (61.5%) | 1 (3.1%) | 5 (33.3%) |

TABLE 2-continued

Basic demographics of the cohorts used in this study.

| | Discovery cohort | | Validation cohort | |
|---|---|---|---|---|
| | Non-EG | EG | Non-EG | EG |
| Diet therapy | 8 (33.3%) | 6 (46.2%) | 5 (15.6%) | 9 (60.0%) |
| Peak gastric eosinophil count | 9 (6-14.8) | 118.5 (58.3-241.3) | 11 (5.5-17.5) | 77 (37-180.5) |

Data are n (%) or median (IQR).

Conclusions

We have developed tissue-based and circulating non-invasive biomarkers for EG/EGE. For the tissue-based platform, the EGDP score identified active EG/EGE patients (P<0.0001, AUC≥0.98), effectively monitored disease activity in longitudinally collected samples, showed comparable levels and high correlation between the gastric antrum and body and demonstrated significant correlation with gastric peak eosinophil levels and endoscopic severity.

It was determined that EGDP can biologically divide histological and endoscopic findings into distinct categories suggesting differences in these pathways. For blood-based platforms, the levels of three relevant proteins (cytokines/chemokines) significantly increased in both EG/EGE cohorts. Further, the levels of these circulating cytokines/chemokines distinguished EG/EGE patients from non-EG/EGE patients (P<0.0001, AUC≥0.94) and were closely correlated with gastric eosinophil levels and EGDP score.

Lastly, CCL26 has emerged as the strongest tissue and circulating disease biomarker. We have uncovered robust associations among the EG/EGE molecular profile, eosinophilic glandulitis, and endoscopic nodularity, providing insight into a better understanding of the pathogenesis of EG/EGE.

Expanded Study

The studies above were expanded to include a total of 185 subjects (patients with EG, n=74; control subjects without EG, n=111) and 201 gastric biopsy specimens (RNA sequencing, n=21; EGDP discovery, n=104; EGDP validation, n=76) and 155 blood samples (plasma, n=81; serum, n=74) for analyses. Demographic and clinical characteristics of the study cohort and subsets, including patients with EG and clinically relevant control subjects without EG, are published in *J Allergy Clin Immunol* 145:255-269 (2020), the content of which is hereby incorporated by reference in its entirety. Among all of the study subjects, age ranged from 1 to 67 years, with 124 (67%) pediatric and 61 (33%) adult subjects. There was a similar proportion of both sexes, with 90 male (48.6%) and 95 female (51.4%) subjects; the majority of subjects were white (91.4%). Peak gastric eosinophil counts ranged from 0 to 352 eosinophils/hpf (patients with active EG, 36-352 eosinophils/hpf; patients with inactive EG, 2-29 eosinophils/hpf; control subjects without EG, 0-28 eosinophils/hpf). Control subjects without EG (n=111) included patients with atopic comorbidities (n=47 [42.3%]), chronic gastritis (n=44 [39.6%]), and active EoE without EG (n=20 [18.0%]). There were no significantly different baseline demographic features among the cohorts for the tissue-based (n=124) and blood-based (n=108) platforms. Focusing on patients with EG (n=74), 46 (62%) had concurrent eosinophilia in the esophagus, 2 (3%) had concurrent eosinophilia in the colon, and 3 (4%) had concurrent eosinophilia in both the esophagus and colon. In the tissue- and blood-based platforms active EG did not reveal any significant differences from control subjects without EG in age, sex, race, atopic status, or proton pump inhibitor therapy at the time of biopsy, whereas patients with active EG had significantly greater levels in the disease parameters (peak/average gastric eosinophil counts, endoscopic severity, and histologic severity; P<0.01, respectively) and a greater rate of treatment (ongoing diet therapy, topical steroid therapy, and systemic steroid therapy).

Using this expanded cohort, and the 48 informative genes discussed above, we determined the minimal number of genes whose differential expression would distinguish patients with active EG (n=21) from control subjects (n=23) in a discovery cohort. Using relatively stringent criteria (>10-fold change, FDR P<0.01), 18 differentially expressed genes completely separated the 2 groups (FIGS. 7, A and B). Among the 18 genes, 8 were upregulated genes related to cytokines/chemokines (CCL26, CCL18, IL13RA2, and IL5), eosinophilia (CLC), cell adhesion (CDH26), antimicrobial defense (KLK7), and the epithelium (MUC4), and 10 were downregulated genes related to antimicrobial defense (DEFB1), fibrosis (BMP3 and COL2A1), ion transportation (SLC26A7), neurosensory activity (GABRA1, GLDN, NPY, and TAC1), and stomach-related processes (ATP4A and SST).

With the goal of developing a quantitative diagnostic cutoff, the EGDP18 score was developed to distinguish patients with EG versus control subjects without EG and to quantify the severity of EG. On the basis of the 18 significant and reproducible differential genes, we made CT sums of the upregulated genes and downregulated genes separately and then combined the 2 sums considering their different direction of dysregulation. The EGDP18 score was significantly decreased in patients with active EG compared with that in control subjects without EG in the discovery cohort (P<0.0001) and similarly decreased in the validation cohort (P<0.0001; FIG. 7C). ROC analysis demonstrated an excellent diagnostic merit (P<0.0001, AUC>0.95) in both cohorts (FIG. 7D). After investigation by setting optimal cutoff points, a score of less than 0 resulted in a positive predictive value of 100% and a negative predictive value of greater than 94% (FIG. 7D). Of note, the EGDP18 score is inversely correlated with disease severity, as defined by eosinophil counts when analyzed cross-sectionally (r=−0.83, P<0.0001; FIG. 7E) and longitudinally (P=0.0078; FIG. 7F). The EGDP18 score showed comparable levels and high correlation between the gastric antrum and body (n=8, r=0.85, P<0.0001; FIG. 7G). Among patients with active EG, the EGDP18 score showed consistency across geographically diverse sites and comparable levels across ages (pediatric vs adult patients), atopic status (atopy vs no atopy), coexistence with EoE (EG only vs EG with EoE), and treatment status at biopsy (ongoing therapy including diet and steroids vs no therapy. Interestingly, the EGDP18 score was able to classify patients with intermediate tissue eosinophil counts (i.e., the number of hpfs with >30 eosinophils, n=1-4 hpfs). When these patients were analyzed by using the EGDP18 score (n=8, all of them were clinically symptomatic), 5 (63%) patients were molecularly equivalent to having active EG (FIG. 7H).

We next used this expanded cohort to refine our blood-based platforms. Focusing on plasma and serum samples from patient cohorts with and without EG, we designed a multiplex immunoassay containing 10 EG relevant cytokines/chemokines, particularly those based on type 2 immunity, as reflected in the functional predictions found in the EG transcripts. Notably, patients with active EG showed significantly greater levels of 3 cytokines in the plasma and 3 cytokines in the serum (plasma eotaxin-3/CCL26, IL-5, and TARC/CCL17 and serum TSLP, eotaxin-3/CCL26, and IL-5, respectively; FIGS. 8, A and B), suggesting that the activity of the disease consistently affects these cytokines systemically.

On the basis of the levels of these dysregulated cytokines and chemokines, we refined our circulation-based EG biomarker scoring system for plasma and serum. The blood-based EG score differentiated patients with active EG from control subjects without EG in both the plasma and serum cohorts (P<0.0001; FIGS. 8, C and D). Notably, patients with active EG had significantly higher scores than did patients with inactive EG (plasma EG score: P<0.0001; serum EG score: P 5.0012; FIGS. 8, E and F).

To determine their diagnostic performances, ROC analyses were constructed to investigate the use of blood EG scores and cytokine/chemokine levels alone (FIG. 9A-9D). The plasma EG score yielded an AUC of 0.93, whereas levels of eotaxin-3 alone yielded an AUC of 0.89, levels of TARC alone yielded an AUC of 0.82, and levels of IL-5 alone yielded an AUC of 0.80. The serum EG score yielded an AUC of 0.91, whereas levels of TSLP alone yielded an AUC of 0.86, levels of eotaxin-3 alone yielded an AUC of 0.80, and levels of IL-5 alone yielded an AUC of 0.77.

In this expanded study, we determined that a diagnostic score limited to changes in a subset of 18 genes, referred to as the EGDP18 score, is sufficient to allow EG diagnosis relative to control subjects (sensitivity of 88% to 95% in the discovery and validation cohort and specificity of 100%), including control subjects without EG and patients with EGID limited to the esophagus; (3) determined that the EGDP18 score can robustly separate patients with active EG from those with inactive EG, strongly correlates with gastric eosinophil levels (r=-0.83, P<0.0001), and potentially aids in diagnostic classification of patients with intermediate eosinophil levels; (4) determined that expression of specific genes tracks with tissue eosinophilia, namely CCL26, CLC, IL13RA2, BMP3, IL5, CDH26, CCL18, NPY, HPGDS, and SST; (5) linked the magnitude of molecular changes to endoscopic changes, most notably associating nodularity and granularity with a subset of type 2 inflammatory genes, including CCL26 and IL13RA2, respectively; (6) linked the magnitude of molecular changes to histologic changes, with CCL26 levels most notably strongly associated with periglandular circumferential collars (r=0.74, P=7.0E-21) and eosinophil glandulitis (r=0.68, P=2.0E-16), whereas IL13RA2 correlated most notably with periglandular circumferential collars (r=0.67, P=7.0E-16) and lamina propria eosinophil sheets (r=0.67, P=5.0E-16); (7) identified circulating biomarkers that reflect local changes in the stomach, most notably the gastric eosinophilia; and (8) demonstrated that combined levels of plasma eotaxin-3, TARC, and IL-5 have the capacity to diagnose EG disease and monitor disease activity with high sensitivity and specificity (100% and 72%, respectively).

To our knowledge, this is the first EGID study simultaneously addressing tissue gene expression signatures and circulating cytokine profiles in the same disorder with autologous samples across different collecting centers. This study was not intended to replace the histologic method but rather to provide at least 2 alternative platforms to more precisely and sensitively diagnose EG. It is conceivable that the circulating markers could serve as an early noninvasive test during EGID/EG screening, whereas the tissue signature profiling (EGDP) could be used for definitive diagnostic confirmation. The combination of both would provide molecular tools to diagnose, monitor, and potentially further subtype (eg, endotype) knowledge of EG.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating eosinophilic gastritis (EG) or eosinophilic gastroenteritis (EGE) in a subject in need thereof, the method comprising
   a) determining amounts of CCL26 protein, IL-5 protein, and TSLP protein, or peptide or polypeptide fragments thereof in a serum fraction of a blood sample obtained from the subject at an initial time point;
   b) detecting an elevated amount of two or more of CCL26, IL-5, and TSLP proteins, or peptide or polypeptide fragments thereof, in the serum fraction, relative to a predetermined control value;
   c) diagnosing the subject as having EG or EGE; and
   d) administering to the subject diagnosed with EG or EGE
      i) a therapeutic agent selected from the group consisting of a glucocorticoid, a leukotriene inhibitor, azathioprine, an anti-histamine, a mast-cell stabilizer, a macrolide antibiotic, and anti-cytokine therapy, or ii) a dietary therapy which alleviates one or more symptoms or complications of EG or EGE selected from a restricted diet, an elemental diet, and an elimination diet.

2. The method of claim 1, wherein the subject is human.

3. The method of claim 1, further comprising an initial step of obtaining a blood sample from the subject.

* * * * *